(12) United States Patent
Kuduk et al.

(10) Patent No.: US 9,206,200 B2
(45) Date of Patent: Dec. 8, 2015

(54) N-LINKED LACTAM M1 RECEPTOR POSITIVE ALLOSTERIC MOGULATORS

(75) Inventors: Scott D. Kuduk, Harleysville, PA (US); Douglas C. Beshore, Lower Gwynedd, PA (US); Zhi-Qiang Yang, Schwenksville, PA (US); Youheng Shu, Blue Bell, PA (US); Daniel Pitts, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/117,341

(22) PCT Filed: May 11, 2012

(86) PCT No.: PCT/US2012/037410
§ 371 (c)(1),
(2), (4) Date: Nov. 12, 2013

(87) PCT Pub. No.: WO2012/158475
PCT Pub. Date: Nov. 22, 2012

(65) Prior Publication Data
US 2015/0065498 A1     Mar. 5, 2015

Related U.S. Application Data

(60) Provisional application No. 61/487,070, filed on May 17, 2011.

(51) Int. Cl.

| C07D 519/00 | (2006.01) |
|---|---|
| C07D 417/04 | (2006.01) |
| C07D 471/08 | (2006.01) |
| C07D 401/14 | (2006.01) |
| C07D 405/14 | (2006.01) |
| C07D 401/06 | (2006.01) |
| C07D 401/08 | (2006.01) |
| C07D 403/06 | (2006.01) |
| C07D 403/08 | (2006.01) |
| C07D 417/08 | (2006.01) |
| C07D 471/04 | (2006.01) |
| C07D 487/08 | (2006.01) |
| C07D 491/10 | (2006.01) |
| C07D 209/64 | (2006.01) |

(52) U.S. Cl.
CPC ............ *C07D 519/00* (2013.01); *C07D 209/64* (2013.01); *C07D 401/06* (2013.01); *C07D 401/08* (2013.01); *C07D 401/14* (2013.01); *C07D 403/06* (2013.01); *C07D 403/08* (2013.01); *C07D 405/14* (2013.01); *C07D 417/08* (2013.01); *C07D 471/04* (2013.01); *C07D 471/08* (2013.01); *C07D 487/08* (2013.01); *C07D 491/10* (2013.01)

(58) Field of Classification Search
USPC ...................... 514/232, 290; 546/84; 548/427
See application file for complete search history.

(56) References Cited

U.S. PATENT DOCUMENTS 8,697,690 B2 *   4/2014   Beshore et al. ............ 514/232.8

FOREIGN PATENT DOCUMENTS

| WO | WO2004073639 | 9/2004 |
|---|---|---|
| WO | WO2005030188 | 4/2005 |
| WO | WO2005056552 | 6/2005 |
| WO | WO2007067489 | 6/2007 |
| WO | WO2011049731 | 4/2011 |
| WO | 2012003147 | * 1/2012 |

OTHER PUBLICATIONS

Abraham Fisher, Therapeutic Strategies in Alzheimer's Disease: M1 Muscarinic Agonists, Jpn. J. Pharmacol., 2000, pp. 101-112, 84.
Birdsall, Multiple Allosteric Sites on Muscarinic Receptors, NPL-Birdsall-2001-2517, 2001, 2517-2524, 58, Life Science.
Brauner-Osborne, Pharmacology of Muscarinic Acetylcholine Receptor Subtypes (ml-m5): High Throughout Assays in Mammalian Cells, E. Journal of Pharmacology, 1996, 93-102, 295.
Christopoulos, Allosteric Binding Sites on Cell-Surface Receptors: Novel Targets for Drug Discovery, Nature, 2002, 198-210, 1.
Eglen, Therapeutic Opportunties from Muscarinic Receptor Research, Trends in Pharmacological Sciences, Aug. 2001, 409-414, 8.
Espinoza-Fonesca et al., Idenfication of Multiple Allosteric Sites on the M1 Muscarinic Acetylcholine Receptor, FEBS Letters, 2005, 6726-6732, 579, Elsevier.
Lazareno, Analogs of WIN 62,577 Define a Second Allsoteric Site on Muscarinic Receptors, Molecular Pharmacology, 2002, 1492-1505, 62.

(Continued)

*Primary Examiner* — Rita Desai
(74) *Attorney, Agent, or Firm* — Sylvia A. Ayler; John C. Todaro

(57) ABSTRACT

The present invention is directed to N-linked lactam compounds of general formula (I) which are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

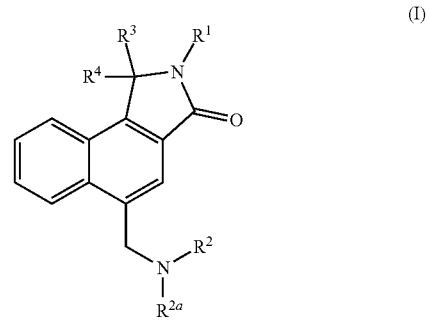

13 Claims, No Drawings

(56) References Cited

OTHER PUBLICATIONS

Lazereno, Allosteric Interactions of Staurosporine and Other Indolocarbazoles with N-[Methyl-3H]Scopolamine and Acetylcholine at Muscarinic Receptor Subtypes: Identification of a Second Allosteric Site, Molecular Pharmacology, Mar. 22, 2000, 194-207, 58.

Peng et al., The Predicted 3D Structures of the Human M1 Muscarinic Acetylcholine Receptor with Agonist or Antagonist Bound,, Chem Med Chem, 2006, pp. 878-890, 1.

Spalding et al., Discovery of an Ectopic Activation Site on the M1 Muscarinic Receptor, Site on the M1 Muscarinic Receptor, 2002, pp. 1297-1302, 61, Molecular Pharmacology, US.

* cited by examiner

N-LINKED LACTAM M1 RECEPTOR POSITIVE ALLOSTERIC MOGULATORS

CROSS REFERENCE TO RELATED APPLICATIONS

This application is a 371 of International Application No. PCT/US2012/037410 filed on May 11, 2012, which claims the benefit under 35 U.S.C. 119(e) of U.S. Provisional Application No. 61/487,070, filed May 17, 2011.

FIELD OF THE INVENTION

The invention is directed to a class of N-linked lactam compounds, their salts, pharmaceutical compositions comprising them and their use in therapy of the human body. In particular, the invention is directed to a class of N-linked lactam compounds which are muscarinic M1 receptor positive allosteric modulators, and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, TRENDS in Pharmacological Sciences, 2001, 22:8, 409-414.

In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, Jpn J Pharmacol, 2000, 84:101-112.

However, M1 ligands which have been developed and studied for Alzheimer's Disease have produced side effects common to other muscarinic receptor ligands, such as sweating, nausea and diarrhea. See Spalding et al, Mol Pharmacol, 2002, 61:6, 1297-1302. See also WO2005056552, WO2005030188 and WO2007067489.

The muscarinic receptors are known to contain one or more allosteric sites, which may alter the affinity with which muscarinic ligands bind to the primary binding or orthosteric sites. See, e.g., S. Lazareno et al, Mol Pharmacol, 2002, 62:6, 1491-1505; S. Lazareno et al, Mol Pharmacol, 2000, 58, 194-207.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is directed to novel N-linked lactam compounds of generic formula (I) described below, or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to N-linked lactam compounds of general formula (I)

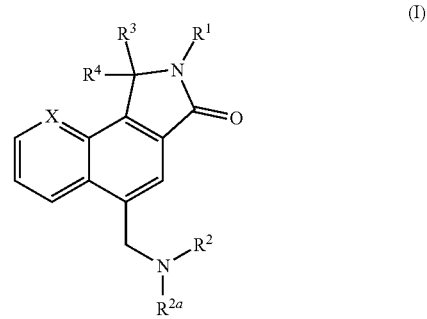

and pharmaceutically acceptable salts thereof, wherein
X=CH or N
$R^1$ represents $C_{3-10}$cycloalkyl, $C_{6-10}$ aryl and $C_{5-10}$ heterocyclyl, said cycloalkyl, aryl and heterocyclyl optionally substituted with 1 to 3 groups of $R^a$, $R^2$ and $R^{2a}$ independently represent H, and $C_{1-6}$ alkyl, said alkyl optionally substituted with 1 to 3 groups of $R^a$,
or $R^2$ and $R^{2a}$ together with the nitrogen to which they are attached combined to form a $C_{3-10}$ heterocyclic ring wherein 1 to 2 carbon atoms on the ring are optionally interrupted by 1 to 2 heteroatoms selected from N, O and S, said heterocyclic ring optionally substituted with 1 to 3 groups of $R^a$,
$R^3$ and $R^4$ independently represent:
  (1) hydrogen,
  (2) —$C_{1-6}$alkyl, optionally substituted with 1 to 3 groups of $R^a$,
  (3) $C_{3-10}$ cycloalkyl,
  (4) $C(O)OR^3$,
or $R^3$ and $R^4$ can combine with the atom to which they are attached to form a 3 to 6 spirocyclalkyl ring,
$R^a$ represents:
  (1) hydroxyl,
  (2) halogen,
  (3) $C_{1-6}$alkyl,
  (4) $(CH_2)_nC_{6-10}$aryl, which is unsubstituted or substituted with 1 to 3 groups of $R^b$,
  (5) $(CH_2)_n$heterocyclyl, which is unsubstituted or substituted with 1 to 3 groups of $R^b$, and
  (6) —CN,
  (7) —O—,
  (8) $(CH_2)_nC_{1-4}$haloalkyl,
  (9) $COOR^3$,
  (10) $C_{3-10}$cycloalkyl,
  (11) $C(O)C_{1-6}$alkyl,
  (12) $S(O)_2C_{1-6}$alkyl,
  (13) $C_{2-4}$alkynyl,
  (14) $C_{2-4}$alkenyl, and
  (15) 2 or more adjacent $R^a$ groups may combine with the atoms to which they are attached to form a $C_{3-10}$ carbocyclic ring with 1 to 2 carbons atoms on the ring optionally interrupted by 1 to 2 heteroatoms selected from N, O, and S,
wherein said alkyl, aryl, heterocyclyl, cycloalkyl, alkynyl, alkenyl, and carbocyclic ring are optionally substituted with 1 to 3 groups of $R^b$,
$R^b$ represents:
  (1) hydroxyl,
  (2) halogen,
  (3) $C_{1-6}$alkyl, and
  (4) $C_{1-4}$haloalkyl,
  (5) —$OC_{1-6}$alkyl,
  (6) $C_{3-10}$cycloalkyl,
  (7) $C_{2-6}$alkenyl, and
  (8) $S(O)_2C_{1-6}$alkyl,
n is 0-4.

In one embodiment of the compounds of formula (I) X is N and all other variables are as originally described.

In another embodiment of the compounds of formula (I) X is CH and all other variables are as originally described.

In another embodiment of the compounds of formula (I) $R^3$ and $R^4$ are both hydrogen or one of $R^3$ and $R^4$ is hydrogen and the other is methyl and all other variables are as originally described.

In another embodiment of the compounds of formula (I) $R^1$ is optionally substituted $C_{6-10}$ aryl and all other variables are as originally described. A subembodiment of this invention is realized when $R^1$ is optionally substituted phenyl.

In another embodiment of the compounds of formula (I) $R^1$ is optionally substituted $C_{5-10}$ heterocyclyl and all other variables are as originally described. A subembodiment of this invention is realized when $R^1$ is optionally substituted pyrrolyl.

In another embodiment of the compounds of formula (I) $R^1$ is optionally substituted $C_{3-10}$ cycloalkyl and all other variables are as originally described. A subembodiment of this invention is realized when $R^1$ is optionally substituted cyclohexyl.

In another embodiment of the compounds of formula (I) $R^2$ and $R^{2a}$ independently represent hydrogen and $C_{1-6}$alkyl, said alkyl optionally substituted with 1 to 3 groups of $R^a$. A subembodiment of this invention is realized when $R^2$ and $R^a$ are both $C_{1-6}$ alkyl, preferably methyl or ethyl.

In another embodiment of the compounds of formula (I) $R^2$ and $R^{2a}$ together with the nitrogen to which they are attached combined to form a $C_{3-10}$ heterocyclic ring wherein 1 to 2 carbon atoms on the ring are optionally interrupted by 1 to 2 heteroatoms selected from N, O and S, said heterocyclic ring optionally substituted with 1 to 3 groups of $R^a$. A subembodiment of this invention is realized when $R^2$ and $R^{2a}$ combine to form optionally substituted piperidinyl, piperazinyl, morpholinyl, pyrrolidinyl, or benzpiperidinyl. Another subembodiment of this invention is realized when said piperidinyl, piperazinyl, morpholinyl, pyrrolidinyl, or benzpiperidinyl are substituted with 1 to 3 groups, preferably 1 to 2 groups, of $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl. Still another subembodiment of this invention is realized when $R^2$ and $R^{2a}$ combine to form a substituted $C_{3-10}$ heterocyclic ring which is substituted with 2 adjacent $R^a$ groups that combine with the atoms to which they are attached to form a 3-10 carbocyclic ring with 1 to 2 carbons atoms on the ring optionally interrupted by 1 to 2 heteroatoms selected from N, O, and S, said carbocyclic ring optionally substituted with 1 to 3 groups of $R^b$.

In yet another embodiment of the compounds of formula (I) $R^a$ is selected from the group consisting of methyl, ethyl, halo, CN, OH, $(CH_2)_nCF_3$, cyclopropyl, $(CH_2)_n$phenyl, $(CH_2)_n$pyridyl, piperazinyl, pyrimidinyl, pyrazolyl, and $C_{2-6}$alkynyl, or 2 adjacent $R^a$ groups that combine with the atoms to which they are attached to form a 3-10 carbocyclic ring with 1 to 2 carbons atoms on the ring optionally interrupted by 1 to 2 heteroatoms selected from N, O, and S, said carbocyclic ring optionally substituted with 1 to 3 groups of $R^b$.

Still another embodiment of the compounds of formula (I) is represented by structural formula Ia:

Ia or a pharmaceutically acceptable salt thereof wherein $R^3$, $R^4$, $R^2$, and $R^a$ are as originally described and A is selected from the group consisting of optionally substituted cyclohexyl, and pyranyl. A subembodiment of formula Ia is realized when the cyclohexyl, and pyranyl is substituted with one $R^a$ that is hydroxyl. Another subembodiment of formula Ia is realized when the hydroxyl substituent is ortho or meta relative to the point of ring attachment. Still another subembodiment of formula Ia is realized when A is hydroxycyclohexyl. Yet another subembodiment of formula Ia is realized when A is hydroxypyranyl. Another subembodiment of formula Ia is realized when X is N. Another subembodiment of formula Ia is realized when X is CH. Another subembodiment of formula Ia is realized when $R^2$ and $R^{2a}$ are $C_{1-6}$ alkyl. Another subembodiment of formula Ia is realized when $R^2$ and $R^{2a}$ combine to form optionally substituted piperidinyl, piperazinyl, morpholinyl, pyrrolidinyl, or benzpiperidinyl. Another subembodiment of this invention is realized when said piperidinyl, piperazinyl, morpholinyl, pyrrolidinyl, or benzpiperidinyl are substituted with 1 to 3 groups, preferably 1 to 2 groups, of $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl, said $R^a$ groups when possible optionally substituted with 1-3 groups of $R^b$. Still another subembodiment of formula Ia' is realized when $R^3$ and $R^4$ are both hydrogen, or one is hydrogen and the other is methyl. Another subembodiment of formula Ia is realized when A is selected from the group consisting of cyclohexyl, pyranyl, hydroxycyclohexyl, and hydroxypyranyl, X is N, $R^2$ and $R^{2a}$ are $C_{1-6}$ alkyl, or $R^2$ and $R^{2a}$. combine to form piperidinyl, piperazinyl, morpholinyl, pyrrolidinyl, or benzpiperidinyl, said piperidinyl, piperazinyl, morpholinyl, pyrrolidinyl, or benzpiperidinyl optionally substituted with 1 to 3 groups $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl and $R^3$ and $R^4$ are both hydrogen, or one of $R^3$ and $R^4$ is hydrogen and the other is methyl. Another subembodiment of formula Ia is realized when A is selected from the group consisting of cyclohexyl, pyranyl, hydroxycyclohexyl, and hydroxypyranyl, X is CH, $R^2$ and $R^{2a}$ are $C_{1-6}$ alkyl, or $R^2$ and $R^{2a}$. combine to form piperidinyl, piperazinyl, morpholinyl, pyrrolidinyl, or benzpiperidinyl, said piperidinyl, piperazinyl, morpholinyl, pyrrolidinyl, or benzpiperidinyl optionally substituted with 1 to 3 groups $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl and $R^3$ and $R^4$ are both hydrogen, or one of $R^3$ and $R^4$ is hydrogen and the other is methyl.

Still another embodiment of the compounds of formula (I) is represented by structural formula Ia':

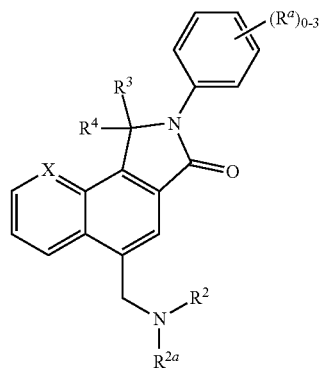

Ia' or a pharmaceutically acceptable salt thereof wherein $R^3$, $R^4$, $R^2$, and $R^a$ are as originally described. Another subembodiment of formula Ia is realized when X is N. Another subembodiment of formula Ia is realized when X is CH. Another subembodiment of formula Ia' is realized when $R^2$ and $R^{2a}$ are $C_{1-6}$ alkyl. Another subembodiment of formula Ia' is realized when $R^2$ and $R^{2a}$ combine to form optionally substituted piperidinyl, piperazinyl, morpholinyl, pyrrolidinyl, or benzpiperidinyl, preferably piperidinyl and piperazinyl. Another subembodiment of this invention is realized when said piperidinyl, piperazinyl, morpholinyl, pyrrolidinyl, or benzpiperidinyl are substituted with 1 to 3 groups, preferably 1 to 2 groups, of $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl, said $R^a$ groups when possible optionally substituted with 1 to 3 groups of $R^b$. Still another subembodiment of formula Ia' is realized when $R^3$ and $R^4$ are both hydrogen, or one is hydrogen and the other is methyl. Another subembodiment of formula Ia is realized when X is N, $R^2$ and $R^{2a}$ are $C_{1-6}$ alkyl, or $R^2$ and $R^{2a}$ combine to form piperidinyl, piperazinyl, morpholinyl, pyrrolidinyl, or benzpiperidinyl, said piperidinyl, piperazinyl, morpholinyl, pyrrolidinyl, or benzpiperidinyl optionally substituted with 1 to 3 groups of $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl and $R^3$ and $R^4$ are both hydrogen, or one of $R^3$ and $R^4$ is hydrogen and the other is methyl. Another subembodiment of formula Ia is realized when X is CH, $R^2$ and $R^{2a}$ are $C_{1-6}$ alkyl, or $R^2$ and $R^{2a}$ combine to form optionally substituted piperidinyl, piperazinyl, morpholinyl, pyrrolidinyl, or benzpiperidinyl, said piperidinyl, piperazinyl, morpholinyl, pyrrolidinyl, or benzpiperidinyl optionally substituted with 1 to 3 groups of $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl and $R^3$ and $R^4$ are both hydrogen, or one of $R^3$ and $R^4$ is hydrogen and the other is methyl.

Yet another embodiment of formula Ia' is represented by structural formula Ia":

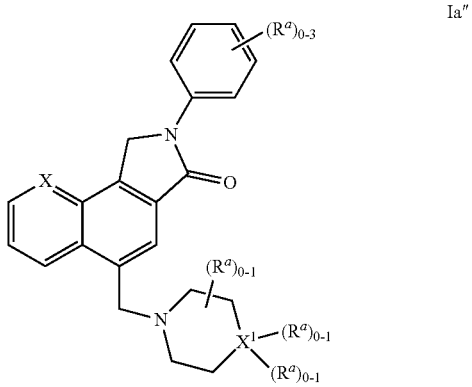

Ia"

wherein X and $R^a$ are as originally described and $X^1$ is X.
Another embodiment of the compounds of formula (I) is represented by structural formula Ib:

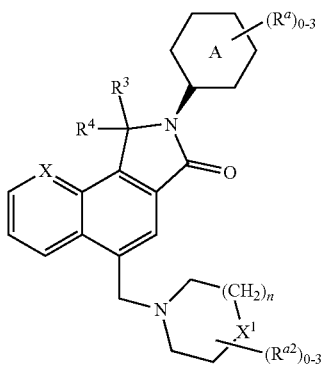

Ib or a pharmaceutically acceptable salt thereof wherein $R^a$, $R^3$, $R^4$, X and $X^1$ are as originally described, A is selected from the group consisting of optionally substituted cyclohexyl and pyranyl, n is 0 or 1, and $R^{a2}$ is $R^a$. A subembodiment of formula Ib is realized when $X^1$ is CH. A subembodiment of formula Ib is realized when $X^1$ is N. Another subembodiment of formula Ib is realized when X is CH. Another subembodiment of formula Ib is realized when X is N. Another subembodiment of formula Ib is realized when n is 0. Another subembodiment of formula Ib is realized when n is 1. A subembodiment of formula Ib is realized when the cyclohexyl, and pyranyl is substituted with one $R^a$ that is hydroxyl. Another subembodiment of formula Ib is realized when the hydroxyl substituent is ortho or meta relative to the point of ring attachment. Still another subembodiment of formula Ib is realized when A is hydroxycyclohexyl. Yet another subembodiment of formula Ib is realized when A is hydroxypyranyl. Another subembodiment of formula Ib is realized when up to 2 $R^{a2}$ are selected from the group consisting of methyl, ethyl, propyl, butyl, fluorine, chlorine, bromine, —O—, OH, CN, $(CH_2)_nCF_3$, $CH_2F$, $C_{2-4}$ alkenyl, $C_{2-4}$ alkynyl, $C_{2-4}$ alkynylphenyl, $(CH_2)_n$pyridyl, methxoxy, $SO_2Me$, COOEt, cyclopropyl, $(CH_2)_n$phenyl, pyrimidinyl, pyrazinyl, pyridazinyl, benzypiperidinyl, pyrazolyl, benzothiazolyl, quinolinyl, or two adjacent $R^{a2}$ groups combine to form benzotetrahydrofuranyl, oxetanyl, said alkyl, aryl and heterocyclyl groups of $R^{a2}$ when possible optionally substituted with 1 to 3 groups of $R^b$. Another subembodiment of formula Ib is realized when n is 1, $R^3$ and $R^4$ are both hydrogen or one of $R^3$ and $R^4$ is hydrogen and the other is methyl, and up to 2 $R^{a2}$ are selected from the group consisting of methyl, ethyl, fluorine, chlorine, OH, CN, $(CH_2)_nCF_3$, $C_{2-4}$ alkynyl, $(CH_2)_n$pyridyl, methxoxy, $SO_2Me$, $(CH_2)_n$phenyl, pyrazolyl, said methyl, ethyl, phenyl, pyrazolyl and pyridyl when possible optionally substituted with 1 to 3 groups of $R^b$ selected from the group consisting of methyl, ethyl, methoxy, $C_{2-4}$alkenyl and $SO_2Me$. Still another subembodiment of formula Ib is realized when A is selected from the group consisting of cyclohexyl, pyranyl, hydroxycyclohexyl, hydroxypyranyl, n is 0 or 1, X is CH. $X^1$ is CH. or N, up to 2 $R^{a2}$ are selected from the group consisting of methyl, ethyl, propyl, butyl, fluorine, chlorine, bromine, —O—, OH, CN, $(CH_2)_nCF_3$, $CH_2F$, $C_{2-4}$ alkenyl, $C_{2-4}$ alkynyl, $C_{2-4}$ alkynylphenyl, $(CH_2)_n$pyridyl, methxoxy, $SO_2Me$, COOEt, cyclopropyl, $(CH_2)_n$phenyl, pyrimidinyl, pyrazinyl, pyridazinyl, benzypiperidinyl, pyrazolyl, benzothiazolyl, quinolinyl, or two adjacent $R^{a2}$ groups combine to form benzotetrahydrofuranyl, oxetanyl, said alkyl, aryl and heterocyclyl groups of $R^{a2}$ when possible optionally substituted with 1 to 3 groups of $R^b$, and $R^3$ and $R^4$ are both hydrogen or one of $R^3$ and $R^4$ is hydrogen and the other is methyl. Yet another subembodiment of formula Ib is realized when A is selected from the group consisting of cyclohexyl, pyranyl, hydroxycyclohexyl, hydroxypyranyl, n is 0 or 1, X is N, $X^1$ is CH. or N, $R^{a2}$ is 0-2 and is selected from the group consisting of methyl, ethyl, propyl, butyl, fluorine, chlorine, bromine, —O—, OH, CN, $(CH_2)_nCF_3$, $CH_2F$, $C_{2-4}$ alkenyl, $C_{2-4}$ alkynyl, $C_{2-4}$ alkynylphenyl, $(CH_2)_n$pyridyl, methxoxy, $SO_2Me$, COOEt, cyclopropyl, $(CH_2)_n$phenyl, pyrimidinyl, pyrazinyl, pyridazinyl, benzypiperidinyl, pyrazolyl, benzothiazolyl, quinolinyl, or two adjacent $R^{a2}$ groups combine to form benzotetrahydrofuranyl, oxetanyl, said alkyl, aryl and heterocyclyl groups of $R^{a2}$ optionally substituted with 1 to 3 groups of $R^b$, and $R^3$ and $R^4$ are both hydrogen or one of $R^3$ and $R^4$ is hydrogen and the other is methyl.

Another subembodiment of formula Ib is represented by structural formula Ib' or Ib":

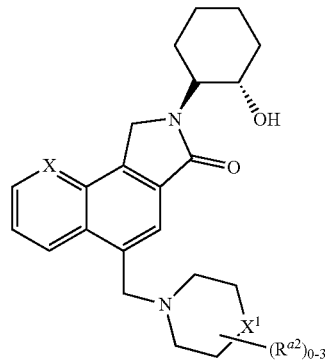

Ib'

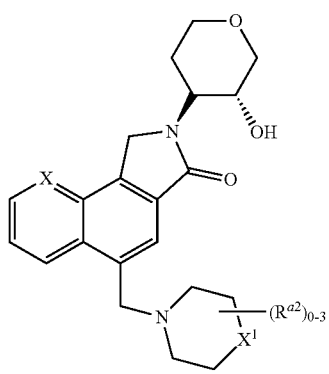

Ib"

wherein X, $X^1$ and $R^{a2}$ is as originally described. Still another subembodiment of formula Ib is represented by structural formula Ib''' or Ib'''':

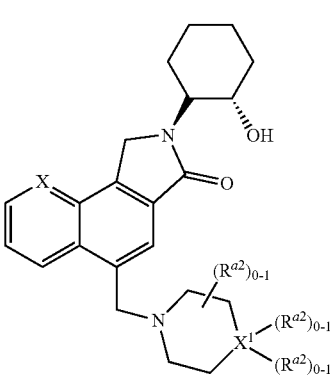

Ib'''

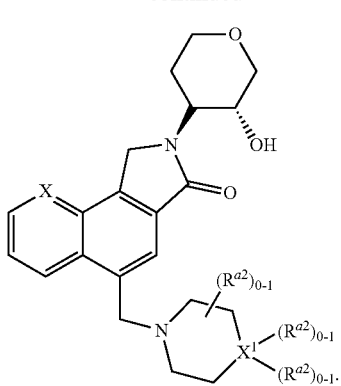

In yet another embodiment the invention is directed to methods of treating a patient (preferably a human) for diseases in which the M1 receptor is involved, such as Alzheimer's Disease, cognitive impairment, schizophrenia, pain disorders and sleep disorders, by administering to the patient a therapeutically effective amount of a compound of general formula (I).

The invention is also directed to the use of a compound of formula (I) for treating diseases or disorders in which the M1 receptor is involved, such as Alzheimer's disease, cognitive impairment, schizophrenia, pain disorders and sleep disorders.

The invention is also directed to medicaments or pharmaceutical compositions for treating diseases or disorders in which the M1 receptor is involved, such as Alzheimer's disease, cognitive impairment, schizophrenia, pain disorders and sleep disorders, which comprise a compound of formula (I), or a pharmaceutically acceptable salt thereof, and a pharmaceutically acceptable carrier.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, comprising combining a compound of formula (I) with one or more pharmaceutically acceptable carriers.

Specific examples of the compounds of formula (I) are:
1-({2-[(1S,2S)-2-hydroxycyclohexyl]-3-oxo-2,3-dihydro-1H-benzo[e]isoindol-5-yl}methyl)-4-(pyridine-2-yl)piperidine-4-carbonitrile,
5-{[4-Fluoro-4-(pyridine-2-yl)piperidine-1-yl]methyl}-2-[(1S,2S)-2-hydroxycyclohexyl]-1,2-dihydro-3H-benzo[e]isoindol-3-one,
1-({2-[(1S,2S)-2-Hydroxycyclohexyl]-1-methyl-3-oxo-2,3-dihydro-1H-benzo[e]isoindol-5-yl}methyl)-4-(pyridine-2-yl)piperidine-4-carbonitrile,
1-({2-[(1S,2S)-2-Hydroxycyclohexyl]-3-oxo-2,3-dihydro-1H-benzo[e]isoindol-5-yl}methyl)-4-(6-methylpyridin-2-yl)piperidine-4-carbonitrile,
4-(6-Ethylpyridin-2-yl)-1-({2-[(1S,2S)-hydroxycyclohexyl]-3-oxo-2,3-dihydro-1H-benzo[e]isoindol-5-yl}methyl)piperidine-4-carbonitrile,
1-({2-[(1S,2S)-2-Hydroxycyclohexyl]-3-oxo-2,3-dihydro-1H-benzo[e]isoindol-5-yl}methyl)-4-(6-methoxypyridin-2-yl)piperidine-4-carbonitrile,
1,5-Anhydro-2,3-dideoxy-3-{5-[(4,4-difluoropiperidin-1-yl)methyl]-7-oxo-7,9-dihydro-8H-pyrrolo[3,4-h]quinolin-8-yl}-L-threo-pentitol,
1,5-Anhydro-2,4-dideoxy-2-{5-[(4,4-difluoropiperidin-1-yl)methyl]-7-oxo-7,9-dihydro-8H-pyrrolo[3,4-h]quinolin-8-yl}-L-threo-pentitol,
5-[(4-Ethenyl-4-fluoropiperidin-1-yl)methyl]-8-[(1S,2S)-2-hydroxycyclohexyl]-8,9-dihydro-7H-pyrrolo[3,4-h]quinolin-7-one,
3-{5-[(4,4-Difluoropiperidin-1-yl)methyl]-7-oxo-7,9-dihydro-8H-pyrrolo[3,4-h]quinolin-8-yl}phenyl dimethylcarbamate,
2-(2-Hydroxycyclohexyl)-5-(piperidin-1-ylmethyl)-1,2-dihydro-3H-benzo[e]isoindol-3-one,
2-[(1S,2S)-2-hydroxycyclohexyl]-5-[(4-methylpiperazin-1-yl)methyl]-1,2-dihydro-3H-benzo[e]isoindol-3-one,
2-[(1S,2S)-2-hydroxycyclohexyl]-5-[(4-methyl-3-oxopiperazin-1-yl)methyl]-1,2-dihydro-3H-benzo[e]isoindol-3-one,
5-[(4-acetylpiperazin-1-yl)methyl]-2-(2-hydroxycyclohexyl)-1,2-dihydro-3H-benzo[e]isoindol-3-one,
2-(2-hydroxycyclohexyl)-5-{[4-(methylsulfonyl)piperazin-1-yl]methyl}-1,2-dihydro-3H-benzo[e]isoindol-3-one,
2-(2-hydroxycyclohexyl)-5-[(3-methylpiperidin-1-yl)methyl]-1,2-dihydro-3H-benzo[e]isoindol-3-one,
5-[(3-fluoropiperidin-1-yl)methyl]-2-(2-hydroxycyclohexyl)-1,2-dihydro-3H-benzo[e]isoindol-3-one,
5-[(3,3-difluoropiperidin-1-yl)methyl]-2-(2-hydroxycyclohexyl)-1,2-dihydro-3H-benzo[e]isoindol-3-one,
4-fluoro-1-({2-[(1S,2S)-2-hydroxycyclohexyl]-3-oxo-2,3-dihydro-1H-benzo[e]isoindol-5-yl}methyl)piperidine-4-carbonitrile,
1-({2-[(1S,2S)-2-hydroxycyclohexyl]-3-oxo-2,3-dihydro-1H-benzo[e]isoindol-5-yl}methyl)piperidine-4-carbonitrile,
2-[(1S,2S)-2-hydroxycyclohexyl]-5-[(4-methylpiperidin-1-yl)methyl]-1,2-dihydro-3H-benzo[e]isoindol-3-one,
2-(2-hydroxycyclohexyl)-5-[(4-hydroxypiperidin-1-yl)methyl]-1,2-dihydro-3H-benzo[e]isoindol-3-one,
2-(2-Hydroxycyclohexyl)-5-(pyrrolidin-1-ylmethyl)-1,2-dihydro-3H-benzo[e]isoindol-3-one,
2-(2-hydroxycyclohexyl)-5-(morpholin-4-ylmethyl)-1,2-dihydro-3H-benzo[e]isoindol-3-one,
5-[(4,4-difluoropiperidin-1-yl)methyl]-2-(2-hydroxycyclohexyl)-1,2-dihydro-3H-benzo[e]isoindol-3-one,
5-[(4-fluoropiperidin-1-yl)methyl]-2-(2-hydroxycyclohexyl)-1,2-dihydro-3H-benzo[e]isoindol-3-one,
2-(2-hydroxycyclohexyl)-5-{[4-(trifluoromethyl)piperidin-1-yl]methyl}-1,2-dihydro-3H-benzo[e]isoindol-3-one,
5-[(3-fluoro-4-hydroxypyrrolidin-1-yl)methyl]-2-(2-hydroxycyclohexyl)-1,2-dihydro-3H-benzo[e]isoindol-3-one,
5-{[trans-3,4-difluoropyrrolidin-1-yl]methyl}-2-(2-hydroxycyclohexyl)-1,2-dihydro-3H-benzo[e]isoindol-3-one,
2-(2-hydroxycyclohexyl)-5-{[2-(trifluoromethyl)pyrrolidin-1-yl]methyl}-1,2-dihydro-3H-benzo[e]isoindol-3-one,
5-{[3-(fluoromethyl)pyrrolidin-1-yl]methyl}-2-(2-hydroxycyclohexyl)-1,2-dihydro-3H-benzo[e]isoindol-3-one,
5-{[(3S)-3-fluoropyrrolidin-1-yl]methyl}-2-(2-hydroxycyclohexyl)-1,2-dihydro-3H-benzo[e]isoindol-3-one,
5-[(3,3-difluoropyrrolidin-1-yl)methyl]-2-(2-hydroxycyclohexyl)-1,2-dihydro-3H-benzo[e]isoindol-3-one,
2-(2-hydroxycyclohexyl)-5-{[4-(2,2,2-trifluoroethyl)piperazin-1-yl]methyl}-1,2-dihydro-3H-benzo[e]isoindol-3-one,
ethyl 4-fluoro-1-{[2-(2-hydroxycyclohexyl)-3-oxo-2,3-dihydro-1H-benzo[e]isoindol-5-yl]methyl}piperidine-4-carboxylate, 2-(2-hydroxycyclohexyl)-5-(2-oxa-7-azaspiro[3.5]non-7-yl-methyl)-1,2-dihydro-3H-benzo[e]isoindol-3-one,
2-(2-hydroxycyclohexyl)-5-[(4-hydroxy-4-methylpiperidin-1-yl)methyl]-1,2-dihydro-3H-benzo[e]isoindol-3-one,
5-[(4,4-dimethylpiperidin-1-yl)methyl]-2-(2-hydroxycyclohexyl)-1,2-dihydro-3H-benzo[e]isoindol-3-one,
5-[(4-cyclopropylpiperidin-1-yl)methyl]-2-(2-hydroxycyclohexyl)-1,2-dihydro-3H-benzo[e]isoindol-3-one,
2-(2-hydroxycyclohexyl)-5-(1'H-spiro[1-benzofuran-3,4'-piperidin]-1'-ylmethyl)-1,2-dihydro-3H-benzo[e]isoindol-3-one,
2-(2-hydroxycyclohexyl)-5-[(4-phenylpiperidin-1-yl)methyl]-1,2-dihydro-3H-benzo[e]isoindol-3-one,
2-(2-hydroxycyclohexyl)-5-[(4-(4-pyridinyl)piperidin-1-yl)methyl]-1,2-dihydro-3H-benzo[e]isoindol-3-one,
2-(2-hydroxycyclohexyl)-5-[(4-hydroxy-4-pyridin-4-ylpiperidin-1-yl)methyl]-1,2-dihydro-3H-benzo[e]isoindol-3-one,
1-({2-[(1S,2S)-2-hydroxycyclohexyl]-1-methyl-3-oxo-2,3-dihydro-1H-benzo[e]isoindol-5-yl}methyl)-4-(pyridin-2-yl)piperidine-4-carbonitrile,
1-({2-[(1R,2R)-2-hydroxycyclohexyl]-3-oxo-2,3-dihydro-1H-benzo[e]isoindol-5-yl}methyl)-4-pyridin-2-ylpiperidine-4-carbonitrile,
1-({2-[(1R,2S)-2-hydroxycyclohexyl]-3-oxo-2,3-dihydro-1H-benzo[e]isoindol-5-yl}methyl)-4-pyridin-2-ylpiperidine-4-carbonitrile,
4-(6-chloropyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile, 4-(6-ethenylpyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile,
4-(6-ethenylpyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile,
1-({2-[(1S,2S)-2-hydroxycyclohexyl]-3-oxo-2,3-dihydro-1H-benzo[e]isoindol-5-yl}methyl)-4-(pyrazin-2-yl)piperidine-4-carbonitrile,
1-({2-[(1S,2S)-2-hydroxycyclohexyl]-3-oxo-2,3-dihydro-1H-benzo[e]isoindol-5-yl}methyl)-4-(pyrimidin-4-yl)piperidine-4-carbonitrile,
1-({2-[(1S,2S)-2-hydroxycyclohexyl]-3-oxo-2,3-dihydro-1H-benzo[e]isoindol-5-yl}methyl)-4-(pyridazin-3-yl)piperidine-4-carbonitrile, 5-[(4-fluoro-4-phenylpiperidin-1-yl)methyl]-2-[(1R,2R)-2-hydroxycyclohexyl]-1,2-dihydro-3H-benzo[e]isoindol-3-one,
1-{[3-oxo-2-(tetrahydro-2H-pyran-4-yl)-2,3-dihydro-1H-benzo[e]isoindol-5-yl]methyl}-4-pyridin-2-ylpiperidine-4-carbonitrile,
1-{[3-oxo-2-(tetrahydro-2H-pyran-3-yl)-2,3-dihydro-1H-benzo[e]isoindol-5-yl]methyl}-4-pyridin-2-ylpiperidine-4-carbonitrile,
1-({2-[(1S,2S)-2-hydroxycyclohexyl]-3-oxo-2,3-dihydro-1H-benzo[e]isoindol-5-yl}methyl)-4-phenylpiperidine-4-carbonitrile,
1-({2-[(1S,2S)-2-hydroxycyclohexyl]-3-oxo-2,3-dihydro-1H-benzo[e]isoindol-5-yl}methyl)-4-pyridin-3-ylpiperidine-4-carbonitrile,
1-({2-[(1S,2S)-2-hydroxycyclohexyl]-3-oxo-2,3-dihydro-1H-benzo[e]isoindol-5-yl}methyl)-4-pyridin-4-ylpiperidine-4-carbonitrile,
4-(2-chlorophenyl)-1-({2-[(1S,2S)-2-hydroxycyclohexyl]-3-oxo-2,3-dihydro-1H-benzo[e]isoindol-5-yl}methyl)piperidine-4-carbonitrile,
4-(2-fluorophenyl)-1-({2-[(1R,2S)-2-hydroxycyclohexyl]-3-oxo-2,3-dihydro-1H-benzo[e]isoindol-5-yl}methyl)piperidine-4-carbonitrile,
1-({2-[(1R,2S)-2-hydroxycyclohexyl]-3-oxo-2,3-dihydro-1H-benzo[e]isoindol-5-yl}methyl)-4-(2-methylphenyl)piperidine-4-carbonitrile,
1-{[2-(2-fluorophenyl)-3-oxo-2,3-dihydro-1H-benzo[e]isoindol-5-yl]methyl}-4-pyridin-2-ylpiperidine-4-carbonitrile,
1-({2-[(1S,2S)-2-hydroxycyclohexyl]-3-oxo-2,3-dihydro-1H-benzo[e]isoindol-5-yl}methyl)-4-(4-methylpyridin-2-yl)piperidine-4-carbonitrile,
5-{[4-(4-fluorophenyl)piperazin-1-yl]methyl}-2-[(1S,2S)-2-hydroxycyclohexyl]-1,2-dihydro-3H-benzo[e]isoindol-3-one,
2-[(1S,2S)-2-hydroxycyclohexyl]-5-{[4-(methylsulfonyl)phenyl]piperazin-1-yl}methyl)-1,2-dihydro-3H-benzo[e]isoindol-3-one,
2-[(1S,2S)-2-hydroxycyclohexyl]-5-{[4-(4-methoxyphenyl)piperazin-1-yl]methyl}-1,2-dihydro-3H-benzo[e]isoindol-3-one,
2-[(1S,2S)-2-hydroxycyclohexyl]-5-{[4-(4-methoxyphenyl)-2-methylpiperazin-1-yl]methyl}-1,2-dihydro-3H-benzo[e]isoindol-3-one,
2-[(1S,2S)-2-hydroxycyclohexyl]-5-{[5-(4-methoxyphenyl)-2,5-diazabicyclo[2.2.1]hept-2-yl]methyl}-1,2-dihydro-3H-benzo[e]isoindol-3-one,
2-[(1S,2S)-2-hydroxycyclohexyl]-5-[(4-phenylpiperazin-1-yl)methyl]-1,2-dihydro-3H-benzo[e]isoindol-3-one,
2-[(1R,2S)-2-hydroxycyclohexyl]-1-methyl-5-[(4-phenylpiperazin-1-yl)methyl]-1,2-dihydro-3H-benzo[e]isoindol-3-one,
2-[(1S,2S)-2-hydroxycyclohexyl]-5-[(4-pyridin-2-ylpiperazin-1-yl)methyl]-1,2-dihydro-3H-benzo[e]isoindol-3-one,
2-[(1S,2S)-2-hydroxycyclohexyl]-5-[(4-pyridin-3-ylpiperazin-1-yl)methyl]-1,2-dihydro-3H-benzo[e]isoindol-3-one,
2-[(1S,2S)-2-hydroxycyclohexyl]-5-[(4-pyridin-4-ylpiperazin-1-yl)methyl]-1,2-dihydro-3H-benzo[e]isoindol-3-one,
2-[(1S,2S)-2-hydroxycyclohexyl]-5-[(3-methyl-4-phenylpiperazin-1-yl)methyl]-1,2-dihydro-3H-benzo[e]isoindol-3-one,
2-[(1S,2S)-2-hydroxycyclohexyl]-5-{[4-(1-methyl-1H-pyrazol-4-yl)piperazin-1-yl]methyl}-1,2-dihydro-3H-benzo[e]isoindol-3-one,
2-[(1S,2S)-2-hydroxycyclohexyl]-5-{[4-(1-methyl-1H-pyrazol-4-yl)piperazin-1-yl]methyl}-1,2-dihydro-3H-benzo[e]isoindol-3-one,
2-[(1R,2R)-2-hydroxycyclohexyl]-5-{[4-(1-methyl-1H-pyrazol-4-yl)piperazin-1-yl]methyl}-1,2-dihydro-3H-benzo[e]isoindol-3-one,
5-{[4-(1-methyl-1H-pyrazol-4-yl)piperazin-1-yl]methyl}-2-(tetrahydro-2H-pyran-4-yl)-1,2-dihydro-3H-benzo[e]isoindol-3-one,
5-{[4-(1-methyl-1H-pyrazol-4-yl)piperazin-1-yl]methyl}-2-(tetrahydro-2H-pyran-3-yl)-1,2-dihydro-3H-benzo[e]isoindol-3-one,
2-(2-fluorophenyl)-5-[(4-isoquinolin-3-ylpiperazin-1-yl)methyl]-1,2-dihydro-3H-benzo[e]isoindol-3-one,
5-{[4-(1,3-benzothiazol-6-yl)piperazin-1-yl]methyl}-2-(2-fluorophenyl)-1,2-dihydro-3H-benzo[e]isoindol-3-one,
8-[(1S,2S)-2-hydroxycyclohexyl]-5-(piperidin-1-ylmethyl)-8,9-dihydro-7H-pyrrolo[3,4-h]quinolin-7-one,
8-[(1S,2S)-2-hydroxycyclohexyl]-5-[(4-methylpiperidin-1-yl)methyl]-8,9-dihydro-7H-pyrrolo[3,4-h]quinolin-7-one, 5-[(diethylamino)methyl]-8-(2-hydroxycyclohexyl)-8,9-dihydro-7H-pyrrolo[3,4-h]quinolin-7-one, 8-(2-hydroxycyclohexyl)-5-[(4-hydroxypiperidin-1-yl)methyl]-8,9-dihydro-7H-pyrrolo[3,4-h]quinolin-7-one, 5-[(4-cyclopropylpiperidin-1-yl)methyl]-8-(2-hydroxycyclohexyl)-8,9-dihydro-7H-pyrrolo[3,4-h]quinolin-7-one, 5-[(4-fluoropiperidin-1-yl)methyl]-8-(2-hydroxycyclohexyl)-8,9-dihydro-7H-pyrrolo[3,4-h]quinolin-7-one, 1-({8-[(1S,2S)-2-hydroxycyclohexyl]-7-oxo-8,9-dihydro-7H-pyrrolo[3,4-h]quinolin-5-yl}methyl)piperidine-4-carbonitrile, 5-[(4-fluoropiperidin-1-yl)methyl]-8-[(1S,2S)-2-hydroxycyclohexyl]-9-methyl-8,9-dihydro-7H-pyrrolo[3,4-h]quinolin-7-one, 1-({8-[(1S,2S)-2-hydroxycyclohexyl]-7-oxo-8,9-dihydro-7H-pyrrolo[3,4-h]quinolin-5-yl}methyl)piperidine-4-carbonitrile, 8-(2-hydroxycyclohexyl)-5-(1'H-spiro[1-benzofuran-3,4'-piperidin]-1'-ylmethyl)-8,9-dihydro-7H-pyrrolo[3,4-h]quinolin-7-one, 8-(2-hydroxycyclohexyl)-5-(2-oxa-7-azaspiro[3.5]non-7-ylmethyl)-8,9-dihydro-7H-pyrrolo[3,4-h]quinolin-7-one, 8-(2-hydroxycyclohexyl)-5-(pyrrolidin-1-ylmethyl)-8,9-dihydro-7H-pyrrolo[3,4-h]quinolin-7-one, 5-[(3,3-difluoropyrrolidin-1-yl)methyl]-8-(2-hydroxycyclohexyl)-8,9-dihydro-7H-pyrrolo[3,4-h]quinolin-7-one, 8-(2-hydroxycyclohexyl)-5-(morpholin-4-ylmethyl)-8,9-dihydro-7H-pyrrolo[3,4-h]quinolin-7-one, 5-[(4,4-dimethylpiperidin-1-yl)methyl]-8-(2-hydroxycyclohexyl)-8,9-dihydro-7H-pyrrolo[3,4-h]quinolin-7-one.

8-(2-hydroxycyclohexyl)-5-[(4-hydroxy-4-methylpiperidin-1-yl)methyl]-8,9-dihydro-7H-pyrrolo[3,4-h]quinolin-7-one, 5-[(4-fluoro-4-methylpiperidin-1-yl)methyl]-8-[(1S,2S)-2-hydroxycyclohexyl]-8,9-dihydro-7H-pyrrolo[3,4-h]quinolin-7-one, 5-[(4-ethynyl-4-fluoropiperidin-1-yl)methyl]-8-[(1S,2S)-2-hydroxycyclohexyl]-8,9-dihydro-7H-pyrrolo[3,4-h]quinolin-7-one, 5-[(4,4-difluoropiperidin-1-yl)methyl]-8-[(1R,2S)-2-hydroxycyclohexyl]-9-methyl-8,9-dihydro-7H-pyrrolo[3,4-h]quinolin-7-one, 5-[(4,4-difluoropiperidin-1-yl)methyl]-9-ethyl-8-[(1R,2S)-2-hydroxycyclohexyl]-8,9-dihydro-7H-pyrrolo[3,4-h]quinolin-7-one, 1,5-anhydro-2,4-dideoxy-4-{5-[(4,4-difluoropiperidin-1-yl)methyl]-9-methyl-7-oxo-7,9-dihydro-8H-pyrrolo[3,4-h]quinolin-8-yl}-D-erythro-pentitol, 1,5-anhydro-3,4-dideoxy-3-{5-[(4,4-difluoropiperidin-1-yl)methyl]-9-methyl-7-oxo-7,9-dihydro-8H-pyrrolo[3,4-h]quinolin-8-yl}-D-erythro-pentitol, 1,5-anhydro-3-{5-[(4-cyano-4-pyridin-2-ylpiperidin-1-yl)methyl]-9-methyl-7-oxo-7,9-dihydro-8H-pyrrolo[3,4-h]quinolin-8-yl}-2,3-dideoxypentitol, 1,5-anhydro-3-(5-{[4-cyano-4-(4-methylpyridin-2-yl)piperidin-1-yl]methyl}-9-methyl-7-oxo-7,9-dihydro-8H-pyrrolo[3,4-h]quinolin-8-yl)-2,3-dideoxypentitol, 1,5-anhydro-3-{5-[(4-cyano-4-fluoropiperidin-1-yl)methyl]-9-methyl-7-oxo-7,9-dihydro-8H-pyrrolo[3,4-h]quinolin-8-yl}-2,3-dideoxypentitol, 1,5-anhydro-3-{5-[(4-fluoropiperidin-1-yl)methyl]-9-methyl-7-oxo-7,9-dihydro-8H-pyrrolo[3,4-h]quinolin-8-yl}-2,3-dideoxypentitol, 1,5-anhydro-3-{5-[(4-cyanopiperidin-1-yl)methyl]-9-methyl-7-oxo-7,9-dihydro-8H-pyrrolo[3,4-h]quinolin-8-yl}-2,3-dideoxypentitol, 1,5-anhydro-2,3-dideoxy-3-{5-[(4-ethynylpiperidin-1-yl)methyl]-9-methyl-7-oxo-7,9-dihydro-8H-pyrrolo[3,4-h]quinolin-8-yl}pentitol, 1,5-anhydro-2,3-dideoxy-3-{5-[(4-ethynyl-4-fluoropiperidin-1-yl)methyl]-9-methyl-7-oxo-7,9-dihydro-8H-pyrrolo[3,4-h]quinolin-8-yl}pentitol, 1,5-anhydro-2,3-dideoxy-3-{5-[(4-fluoro-4-prop-1-yn-1-ylpiperidin-1-yl)methyl]-9-methyl-7-oxo-7,9-dihydro-8H-pyrrolo[3,4-h]quinolin-8-yl}pentitol, 5-[(4,4-difluoropiperidin-1-yl)methyl]-8-(2-hydroxycyclohexyl)-8,9-dihydro-7H-pyrrolo[3,4-h]quinolin-7-one, 4-fluoro-1-({8-[(1S,2S)-2-hydroxycyclohexyl]-7-oxo-8,9-dihydro-7H-pyrrolo[3,4-h]quinolin-5-yl}methyl)piperidine-4-carbonitrile, 4-fluoro-1-{[8-(2-hydroxycyclohexyl)-9-methyl-7-oxo-8,9-dihydro-7H-pyrrolo[3,4-h]quinolin-5-yl]methyl}piperidine-4-carbonitrile, 4-fluoro-1-{[8-(2-hydroxycyclohexyl)-9-methyl-7-oxo-8,9-dihydro-7H-pyrrolo[3,4-h]quinolin-5-yl]methyl}piperidine-4-carbonitrile, 1-({9-ethyl-8-[(1R,2S)-2-hydroxycyclohexyl]-7-oxo-8,9-dihydro-7H-pyrrolo[3,4-h]quinolin-5-yl}methyl)-4-fluoropiperidine-4-carbonitrile, 5-[(3-fluoropiperidin-1-yl)methyl]-8-(2-hydroxycyclohexyl)-8,9-dihydro-7H-pyrrolo[3,4-h]quinolin-7-one, 5-[(3,3-difluoropiperidin-1-yl)methyl]-8-(2-hydroxycyclohexyl)-8,9-dihydro-7H-pyrrolo[3,4-h]quinolin-7-one, 8-(2-hydroxycyclohexyl)-5-{[4-(trifluoromethyl)piperidin-1-yl]methyl}-8,9-dihydro-7H-pyrrolo[3,4-h]quinolin-7-one, 5-[(4-ethynylpiperidin-1-yl)methyl]-8-(2-hydroxycyclohexyl)-8,9-dihydro-7H-pyrrolo[3,4-h]quinolin-7-one, 5-[(4-fluoro-4-pent-1-yn-1-ylpiperidin-1-yl)methyl]-8-[(1S,2S)-2-hydroxycyclohexyl]-8,9-dihydro-7H-pyrrolo[3,4-h]quinolin-7-one, 4-fluoro-1-{[8-(3-hydroxyphenyl)-7-oxo-8,9-dihydro-7H-pyrrolo[3,4-h]quinolin-5-yl]methyl}piperidine-4-carbonitrile, 5-[(4-ethynyl-4-fluoropiperidin-1-yl)methyl]-8-(3-hydroxyphenyl)-8,9-dihydro-7H-pyrrolo[3,4-h]quinolin-7-one, 3-{5-[(4-cyano-4-fluoropiperidin-1-yl)methyl]-7-oxo-7,9-dihydro-8H-pyrrolo[3,4-h]quinolin-8-yl}phenyl dimethylcarbamate, 3-{5-[(4-ethynyl-4-fluoropiperidin-1-yl)methyl]-7-oxo-7,9-dihydro-8H-pyrrolo[3,4-h]quinolin-8-yl}phenyl dimethylcarbamate, 5-[(4-fluoro-4-prop-1-yn-1-ylpiperidin-1-yl)methyl]-8-[(1S,2S)-2-hydroxycyclohexyl]-8,9-dihydro-7H-pyrrolo[3,4-h]quinolin-7-one, 5-{[4-(cyclopropylethynyl)-4-fluoropiperidin-1-yl]methyl}-8-[(1S,2S)-2-hydroxycyclo-hexyl]-8,9-dihydro-7H-pyrrolo[3,4-h]quinolin-7-one, 5-({4-fluoro-4-[(4-fluorophenyl)ethynyl]piperidin-1-yl}methyl)-8-(2-hydroxycyclo-hexyl)-8,9-dihydro-7H-pyrrolo[3,4-h]quinolin-7-one, 5-[(4-benzyl-4-fluoropiperidin-1-yl)methyl]-8-(2-hydroxycyclohexyl)-8,9-dihydro-7H-pyrrolo[3,4-h]quinolin-7-one, 1-{[8-(2-hydroxycyclohexyl)-7-oxo-8,9-dihydro-7H-pyrrolo[3,4-h]quinolin-5-yl]methyl}-4-(pyridin-4-ylmethyl)piperidine-4-carbonitrile, 1-{8-[(1S,2S)-2-hydroxycyclohexyl]-7-oxo-8,9-dihydro-7H-pyrrolo[3,4-h]quinolin-5-yl}methyl)-4-phenylpiperidine-4-carbonitrile, 1-{[8-(2-hydroxycyclohexyl)-9-methyl-7-oxo-8,9-dihydro-7H-pyrrolo[3,4-h]quinolin-5-yl]methyl}-4-phenylpiperidine-4-carbonitrile, 8-(2-hydroxycyclohexyl)-5-[(4-phenylpiperidin-1-yl)methyl]-8,9-dihydro-7H-pyrrolo[3,4-h]quinolin-7-one,
8-(2-hydroxycyclohexyl)-9-methyl-5-[(4-phenylpiperidin-1-yl)methyl]-8,9-dihydro-7H-pyrrolo[3,4-h]quinolin-7-one,
8-(2-hydroxycyclohexyl)-5-[(4-pyridin-4-ylpiperidin-1-yl)methyl]-8,9-dihydro-7H-pyrrolo[3,4-h]quinolin-7-one,
8-(2-hydroxycyclohexyl)-5-[(4-hydroxy-4-pyridin-4-ylpiperidin-1-yl)methyl]-8,9-dihydro-7H-pyrrolo[3,4-h]quinolin-7-one,
8-(2-hydroxycyclohexyl)-9-methyl-5-[(4-pyridin-4-ylpiperidin-1-yl)methyl]-8,9-dihydro-7H-pyrrolo[3,4-h]quinolin-7-one,
1-({8-[(1S,2S)-2-hydroxycyclohexyl]-7-oxo-8,9-dihydro-7H-pyrrolo[3,4-h]quinolin-5-yl}methyl)-4-pyridin-2-ylpiperidine-4-carbonitrile,
5-[(4-fluoro-4-pyridin-2-ylpiperidin-1-yl)methyl]-8-(2-hydroxycyclohexyl)-8,9-dihydro-7H-pyrrolo[3,4-h]quinolin-7-one,
5-[(4-fluoro-4-pyridin-2-ylpiperidin-1-yl)methyl]-8-[(1R,2S)-2-hydroxycyclohexyl]-9-methyl-8,9-dihydro-7H-pyrrolo[3,4-h]quinolin-7-one,
1-{[8-(2-hydroxycyclohexyl)-7-oxo-8,9-dihydro-7H-pyrrolo[3,4-h]quinolin-5-yl]methyl}-4-(4-methylpyridin-2-yl)piperidine-4-carbonitrile,
1-({(9R)-8-[(1S,2S)-2-hydroxycyclohexyl]-9-methyl-7-oxo-8,9-dihydro-7H-pyrrolo[3,4-h]quinolin-5-yl}methyl)-4-pyridin-2-ylpiperidine-4-carbonitrile,
1-({(9R)-8-[(1S,2S)-2-hydroxycyclohexyl]-9-methyl-7-oxo-8,9-dihydro-7H-pyrrolo[3,4-h]quinolin-5-yl}methyl)-4-pyridin-2-ylpiperidine-4-carbonitrile,
1-({(9R)-8-[(1S,2S)-2-hydroxycyclohexyl]-9-methyl-7-oxo-8,9-dihydro-7H-pyrrolo[3,4-h]quinolin-5-yl}methyl)-4-(4-methylpyridin-2-yl)piperidine-4-carbonitrile,
1-({(9R)-8-[(1S,2S)-2-hydroxycyclohexyl]-9-methyl-7-oxo-8,9-dihydro-7H-pyrrolo[3,4-h]quinolin-5-yl}methyl)-4-(4-methylpyridin-2-yl)piperidine-4-carbonitrile,
(9R)-5-[(4-fluoro-4-pyridin-2-ylpiperidin-1-yl)methyl]-8-[(1S,2S)-2-hydroxycyclohexyl]-9-methyl-8,9-dihydro-7H-pyrrolo[3,4-h]quinolin-7-one,
1-({8-[(1S,2S)-2-hydroxycyclohexyl]-7-oxo-8,9-dihydro-7H-pyrrolo[3,4-h]quinolin-5-yl}methyl)-4-(6-methoxypyridin-2-yl)piperidine-4-carbonitrile,
1-({8-[(1S,2S)-2-hydroxycyclohexyl]-7-oxo-8,9-dihydro-7H-pyrrolo[3,4-h]quinolin-5-yl}methyl)-4-(6-methoxypyridin-2-yl)piperidine-4-carbonitrile,
1-({8-[(1S,2S)-2-hydroxycyclohexyl]-7-oxo-8,9-dihydro-7H-pyrrolo[3,4-h]quinolin-5-yl}methyl)-4-(6-methoxypyridin-2-yl)piperidine-4-carbonitrile,
8-[(1S,2S)-2-hydroxycyclohexyl]-5-{[4-(1-methyl-1H-pyrazol-4-yl)piperazin-1-yl]methyl}-8,9-dihydro-7H-pyrrolo[3,4-h]quinolin-7-one,
8-(2-hydroxycyclohexyl)-9-methyl-5-{[4-(1-methyl-1H-pyrazol-4-yl)piperazin-1-yl]methyl}-8,9-dihydro-7H-pyrrolo[3,4-h]quinolin-7-one,
8-(2-hydroxycyclohexyl)-5-[(4-pyridin-4-ylpiperazin-1-yl)methyl]-8,9-dihydro-7H-pyrrolo[3,4-h]quinolin-7-one,
8-(2-hydroxycyclohexyl)-9-methyl-5-[(4-pyridin-4-ylpiperidin-1-yl)methyl]-8,9-dihydro-7H-pyrrolo[3,4-h]quinolin-7-one,
8-(2-hydroxycyclohexyl)-5-[(4-pyridin-3-ylpiperazin-1-yl)methyl]-8,9-dihydro-7H-pyrrolo[3,4-h]quinolin-7-one,
8-(2-hydroxycyclohexyl)-9-methyl-5-[(4-pyridin-3-ylpiperazin-1-yl)methyl]-8,9-dihydro-7H-pyrrolo[3,4-h]quinolin-7-one,
8-(2-hydroxycyclohexyl)-9-methyl-5-[(4-pyridin-3-ylpiperazin-1-yl)methyl]-8,9-dihydro-7H-pyrrolo[3,4-h]quinolin-7-one,
8-(2-hydroxycyclohexyl)-5-[(4-pyridin-2-ylpiperazin-1-yl)methyl]-8,9-dihydro-7H-pyrrolo[3,4-h]quinolin-7-one,
8-(2-hydroxycyclohexyl)-9-methyl-5-[(4-pyridin-2-ylpiperazin-1-yl)methyl]-8,9-dihydro-7H-pyrrolo[3,4-h]quinolin-7-one,
8-(2-hydroxycyclohexyl)-9-methyl-5-[(4-pyridin-2-ylpiperazin-1-yl)methyl]-8,9-dihydro-7H-pyrrolo[3,4-h]quinolin-7-one,
8-(2-hydroxycyclohexyl)-5-{[4-(4-methoxyphenyl)piperazin-1-yl]methyl}-8,9-dihydro-7H-pyrrolo[3,4-h]quinolin-7-one,
8-(2-hydroxycyclohexyl)-5-{[4-(4-methoxyphenyl)piperazin-1-yl]methyl}-9-methyl-8,9-dihydro-7H-pyrrolo[3,4-h]quinolin-7-one,
8-(2-hydroxycyclohexyl)-5-{[4-(4-methoxyphenyl)piperazin-1-yl]methyl}-9-methyl-8,9-dihydro-7H-pyrrolo[3,4-h]quinolin-7-one,
5-{[4-(4-fluorophenyl)piperazin-1-yl]methyl}-8-(2-hydroxycyclohexyl)-8,9-dihydro-7H-pyrrolo[3,4-h]quinolin-7-one,
5-{[4-(4-fluorophenyl)piperazin-1-yl]methyl}-8-(2-hydroxycyclohexyl)-9-methyl-8,9-dihydro-7H-pyrrolo[3,4-h]quinolin-7-one,
5-{[4-(4-fluorophenyl)piperazin-1-yl]methyl}-8-(2-hydroxycyclohexyl)-9-methyl-8,9-dihydro-7H-pyrrolo[3,4-h]quinolin-7-one,
8-(2-hydroxycyclohexyl)-5-[(4-phenylpiperazin-1-yl)methyl]-8,9-dihydro-7H-pyrrolo[3,4-h]quinolin-7-one,
8-(2-hydroxycyclohexyl)-9-methyl-5-[(4-phenylpiperazin-1-yl)methyl]-8,9-dihydro-7H-pyrrolo[3,4-h]quinolin-7-one,
8-(2-hydroxycyclohexyl)-9-methyl-5-[(4-phenylpiperazin-1-yl)methyl]-8,9-dihydro-7H-pyrrolo[3,4-h]quinolin-7-one
1-({2-[(1S,2S)-2-hydroxycyclohexyl]-1-methyl-3-oxo-2,3-dihydro-1H-benzo[e]isoindol-5-yl}methyl)-4-(pyridin-2-yl)piperidine-4-carbonitrile,
1-{[2-(2-fluorophenyl)-3-oxo-2,3-dihydro-1H-benzo[e]isoindol-5-yl]methyl}-4-(4-methylpyridin-2-yl)piperidine-4-carbonitrile,
2-(2-fluorophenyl)-5-{[1-(pyridin-4-yl)-3,4-dihydroisoquinolin-2(1H)-yl]methyl}-1,2-dihydro-3H-benzo[e]isoindol-3-one,
2-(2-fluorophenyl)-5-{[4-(pyridin-2-yl)piperazin-1-yl]methyl}-1,2-dihydro-3H-benzo[e]isoindol-3-one,
2-(2-fluorophenyl)-5-{[4-(pyridin-2-yl)piperazin-1-yl]methyl}-1,2-dihydro-3H-benzo[e]isoindol-3-one,
and pharmaceutically acceptable salts thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formula (I), or a pharmaceutically acceptable salt thereof.

The invention is also directed to the use of a compound of formula (I), for treating a disease or disorder in which the M1 receptor is involved, such as Alzheimer's Disease, cognitive impairment, schizophrenia, pain disorders and sleep disorders, by administering to the patient a compound of formula (I), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formula (I), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising combining a compound of formula (I), or a pharmaceutically acceptable salt thereof, with a pharmaceutically acceptable carrier.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

If and when $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyl are $C_2$-$C_6$ alkynyl.

"Alkenyl," "alkynyl" and other like terms include carbon chains containing at least one unsaturated C—C bond.

As used herein, "fluoroalkyl" refers to an alkyl substituent as described herein containing at least one fluorine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

In certain other embodiments, the heterocyclic group is fused to an aryl or heteroaryl group. Examples of such fused heterocycles include, without limitation, tetrahydroquinolinyl and dihydrobenzofuranyl.

The term "heterocycloalkyl", as used herein except where noted, represents a non-aromatic cyclic or polycyclic group having from five to twelve ring atoms selected from C, O, N or S, at least one of which is O, N or S. Examples of heterocycloalkyls include azetidinyl, pyrrolidinyl, piperidinyl, piperazinyl, morpholinyl, pyranyl, tetrahydrofuranyl, imidazolinyl, pyrrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4-difluoro-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$alkylsulfinyl, arylalkylsulfnyl, arylsulfnyl, $C_1$-$C_8$ alkylsulfonyl, arylalkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" or "halo" refers to fluorine, chlorine, bromine and iodine.

The term "mammal" "mammalian" or "mammals" includes humans, as well as animals, such as dogs, cats, horses, pigs and cattle.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formula (I).

Formula (I), are shown above without a definite stereochemistry. The present invention includes all stereoisomers of formula (I), and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

Specific embodiments of the compounds of the invention, and methods of making them, are described in the Examples herein.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther*, 1993, 58:319-379; *Eur J Pharmacol*, 1996, 295:93-102, and *Mol Pharmacol*, 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

Suitable pharmaceutically acceptable salts include ammonium, sodium, potassium, hydrochloride, hydrobromide and fumarate.

The present invention is directed to the use of the compounds of formula (I) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention may have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention may be useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline. Thus, in another specific embodiment, the compounds of the present invention may be useful as a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists, such as ABT089, SSR180711 and MEM63908; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; $GABA_A$ inverse agonists; GSK3β inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formula (I) is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The following abbreviations are used throughout the text:
Me: methyl
Et: ethyl
t-Bu: tert-butyl
Ar: aryl
Ph: phenyl
Bn: benzyl
DCE: dichloroethylene
HMDS: hexamethyldisilazane
DMF: dimethylformamide
DMFDMA: N,N-dimethylformamide dimethylacetal
THF: tetrahydrofuran
BOP: benzotriazolyloxytris(dimethylamino) phosphonium hexafluorophosphate
Boc: tert-butyloxycarbonyl
TBS: tert-butyldimethylsilyl
TEA: triethylamine
TPAP: tetra-n-propyl ammonium perruthenate
NMO: N-methyl morpholine N-oxide
ClZn: Chlorozinc
dppf: diphenylphosphorousferrocenyl
PMB: p-methoxybenzyl
Ms: mesyl
Ac: acetyl
DMSO: dimethylsulfoxide DCM: dichloromethane
m-CPBA: meta-chloroperoxybenzoic acid
DMEM: Dulbecco's Modified Eagle Medium (High Glucose)
FBS: fetal bovine serum
rt: room temperature
aq: aqueous
HPLC: high performance liquid chromatography
MS: mass spectrometry
CDX TA P1G5 **
GDH-103 **
KRED-130 **

**Codex Transaminase panel enzyme P1 G5 (commercially available from Codex (Redwood City, Calif., USA) panel products.

Several methods for preparing the compounds of this invention are illustrated in the schemes and examples herein. Starting materials are made according to procedures known in the art or as illustrated herein. The following examples are provided so that the invention might be more fully understood. The present invention also provides a method for the synthesis of compounds useful as intermediates in the preparation of compounds of the invention.

Example 1

1-({2-[(1S,2S)-2-Hydroxycyclohexyl]-3-oxo-2,3-dihydro-1H-benzo[e]isoindol-5-yl}methyl)-4-(pyridine-2-yl)piperidine-4-carbonitrile

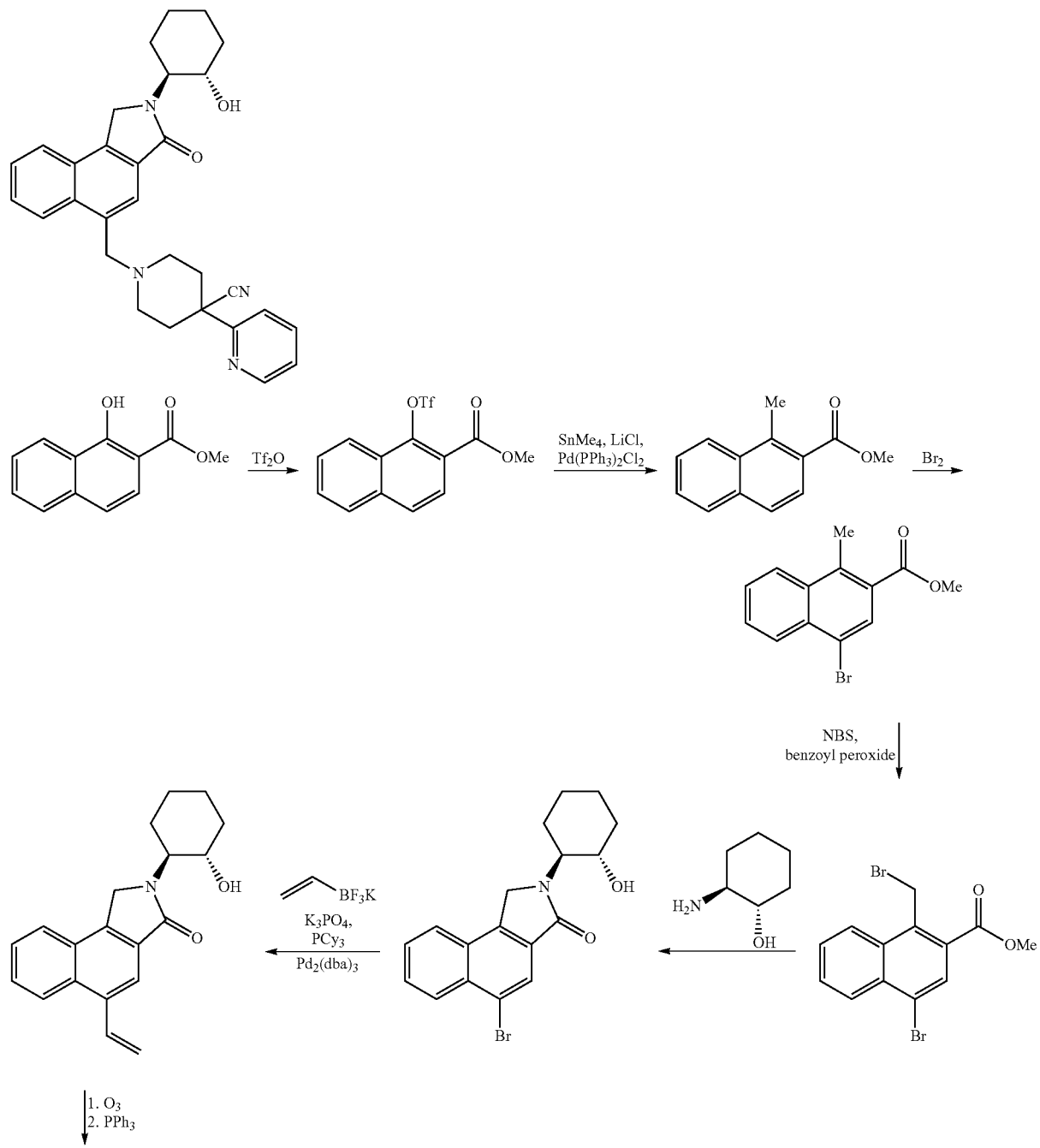

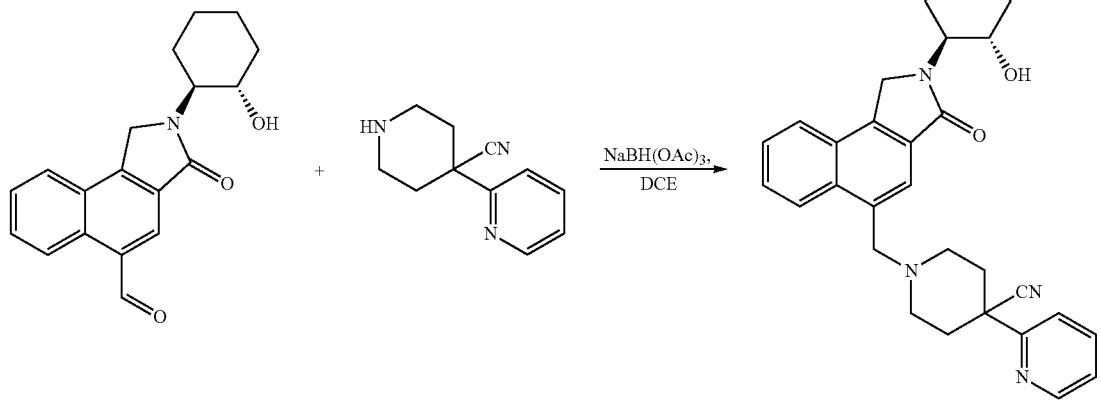

Preparation of 4-pyridin-2-ylpiperidine-4-carbonitrile

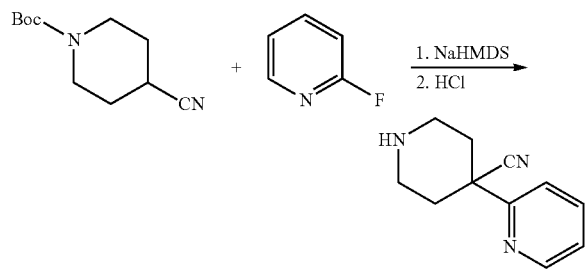

To a solution of tert-butyl 4-cyanopiperidine-1-carboxylate (0.220 g, 1.05 mmol) and 2-fluoropyridine (0.107 g, 1.10 mmol) in 5 mL of tetrahydrofuran at −78° C. was added sodium bis(trimethylsilyl)amide (1 M solution in diethyl ether, 1.47 mL, 1.47 mmol) dropwise. After 1 hr, the mixture was slowly warmed to ambient temperature, treated with saturated aqueous ammonium chloride, and extracted 3× with dichloromethane. The combined organic extracts were dried with sodium sulfate, filtered, and concentrated in vacuo. The residue was purified via silica gel chromatography, eluting with 0-20% ethyl acetate in hexanes, to provide tert-butyl 4-cyano-4-pyridin-2-ylpiperidine-1-carboxylate.

A solution of this clear oil in 5 mL of ethyl acetate at 0° C. was saturated with gaseous hydrogen chloride and then warmed to ambient temperature. After 18 hr, the mixture was concentrated in vacuo to provide 4-pyridin-2-ylpiperidine-4-carbonitrile hydrochloride.

To a solution of 1-hydroxy-2-naphthoic acid methyl ester (5.10 g, 25.2 mmol) in 35 mL of pyridine at −5° C. was added trifluoromethanesulfonic anhydride (12.8 mL, 76.0 mmol). After 1 hr, the mixture was poured into 250 mL of ice water and extracted with hexanes and ethyl acetate. The combined organic fractions were washed with water and brine, dried with magnesium sulfate, filtered, and concentrated in vacuo. The residue was purified via silica gel chromatography, eluting with 0-20% ethyl acetate in hexanes, to provide methyl 1-{[(trifluoromethyl)sulfonyl]oxy}-2-naphthoate that gave a mass ion (ES+) of 335.1 for [M+H]+.

To a solution of the above compound (4.30 g, 12.9 mmol) in 35 mL of N,N-dimethylformamide under an atmosphere of nitrogen was added lithium chloride (2.73 g, 64.3 mmol), bis(triphenylphosphine)palladium(II) chloride (0.451 g, 0.643 mmol), and tetramethyltin (3.92 mL, 28.3 mmol). The mixture was heated at 110° C. for 3 h, cooled to ambient temperature, and diluted with ethyl acetate. The organic solution was washed with saturated aqueous sodium bicarbonate, water, and brine, dried with magnesium sulfate, filtered, and concentrated in vacuo. The residue was purified via silica gel chromatography, eluting with 0-10% ethyl acetate in hexanes, to provide methyl 1-methyl-2-naphthoate that gave a mass ion (ES+) of 201.1 for [M+H]+.

To a solution of the above compound (1.00 g, 4.99 mmol) in 5 mL of acetic acid under an atmosphere of nitrogen was added a 5 mL acetic acid solution of bromine (0.257 mL, 4.99 mmol). The mixture was heated at 90° C. for 4 hr, cooled to ambient temperature and stirred for an additional 15 hr. The mixture was poured into water and extracted with dichloromethane. The organic solution was washed with saturated aqueous sodium bicarbonate, water, and brine, dried with magnesium sulfate, filtered, and concentrated in vacuo. The residue was purified via silica gel chromatography, eluting with 0-30% ethyl acetate in hexanes, to provide methyl 4-bromo-1-methyl-2-naphthoate that gave a mass ion (ES+) of 281.1 for [M+H]+.

To a solution of the above compound (1.29 g, 4.62 mmol) in 25 mL of carbon tetrachloride under an atmosphere of nitrogen was added N-bromosuccinimide (0.823 g, 4.62 mmol) and benzoyl peroxide (0.056 g, 0.231 mmoL). The mixture was heated at 90° C. for 1 hr, cooled to ambient temperature, and diluted with ethyl acetate. The organic solution was washed with saturated aqueous sodium bicarbonate, water, and brine, dried with magnesium sulfate, filtered, and concentrated in vacuo. The residue was purified via silica gel chromatography, eluting with 0-10% ethyl acetate in hexanes, to provide methyl 4-bromo-1-(bromomethyl)-2-naphthoate that gave a proton NMR spectra consistent with theory.

To a solution of the above compound (0.100 g, 0.279 mmol) in 1 mL of THF was added (1S,2S)-2-aminocyclohexanol (0.161 g, 1.40 mmol). After 15 hr, water (10 mL) was added, the mixture was aged for 30 min and was filtered, providing 5-bromo-2-[(1S,2S)-2-hydroxycyclohexyl]-1,2-dihydro-3H-benzo[e]isoindol-3-one as a white solid that gave a mass ion (ES+) of 362.3 for [M+H]+.

To a solution of the above compound (0.225 g, 0.625 mmol) in 2.5 mL of 1,4-dioxane under an atmosphere of nitrogen was added potassium vinyltrifluoroborate (0.167 g, 1.25 mmol), potassium phosphate (1.27 M aqueous, 0.84 mL, 1.1 mmol), tricyclohexylphosphine (4.2 mg, 0.015 mmol), and tris[dibenzylideneacetone]dipalladium (0) (5.7 mg, 0.0062 mmol). The mixture was irradiated in a microwave reactor at 140° C. for 30 min, cooled to ambient temperature, and diluted with saturated aqueous sodium bicarbonate. The mixture was extracted 2× with dichloromethane and the combined organic extracts were washed with brine, dried with magnesium sulfate, filtered, and concentrated in vacuo. The residue was purified via preparative reverse phase HPLC to provide 5-ethenyl-2-[(1S,2S)-2-hydroxycyclohexyl]-1,2-dihydro-3H-benzo[e]isoindol-3-one that gave a proton NMR spectra consistent with theory.

A solution of the above compound (0.086 g, 0.28 mmol) in 5 mL of dichloromethane was cooled to −78° C. and saturated with ozone. After 5 min, the solution was sparged with nitrogen gas and resin-bound triphenylphosphine (3 mmol/g, 0.600 g, 1.8 mmol) was added. The mixture was warmed to ambient temperature and filtered through Celite. The filtrate was concentrated in vacuo to provide 2-[(1S,2S)-2-hydroxycyclohexyl]-3-oxo-2,3-dihydro-1H-benzo[e]isoindole-5-carbaldehyde.

To a solution of the above compound (0.072 g, 0.23 mmol) in 4 mL of 1,2-dichloroethane was added 4-(pyridine-2-yl)piperidine-4-carbonitrile (0.048 g, 0.26 mmol), and sodium triacetoxyborohydride (0.099 g, 0.46 mmol). After 15 hr, the mixture was diluted with saturated aqueous sodium bicarbonate and extracted 2× with dichloromethane. The combined organic extracts were washed with brine, dried with magnesium sulfate, filtered, and concentrated in vacuo. The residue was purified via preparative reverse phase HPLC to provide the title compound that gave a proton NMR spectra consistent with theory and a mass ion (ES+) of 481.5 for [M+H]$^+$: NMR (400 MHz, CDCl$_3$) δ 8.60-8.58 (m, 1H), 8.36-8.34 (m, 1H), 7.88-7.84 (m, 1H), 7.77 (s, 1H), 7.74-7.69 (m, 1H), 7.65-7.56 (m, 3H), 7.25-7.21 (m, 1H), 4.84-4.69 (m, 2H), 4.21-4.15 (m, 1H), 3.95 (s, 2H), 3.77 (br s, 1H), 3.00 (br s, 2H), 2.68-2.56 (m, 2H), 2.34-2.21 (m, 2H), 2.08-1.97 (m, 3H), 1.86-1.83 (m, 2H), 1.71-1.30 (m, 5H) ppm.

Example 2

5-{[4-Fluoro-4-(pyridine-2-yl)piperidine-1-yl]methyl}-2-[(1S,2S)-2-hydroxycyclohexyl]-1,2-dihydro-3H-benzo[e]isoindol-3-one

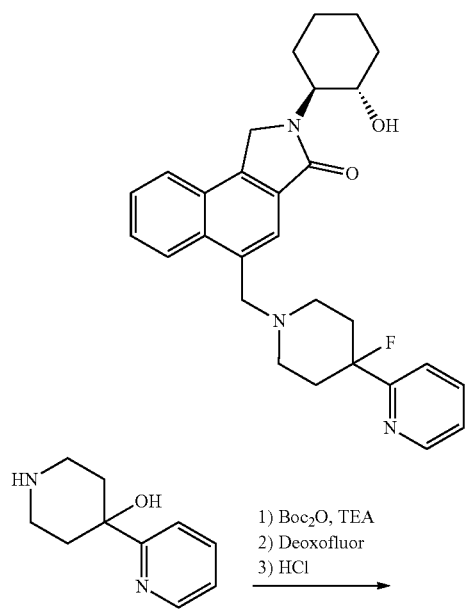

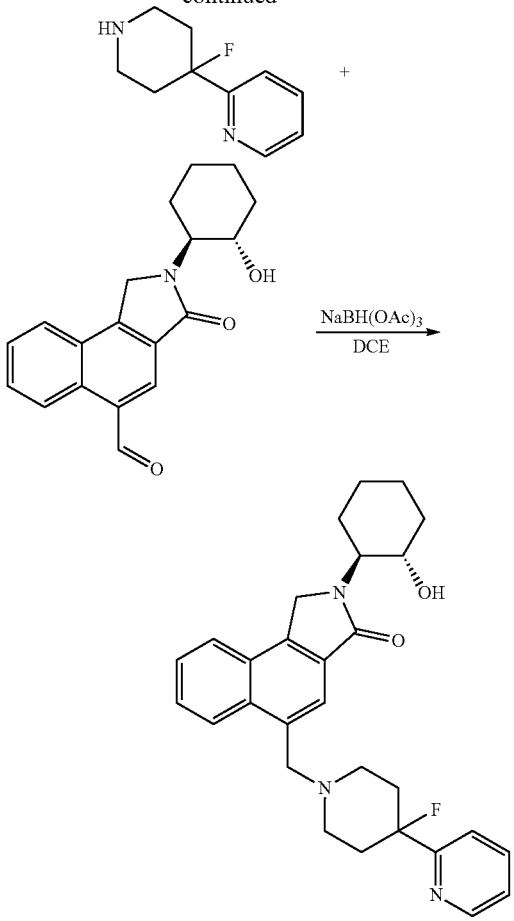

Preparation of 2-(4-fluoropiperidin-4-yl)pyridine

To a solution of 4-pyridin-2-ylpiperidin-4-ol dihydrochloride (0.415 g, 1.65 mmol) in 5 mL of dichloromethane was added triethylamine (0.58 mL, 4.1 mmol) and di-tert-butyl dicarbonate (0.361 g, 1.65 mmol). After 30 min, the mixture was treated with water and extracted 2× with dichloromethane. The combined organic extracts were washed with brine, dried with sodium sulfate, filtered, and concentrated in vacuo to provide tert-butyl 4-hydroxy-4-pyridin-2-ylpiperidine-1-carboxylate that gave a proton NMR spectra consistent with theory.

To a solution of the above compound (0.240 g, 0.862 mmol) in 4 mL of dichloromethane at −78° C. was added [bis(2-methoxyethyl)amino]sulfur trifluoride (deoxofluor, 0.32 mL, 1.7 mmol). The mixture was warmed to ambient temperature and after 1 hr, was treated with water and extracted 2× with dichloromethane. The combined organic extracts were washed with brine, dried with sodium sulfate, filtered, and concentrated in vacuo. The residue was purified via silica gel chromatography, eluting with 10-40% ethyl acetate in hexanes, to provide tert-butyl 4-fluoro-4-pyridin-2-ylpiperidine-1-carboxylate that gave proton NMR spectra consistent with theory.

A solution of tert-butyl 4-fluoro-4-pyridine-2-ylpiperidine-1-carboxylate (0.075 g, 0.27 mmoL) in 10 mL of ethyl acetate was saturated with gaseous hydrochloric acid. After 1 hr, the mixture was concentrated in vacuo to provide 2-(4-fluoropiperidin-4-yl)pyridine hydrochloride that gave a mass ion (ES+) of 181.1 for [M+H]$^+$ The title compound was prepared employing the procedures described for the construction of 1-({2-[(1S,2S)-2-hydroxycyclohexyl]-3-oxo-2,3-dihydro-1H-benzo[e]isoindol-5-yl}methyl)-4-(pyridine-2-yl)piperidine-4-carbonitrile in Example 1, substituting 2-(4-fluoropiperidin-4-yl)pyridine for 4-pyridin-2-ylpiperidine-4-carbonitrile. The resultant white solid gave proton NMR spectra consistent with theory and a mass ion (ES+) of 474.2554 for [M+H]+[calc'd for C29H33FN3O2, [M+H]+=474.2551]: 1H NMR (400 MHz, CDCl3) δ 8.54-8.49 (m, 2H), 7.87-7.84 (m, 1H), 7.80 (s, 1H), 7.72-7.66 (m, 1H), 7.66-7.55 (m, 3H), 7.21-7.16 (m, 1H), 4.83-4.70 (m, 2H), 4.21-4.09 (m, 1H), 3.98 (s, 2H), 3.81-3.73 (m, 1H), 2.89-2.86 (m, 2H), 2.56-2.50 (m, 2H), 2.43-2.20 (m, 3H), 2.02-1.98 (m, 1H), 1.89-1.83 (m, 4H), 1.73-1.63 (m, 1H), 1.54-1.32 (m, 3H) ppm.

Example 3

1-({2-[(1S,2S)-2-Hydroxycyclohexyl]-1-methyl-3-oxo-2,3-dihydro-1H-benzo[e]isoindol-5-yl}methyl)-4-(pyridine-2-yl)piperidine-4-carbonitrile

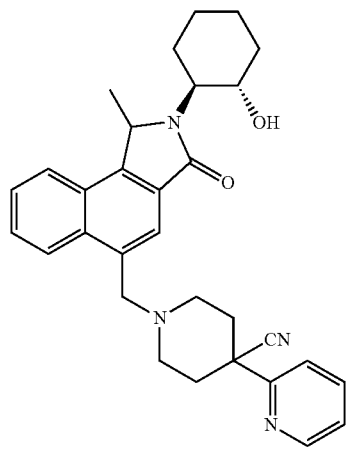

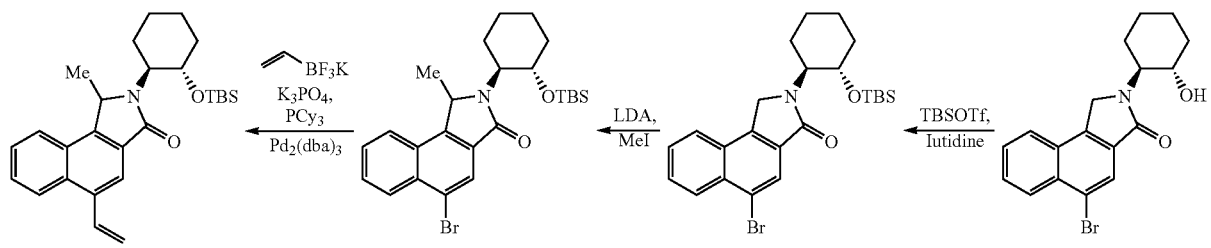

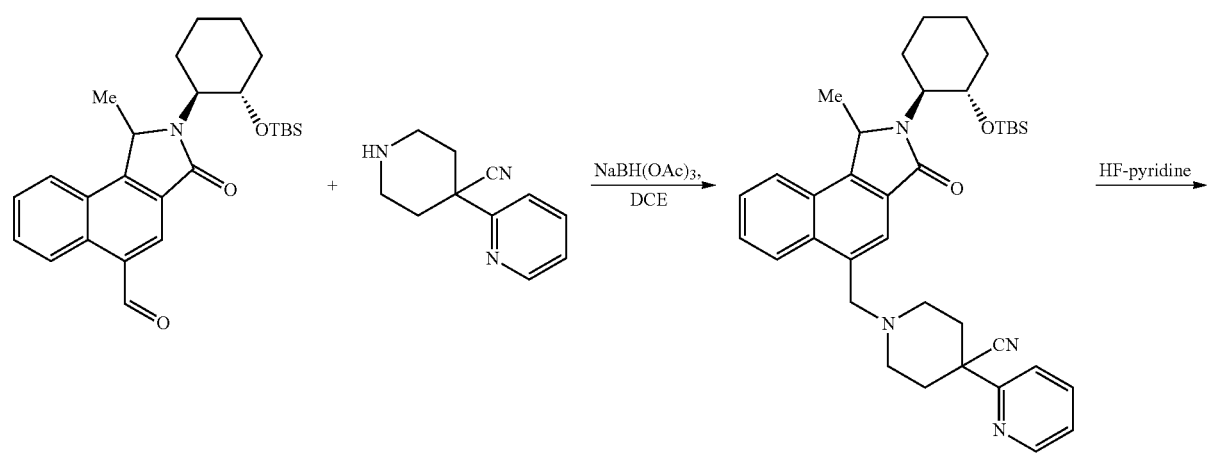

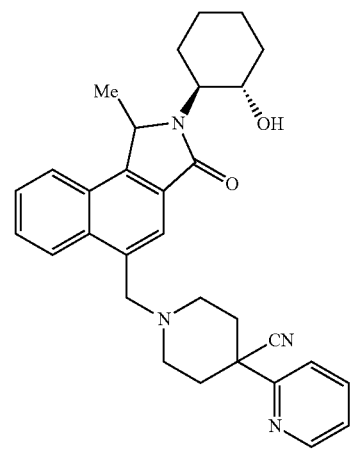

To a solution of 5-bromo-2-[(1S,2S)-2-hydroxycyclohexyl]-1,2-dihydro-3H-benzo[e]isoindol-3-one (see Example 1, 2.00 g, 5.55 mmol) in 15 mL of dichloromethane at 0° C. was added 2,6-lutidine (1.29 mL, 11.1 mmol) and tert-butyldimethylsilyl trifluoromethanesulfonate (1.91 mL, 8.33 mmol). The mixture was warmed to ambient temperature and after 15 hr, was treated with water. The mixture was extracted 2× with ethyl acetate and the combined organic extracts were washed with brine, dried with magnesium sulfate, filtered, and concentrated in vacuo. The residue was purified via silica gel chromatography, eluting with 0-40% ethyl acetate in hexanes, to provide 5-bromo-2-[(1S,2S)-2-{[tert-butyl(dimethyl)silyl]oxy}cyclohexyl]-1,2-dihydro-3H-benzo[e]isoindol-3-one that gave a mass ion (ES+) of 475.1 for [M+H]$^+$.

To a solution of diisopropylamine (0.75 mL, 5.3 mmol) in 5 mL of THF at 0° C. was added n-butyllithium (2.5 M tetrahydrofuran solution, 2.32 mL, 5.80 mmol) dropwise, which was added after 30 min to a solution of the above compound (0.500 g, 1.05 mmol) in 5 mL of THF at −78° C. After 30 min, iodomethane (0.072 mL, 1.2 mmol) was added dropwise and after 1 h, the mixture was warmed to ambient temperature, treated with saturated aqueous ammonium chloride, and extracted 2× with ethyl acetate. The combined organic extracts were washed with water and brine, dried with magnesium sulfate, filtered, and concentrated in vacuo. The residue was purified via silica gel chromatography, eluting with 0-20% ethyl acetate in hexanes, to provide (1S)- and (1R)-5-bromo-2-[(1S,2S)-2-{[tert-butyl(dimethyl)silyl]oxy}cyclohexyl]-1-methyl-1,2-dihydro-3H-benzo[e]isoindol-3-one that gave a proton NMR spectra consistent with theory.

1-({2-[(1S,2S)-2-{[tert-Butyl(dimethyl)silyl]oxy}cyclohexyl]-1-methyl-3-oxo-2,3-dihydro-1H-benzo[e]isoindol-5-yl}methyl)-4-(pyridin-2-yl)piperidine-4-carbonitrile was prepared employing the procedures described for the construction of 1-({2-[(1S,2S)-2-hydroxycyclohexyl]-3-oxo-2,3-dihydro-1H-benzo[e]isoindol-5-yl}methyl)-4-(pyridine-2-yl)piperidine-4-carbonitrile in Example 1, substituting 5-bromo-2-[(1S,2S)-2-{[tert-butyl(dimethyl)silyl]oxy}cyclohexyl]-1-methyl-1,2-dihydro-3H-benzo[e]isoindol-3-one for 5-bromo-2-[(1S,2S)-2-hydroxycyclohexyl]-1,2-dihydro-3H-benzo[e]isoindol-3-one.

To a solution of 1-({2-[(1S,2S)-2-{[tert-butyl(dimethyl)silyl]oxy}cyclohexyl]-1-methyl-3-oxo-2,3-dihydro-1H-benzo[e]isoindol-5-yl}methyl)-4-(pyridin-2-yl)piperidine-4-carbonitrile (0.120 g, 0.197 mmol) in 0.1 mL of pyridine was added hydrogen fluoride pyridine (0.098 g, 0.98 mmol). After 15 hr, the mixture was treated with saturated aqueous sodium bicarbonate and extracted 2× with ethyl acetate. The combined organic extracts were washed with brine, dried with magnesium sulfate, filtered, and concentrated in vacuo. The residue was purified via silica gel chromatography, eluting with 10-100% ethyl acetate in hexanes, to provide the titled compound that gave a proton NMR spectra consistent with theory and a mass ion (ES+) of 495.2765 for [M+H]$^+$ [calc'd for $C_{31}H_{35}N_4O_2$, [M+H]$^+$=495.2755]: $^1$H NMR (400 MHz, CDCl$_3$) δ 8.60-8.58 (m, 1H), 8.45-8.41 (m, 1H), 7.95-7.90 (m, 1H), 7.83-7.79 (m, 1H), 7.74-7.69 (m, 1H), 7.66-7.56 (m, 3H), 7.25-7.21 (m, 1H), 5.11-5.03 (m, 2H), 4.42 (br s, 1H), 4.03-3.98 (m, 2H), 3.79-3.72 (m, 1H), 3.65-3.59 (m, 1H), 3.06-3.02 (m, 2H), 2.88-2.86 (m, 1H), 2.67-2.59 (m, 2H), 2.35-2.17 (m, 2H), 2.09-2.06 (m, 1H), 2.04-1.81 (m, 2H), 1.42-1.22 (m, 4H), 0.96-0.83 (m, 4H) ppm.

Example 4

1-({2-[(1S,2S)-2-Hydroxycyclohexyl]-3-oxo-2,3-dihydro-1H-benzo[e]isoindol-5-yl}methyl)-4-(6-methylpyridin-2-yl)piperidine-4-carbonitrile

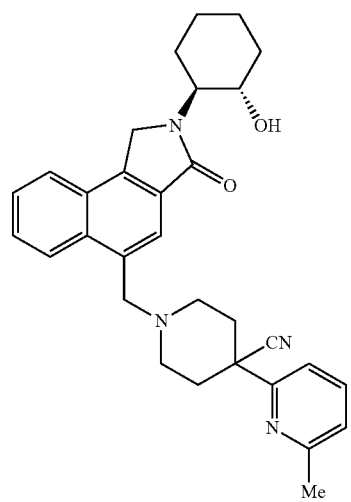

-continued

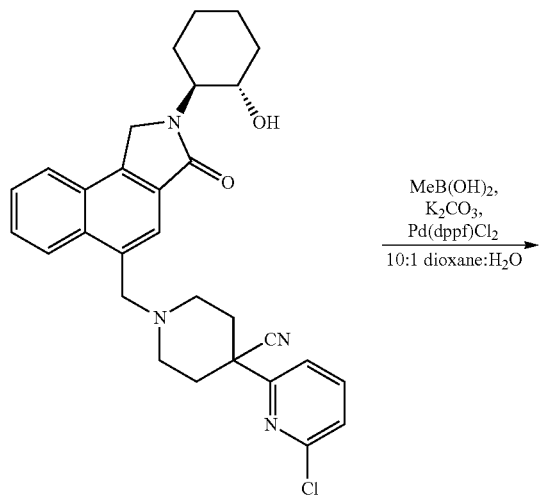

4-(6-Chloropyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile was prepared employing the procedures described for the construction of 1-({2-[(1S,2S)-2-hydroxycyclohexyl]-3-oxo-2,3-dihydro-1H-benzo[e]isoindol-5-yl}methyl)-4-(pyridine-2-yl)piperidine-4-carbonitrile in Example 1, substituting 2-chloro-6-fluoropyridine for 2-fluoropyridine.

To a solution of 4-(6-chloropyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile (0.050 g, 0.097 mmol) in 1 mL mixture of 1,4-dioxane:water (10:1) under an atmosphere of nitrogen was added methylboronic acid (7.0 mg, 0.12 mmol), potassium carbonate (0.040 g, 0.29 mmol), and [1,1'-bis(diphenylphosphino)ferrocene]dichloro-palladium(II), 1:1 complex with dichloromethane (1.4 mg, 0.0019 mmol). The mixture was irradiated in a microwave reactor at 125° C. for 1 hr, cooled to ambient temperature and extracted 2× with dichloromethane. The combined organic extracts were dried with magnesium sulfate, filtered, and concentrated in vacuo. The residue was purified via preparative reverse phase HPLC to provide the titled compound that gave a proton NMR spectra consistent with theory and a mass ion (ES+) of 495.2765 for [M+H]$^+$ [calc'd for C$_{31}$H$_{35}$N$_4$O$_2$, [M+H]$^+$=495.2755]: $^1$H NMR (400 MHz, CDCl$_3$) δ 8.35-8.33 (m, 1H), 7.88-7.85 (m, 1H), 7.76 (s, 1H), 7.66-7.54 (m, 3H), 7.34-7.32 (m, 1H), 7.07-7.04 (m, 1H), 4.84-4.68 (m, 2H), 4.20-4.14 (m, 1H), 3.98-3.79 (m, 2H), 3.77-3.74 (m, 1H), 3.02-2.96 (m, 1H), 2.63-2.55 (m, 1H), 2.52 (s, 3H), 2.36-2.21 (m, 2H), 2.06-1.97 (m, 2H), 1.90-1.82 (m, 1H), 1.70-1.25 (m, 6H), 0.97-0.83 (m, 3H) ppm.

Example 5

4-(6-Ethylpyridin-2-yl)-1-({2-[(1S,2S)-hydroxycyclohexyl]-3-oxo-2,3-dihydro-1H-benzo[e]isoindol-5-yl}methyl)piperidine-4-carbonitrile

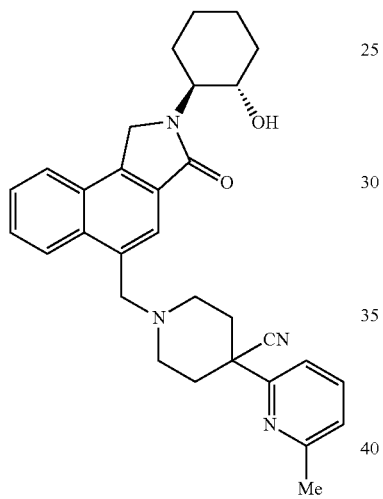

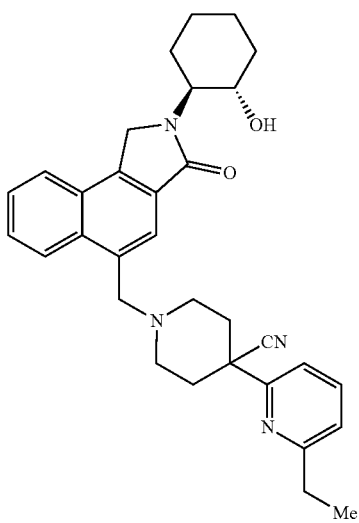

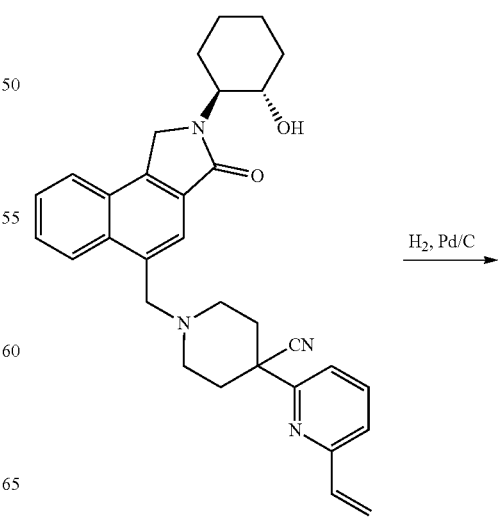

43
-continued

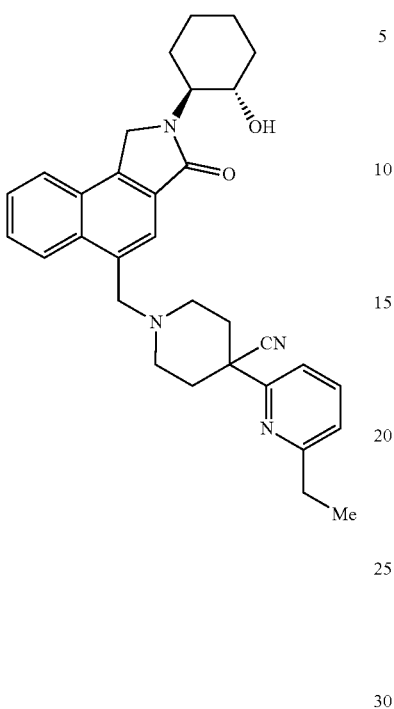

4-(6-Ethenylpyridin-2-yl)-1-({2-[(1S,2S)-2-hydroxycyclohexyl]-3-oxo-2,3-dihydro-1H-benzo[d]isoindol-5-yl}methyl)piperidine-4-carbonitrile was prepared employing the procedures described for the construction of 1-({2-[(1S,2S)-2-hydroxycyclohexyl]-3-oxo-2,3-dihydro-1H-benzo[d]isoindol-5-yl}methyl)-4-(6-methylpyridin-2-yl)piperidine-4-carbonitrile in Example 4, substituting potassium vinyltrifluoroborate for methylboronic acid.

To a solution of 4-(6-ethenylpyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile (0.016 g, 0.032 mmol) in 1 mL of ethyl acetate under an atmosphere of nitrogen was added palladium on carbon (3.4 mg, 0.032 mmol). The mixture was placed under an atmosphere of hydrogen (1 atm) for 1 hr, filtered through a pad of Celite and concentrated in vacuo to provide the titled compound that gave a proton NMR spectra consistent with theory and a mass ion (ES+) of 509.2917 for [M+H]$^+$[calc'd for $C_{32}H_{37}N_4O_2$, [M+H]$^+$=509.2911]: $^1$H NMR (400 MHz, CDCl$_3$) δ 8.35-8.33 (m, 1H), 7.88-7.86 (m, 1H), 7.78 (s, 1H), 7.66-7.57 (m, 3H), 7.35-7.33 (m, 1H), 7.07-7.05 (m, 1H), 4.84-4.69 (m, 2H), 4.21-4.14 (m, 1H), 3.98-3.89 (m, 2H), 3.81-3.74 (m, 1H), 2.99 (br s, 1H), 2.82-2.76 (m, 2H), 2.64-2.55 (m, 1H), 2.35-2.20 (m, 2H), 2.07-1.97 (m, 2H), 1.86-1.25 (m, 9H), 0.97-0.83 (m, 4H) ppm.

44

Example 6

1-({2-[(1S,2S)-2-Hydroxycyclohexyl]-3-oxo-2,3-dihydro-1H-benzo[e]isoindol-5-yl}methyl)-4-(6-methoxypyridin-2-yl)piperidine-4-carbonitrile

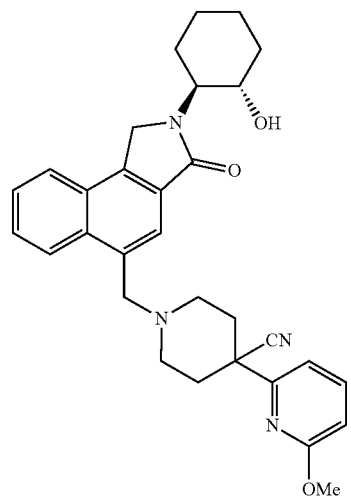

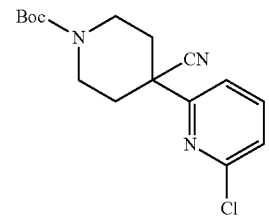

1. TBAOMe
2. HCl

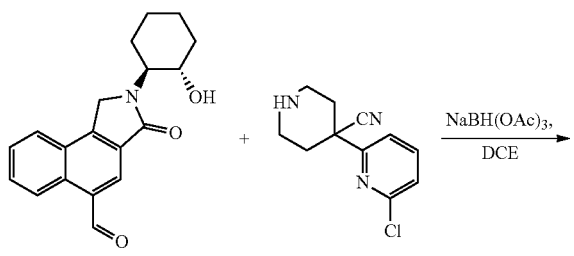

NaBH(OAc)$_3$, DCE

-continued

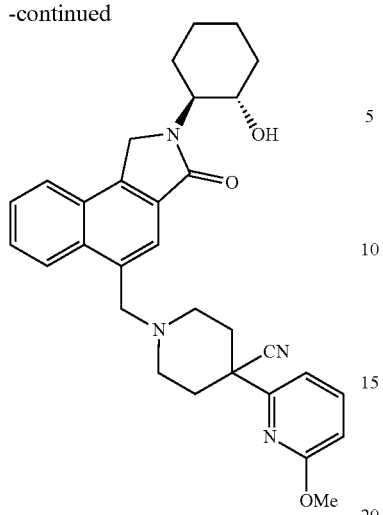

tert-Butyl 4-(6-chloropyridin-2-yl)-4-cyanopiperidine-1-carboxylate was prepared employing the procedures described for the construction of tert-butyl 4-cyano-4-pyridin-2-ylpiperidine-1-carboxylate in Example 1, substituting 2-chloro-6-fluoropyridine for 2-fluoropyridine.

To a vial containing tert-butyl 4-(6-chloropyridin-2-yl)-4-cyanopiperidine-1-carboxylate (0.300 g, 0.932 mmol) was added a methanolic solution of tetrabutylammonium methoxide (20%, 7.79 mL, 4.66 mmol). The vessel was sealed and the mixture was irradiated in a microwave reactor at 120° C. for 1 hr, cooled to ambient temperature and extracted 2× with ethyl acetate. The combined organic extracts were washed 3× with water, dried with magnesium sulfate, filtered, and concentrated in vacuo. The residue was purified via silica gel chromatography, eluting with 0-20% ethyl acetate in hexanes, to provide tert-butyl 4-cyano-4-methoxypyridin-2-yl)piperidine-1-carboxylate that gave a proton NMR spectra consistent with theory and a mass ion (ES+) of 340.0 for [M+H]$^+$.

The titled compound was prepared employing the procedures described for the construction of 1-({2-[(1S,2S)-2-hydroxycyclohexyl]-3-oxo-2,3-dihydro-1H-benzo[d]isoindol-5-yl}methyl)-4-(pyridine-2-yl)piperidine-4-carbonitrile in Example 1, substituting tert-butyl 4-cyano-4-methoxypyridin-2-yl)piperidine-1-carboxylate for tert-butyl 4-cyano-4-pyridin-2-ylpiperidine-1-carboxylate. The resultant white solid gave proton NMR spectra consistent with theory and a mass ion (ES+) of 511.2715 for [M+H]$^+$[calc'd for $C_{31}H_{35}N_4O_3$, [M+H]$^+$=511.2704]: $^1$H NMR (400 MHz, CDCl$_3$) δ 8.19-8.11 (m, 2H), 7.90-7.83 (m, 2H), 7.68 (s, 1H), 7.67-7.52 (m, 3H), 5.04-4.92 (m, 2H), 4.59-4.54 (m, 2H), 4.17-4.11 (m, 2H), 3.78-3.71 (m, 2H), 2.23-2.19 (m, 2H), 1.96-1.81 (m, 4H), 1.64-1.20 (m, 1H) ppm.

Example 7

1,5-Anhydro-2,3-dideoxy-3-{5-[(4,4-difluoropiperidin-1-yl)methyl]-7-oxo-7,9-dihydro-8H-pyrrolo[3,4-h]quinolin-8-yl}-L-threo-pentitol

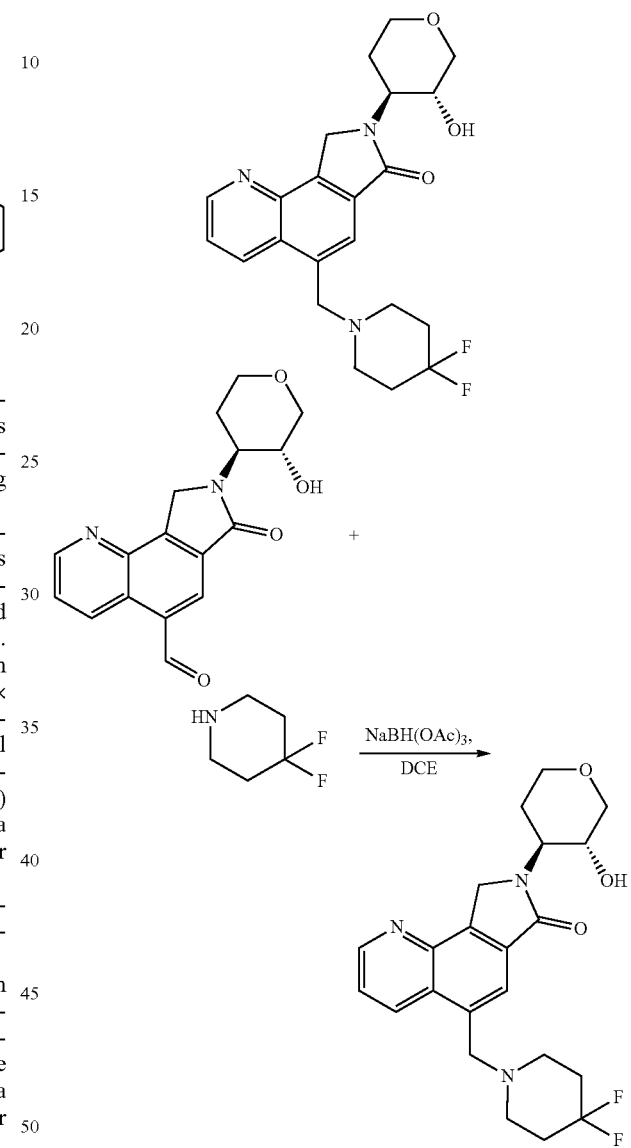

Preparation of
(3R,4S)-4-aminotetrahydro-2H-pyran-3-ol

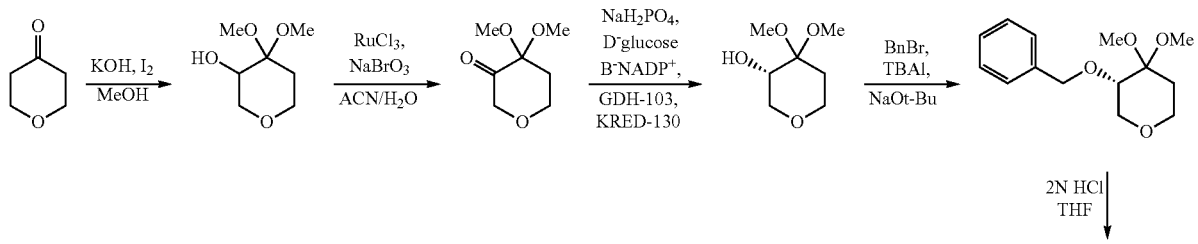

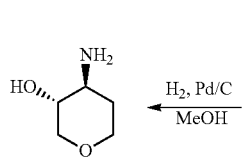 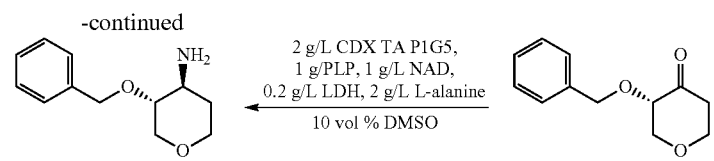

A jacketed flask equipped with an overhead stirrer and a thermocouple was charged with 23.0 L of MeOH, and cooled to 5° C. Potassium hydroxide (1.574 kg, 28.05 mol) was added to the flask, and the resulting solution was aged until homogeneous and recooled to 5° C. Tetrahydro-4H-pyran-4-one (1.00 kg, 10.0 mol) was then added at a steady rate over 20 min, and the resulting solution was aged for 20-30 min. A solution of iodine (2.778 kg, 10.95 mol) in 18.5 L of MeOH was then added via mechanical pump at a steady rate over 90-100 minutes. After an additional 30 min, the solution was warmed to rt and toluene (42.0 L) was added. The resulting slurry was concentrated in vacuo to a volume of ~8.4 L. Additional toluene (8.4 L) was added and the resulting solution was concentrated to a volume of 8.4 L 2×. The resulting slurry was then filtered, and the filter cake was rinsed 2× with toluene (4.0 L). The combined toluene streams were concentrated to ~6 L, and the product is extracted 2× with water (3.0 L) to provide 4,4-dimethyoxytetrahydro-2H-pyran-3-ol.

To a solution of the above compound (1.00 kg, 6.17 mol) in 5 L of water was added acetic acid to pH 5.2-5.4. The mixture was diluted with acetonitrile (4.0 L) and ruthenium trichloride hydrate (6.4 g, 0.028 mol) was added and rinsed in with additional acetonitrile (1.0 L). The flask was placed in a rt water bath and a solution of sodium bromate (650 g, 4.31 mol) in water (1.95 L) was added slowly over ~30 min, keeping the temperature below 30° C. After 2 h, potassium bicarbonate (430 g, 4.30 mol), sodium thiosulfate (1.07 kg, 4.31 mol), potassium chloride (500 g, 6.71 mol) and acetonitrile (5 L) were added sequentially. The layers were separated and the aqueous layer was extracted 3× with acetonitrile (10 L). The combined organic extracts were concentrated to =4 L. Toluene (5 L) was then added and the mixture reconcentrated to 4 L 4×. The mixture was diluted with toluene (7 L) and filtered to remove solids. The filtercake was washed 3× with toluene (2 L) and the combined filtrate and washes were concentrated to a total volume of 3 L to provide an organic solution of 4,4-dimethoxydihydro-2H-pyran-3(4H)-one. To a 3 L 3-neck RB flask with overhead stirring, thermocouple and heating mantle was added sodium dihydrogenphosphate (96.0 g, 800 mmol) in 1.6 L of water. Sodium hydroxide (29 mL, 50 wt %) was added to pH 7.13, followed by hydrochloric acid (5 mL, 6 N) to pH 7.02.

The above organic solution of 4,4-dimethoxydihydro-2H-pyran-3(4H)-one was extracted 3× with phosphate buffered water (0.55 L). To the combined aqueous extracts was added D-glucose (180 g, 100 mmol), and the solution was heated to 30° C. When the solution exceeded 27° C. upon heating B-NADP+ (1.60 g, 499 mmol), GDH-103 (1.60 g, 499 mmol), and KRED-130 (1.60 g, 499 mmol) were added and the mixture was stirred for 17 h at 30° C. Potassium chloride (200 g, 2.68 mol) and acetonitrile (1.3 L) were added. After 30 min, the reaction mixture was transferred to 6 L sep funnel and additional MeCN (0.67 L) and toluene (0.87 L) were added. The aqueous layer was back extracted 1× with a mixture of acetonitrile (1.95 L) and toluene (0.65 L), and 1× with acetonitrile (1.5 L). The combined organic extracts were concentrated in vacuo to provide (3S)-4,4-dimethoxytetrahydro-2H-pyran-3-ol.

To a 2 L RB flask with overhead stirring, thermocouple, heating mantle and N₂ inlet was added a solution of the above compound (72.0 g, 0.444 mol) in 750 mL of THF. After 15 h, sodium tert-butoxide (48.3 g, 492 mmol) was added in one portion, and the mixture was heated to 35° C. for 1 h, and aged at 22° C. for 1 hr. Tetrabutylammonium iodide (8.19 g, 22.2 mmol) and benzyl bromide (56.5 ml, 466 mmol) were added, and the mixture was heated to 50° C. for 2 h. The solution was cooled to 25° C., and water (750 mL) and MtBE (2.25 L) were added. The organic layer was separated from the aqueous and concentrated in vacuo. The resultant brown oil was purified via silica gel chromatography, eluting with 0-15% ethyl acetate in hexanes to provide (3S)-3-(benzylyoxy)-4,4-dimethoxytetrahydro-2H-pyran.

To a solution of the above compound (61.1 g, 225 mmol) in 300 mL of THF was added 2 N HCl (300 mL, 0.600 mol). After 1.5 h, saturated aqueous potassium carbonate (60 mL) was added via addition funnel to pH 7.4. The aqueous layer was extracted 3× with MtBE (300 mL) and the combined organic extracts were concentrated in vacuo to provide crude (3S)-3-(benzyloxy)tetrahydro-4H-pyran-4-one.

To a solution of L-Alanine (200 g, 2.24 mol), sodium formate (76.0 g, 1.12 mmol), and sodium phosphate dibasic (28.7 g, 202 mmol) in 2.25 L of water adjusted to pH 7.5 was added NAD (2.2 g, 3.21 mmol), pyridoxal-5-phosphate (2.2 g, 8.90 mmol), LDH (0.45 g, 0.22 mol), FDH (4.5 g, 0.20 mol), and TA P1G5 (4.5 g, 0.22 mol). After all the components were completely dissolved, (3S)-3-(benzyloxy)tetrahydro-4H-pyran-4-one (45 g, 0.22 mol) was added and the pH was adjusted to pH 7.25 with 6 N HCl and aged at 30° C. After 15 h, potassium carbonate (700 g, 5.06 mol) was added slowly, followed by ethyl acetate (2.2 L). The mixture was filtered through a bed of Solka Floc and the cake was washed with ethyl acetate (250 mL). The combined filtrates were separated and the aqueous layer was extracted a second time with ethyl acetate (2 L). The combined organic extracts were concentrated in vacuo to provide crude (3R,4S)-3-(benzyloxy)tetrahydro-2H-pyran-4-amine.

To a solution of the above compound (38.8 g, 0.187 mol) in 730 mL of methanol was added concentrated hydrochloric acid (23.3 mL). The solution was subjected to hydrogenation at 40 psi H₂, 25° C. over 5.8 g of 10% Pd/C (5.8 g). After 15 h, the mixture was filtered through solka floc and the filtercake was washed 5× with methanol (100 mL). The combined filtrate and washes were concentrated in vacuo to provide (3R,4S)-4-aminotetrahydro-2H-pyran-3-ol that gave proton NMR spectra consistent with theory.

5-Bromo-8-[(1S,2S)-2-hydroxycyclohexyl]-3,9-dihydro-7H-pyrrolo[3,4-h]quinolin-7-one was prepared employing the procedures described for the construction of 2-[(1S,2S)-2-hydroxycyclohexyl]-3-oxo-2,3-dihydro-1H-benzo[e]isoindole-5-carbaldehyde in Example 1, substituting methyl 8-hydroxyquinoline-7-carboxylate for 1-hydroxy-2-naphthoic acid methyl ester, and substituting provide (3R,4S)-4-aminotetrahydro-2H-pyran-3-ol for (1S,2S)-2-aminocyclohexanol.

The titled compound was prepared employing the procedures described for the construction of 1-({2-[(1S,2S)-2-hydroxycyclohexyl]-3-oxo-2,3-dihydro-1H-benzo[e]isoindol-5-yl}methyl)-4-(pyridine-2-yl)piperidine-4-carbonitrile in Example 1, substituting 4,4-difluoropiperidine for 4-pyridin-2-ylpiperidine-4-carbonitrile, and substituting 5-bromo-8-[(1S,2S)-2-hydrocyclohexyl]-3,9-dihydro-7H-pyrrolo[3,4-h]quinolin-7-one for 2-[(1S,2S)-2-hydroxycyclohexyl]-3-oxo-2,3-dihydro-1H-benzo[d]isoindole-5-carbaldehyde. The resultant white solid gave proton NMR spectra consistent with theory and a mass ion (ES+) of 418.1929 for [M+H]$^+$ [calc'd for $C_{22}H_{26}F_2N_3O_3$, [M+H]$^+$=418.1937]: $^1$H NMR (400 MHz, CDCl$_3$) δ 8.98-8.96 (m, 1H), 8.73-8.71 (m, 1H), 7.82 (s, 1H), 7.56-7.52 (m, 1H), 5.05-4.83 (m, 2H), 4.26-4.05 (m, 3H), 3.95 (s, 2H), 3.62-3.49 (m, 2H), 2.60-2.57 (m, 5H), 2.19-2.14 (m, 1H), 2.04-1.80 (m, 5H).

Example 8

1,5-Anhydro-2,4-dideoxy-2-{5-[(4,4-difluoropiperidin-1-yl)methyl]-7-oxo-7,9-dihydro-8H-pyrrolo[3,4-h]quinolin-8-yl}-L-threo-pentitol

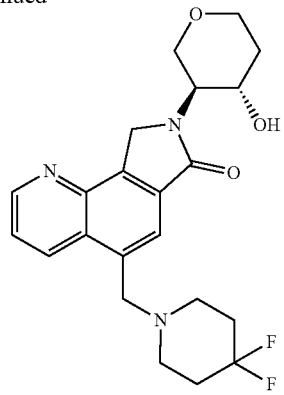

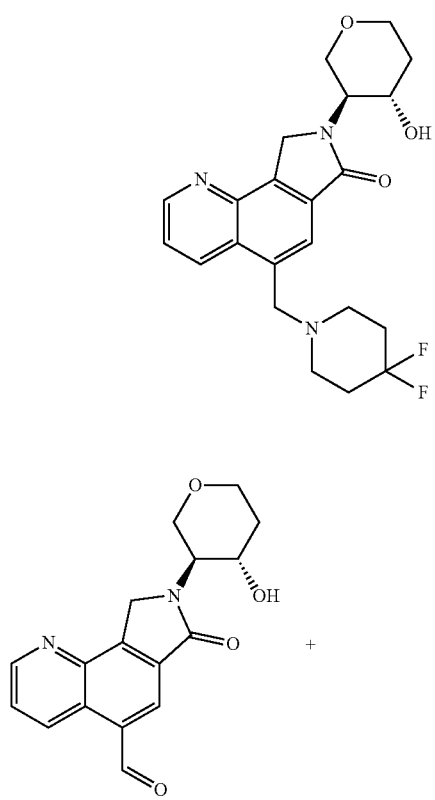

Preparation of (3S,4S)-3-aminotetrahydro-2H-pyran-4-ol

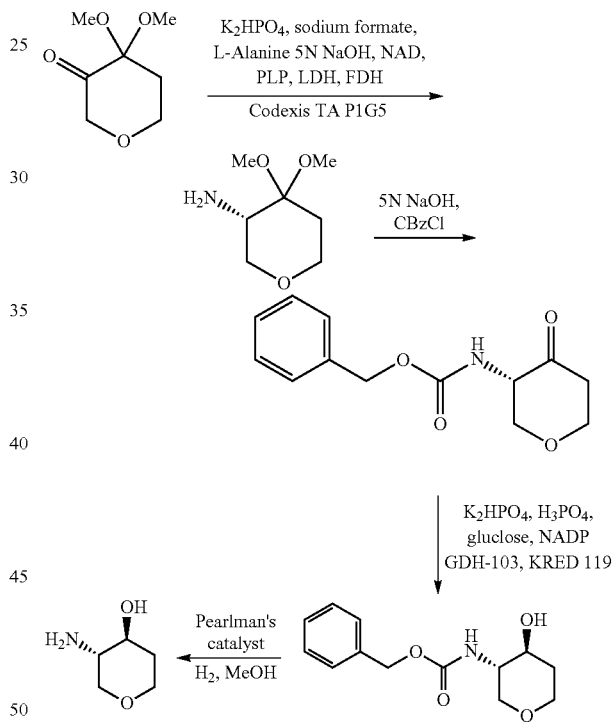

A solution of 4,4-dimethoxydihydro-2H-pyran-3(4H)-one (172 g, 1.07 mol, see Example 1) in 310 mL of toluene was stirred in toluene for 30 min, then extracted 3× with water (270 mL). To the aqueous solution was added potassium dihydrogenphosphate (14.1 g, 0.104 mol), sodium formate (55.1 g, 0.810 mol), and L-Alanine (72.2 g, 0.810 mol). The pH was adjusted to 7.8 with 5 N NaOH, and NAD (0.810 g), PLP (0.810 g), LDH (0.162 g), FDH (1.62 g), and Codexis TA P1G5 (4.05 g) were added. The mixture was heated to 45° C. for 12 h, then cooled to rt. Potassium carbonate (324 g, 2.34 mol) was added, and after 30 min, the mixture was diluted with acetonitrile (810 mL). After 30 min, the reaction was filtered through a pad of solka-floc. The filtrate was partitioned and the aqueous layer was extracted with additional acetonitrile (810 mL). The combined organic fractions were

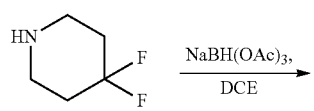

concentrated in vacuo to provide crude (3S)-4,4-dimethoxytetrahydro-2H-pyran-3-amine.

The above residue was redissolved in 700 mL of THF and 254 mL of water, and cooled to 0° C. Sodium hydroxide (5 N, 96 mL, 0.48 mol) was added, and the reaction was recooled to −5° C. Benzyl chloroformate (68.0 mL, 0.476 mol) was added via a syringe pump over 30 min, and the mixture was then warmed to rt. HCl (6 N, 250 mL, 1.50 mol) was added to pH=0.40, and the mixture was stirred with an overhead stirrer. After 2 h, 3M potassium carbonate was added to pH=7.4, and the reaction was diluted with THF (700 mL). A white solid was removed via filtration, and washed with additional THF (100 mL). The combined organic fractions were concentrated in vacuo to provide crude benzyl [(3S)-4-oxotetrahydro-2H-pyran-3-yl]carbamate.

To a solution of potassium dihydrogen phosphate (62.7 g, 0.461 mol) in 3.6 L of water was added phosphoric acid to pH=7.0. To this solution was added glucose (112 g, 0.622 mol), NADP (3.6 g), GDH-103 (1.8 g), KRED 119 (3.6 g), and crude benzyl [(3S)-4-oxotetrahydro-2H-pyran-3-yl]carbamate (103.4 g, 0.4148 mol). After 17 h, the reaction was adjusted to pH=6.5 with 5 N NaOH. A white solid was collected via filtration and washed 2× with water (200 mL). The solid was suspended in 600 mL of toluene and stirred with an overhead stirrer at 105° C. for 1 h, then cooled to rt. A white solid was collected via filtration and washed with toluene (200 mL) to provide benzyl [(3S,4S)-4-hydroxytetrahydro-2H-pyran-3-yl]carbamate.

To a solution of the above compound (90.5 g, 0.360 mol) in 1.8 L of methanol was added palladium hydroxide on carbon (9 g). The mixture was subjected to 40 psi of hydrogen at 25° C. for 15 h, then filtered through solka-floc. The filter cake was washed 3× with methanol (200 mL), and the combined filtrates were concentrated in vacuo to provide crude (3S,4S)-3-aminotetrahydro-2H-pyran-4-ol that gave proton NMR spectra consistent with theory.

6-Bromo-3-[(3S,4S)-4-hydroxytetrahydro-2H-pyran-3-yl]benzo[h]quinazolin-4(3H)-one was prepared employing the procedures described for the construction of 1-amino-4-bromo-N-[(3R,4S)-3-hydroxytetrahydro-2H-pyran-4-yl]-2-naphthamide in Example 1, substituting (3S,4S)-3-aminotetrahydro-2H-pyran-4-ol for (3R,4S)-3-hydroxytetrahydro-2H-pyran-4-aminium chloride.

The titled compound was prepared employing the procedures described for the construction of 1,5-anhydro-2,3-dideoxy-3-{5-[(4,4-difluoropiperidin-1-yl)methyl]-3-oxo-1,3-dihydro-2H-benzo[e]isoindol-2-yl}-L-threo-pentitol in Example 7, substituting (3S,4S)-3-aminotetrahydro-2H-pyran-4-ol for (3R,4S)-4-aminotetrahydro-2H-pyran-3-ol. The resultant white solid gave proton NMR spectra consistent with theory and a mass ion (ES+) of 418.1932 for [M+H]+ [calc'd for $C_{22}H_{26}F_2N_3O_3$, [M+H]+=418.1937]: $^1$H NMR (400 MHz, CDCl$_3$) δ 8.99-8.97 (m, 1H), 8.68-8.65 (m, 1H), 7.76 (s, 1H), 7.55-7.51 (m, 1H), 5.01-4.86 (m, 2H), 4.42-4.35 (m, 1H), 4.21-4.16 (m, 1H), 4.09-4.04 (m, 1H), 3.91-3.82 (m, 3H), 3.59-3.52 (m, 1H), 3.39-3.29 (m, 2H), 2.57 (br s, 4H), 2.10-1.89 (m, 6H) ppm.

Example 9

5-[(4-Ethenyl-4-fluoropiperidin-1-yl)methyl]-8-[(1S,2S)-2-hydroxycyclohexyl]-8,9-dihydro-7H-pyrrolo[3,4-h]quinolin-7-one

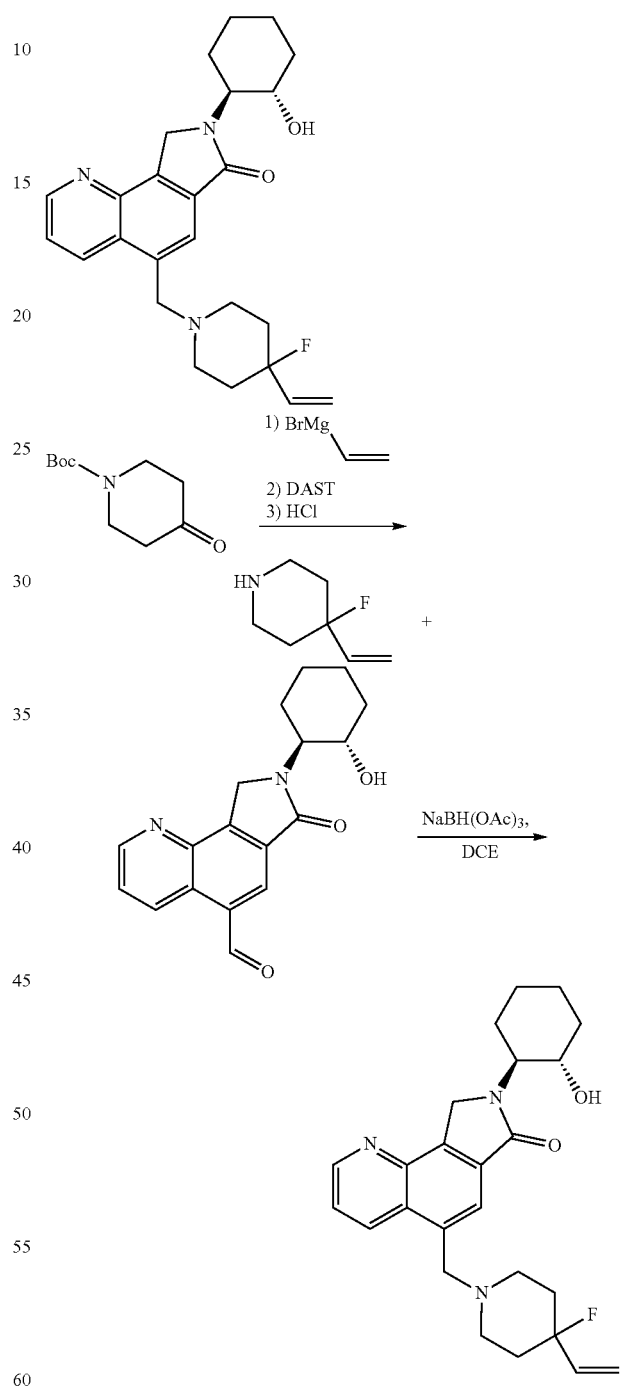

To a solution of tert-butyl 4-oxopiperidine-1-carboxylate (1.00 g, 5.02 mmol) in 20 mL of dichloromethane at 0° C. under an atmosphere of nitrogen was added vinylmagnesium bromide (0.7 M dichloromethane solution, 9.32 mL, 6.52 mmol) dropwise. After 1 hr, the mixture was treated with water and extracted 3× with ethyl acetate. The combined organic extracts were dried with sodium sulfate, filtered and concentrated in vacuo. The residue was purified via silica gel chromatography, eluting with 0-60% ethyl acetate in hexanes, to provide tert-butyl 4-ethenyl-4-hydroxypiperidine-1-carboxylate that gave a proton NMR spectra consistent with theory.

To a solution of the above compound (0.250 g, 1.10 mmol) in 15 mL of dichloromethane at 0° C. under an atmosphere of nitrogen was treated with N-ethyl-N-(trifluorosulfanyl)ethanamine (DAST, 0.19 mL, 1.4 mmol). After 30 min, the mixture was diluted with dichloromethane and treated with saturated aqueous sodium bicarbonate. The mixture was partitioned and the aqueous layer was extracted 2× with ethyl acetate. The combined organic extracts were dried with sodium sulfate, filtered, and concentrated in vacuo. The residue was purified via silica gel chromatography, eluting with 0-100% ethyl acetate in hexanes, to provide tert-butyl 4-cyclopropyl-4-fluoropiperidine-1-carboxylate that gave a proton NMR spectra consistent with theory.

The titled compound was prepared employing the procedures described for the construction of 1-({2-[(1S,2S)-2-hydroxycyclohexyl]-3-oxo-2,3-dihydro-1H-benzo[e]isoindol-5-yl}methyl)-4-(pyridine-2-yl)piperidine-4-carbonitrile in Example 1, substituting tert-butyl 4-cyclopropyl-4-fluoropiperidine-1-carboxylate for tert-butyl 4-cyano-4-pyridin-2-ylpiperidine-1-carboxylate, and substituting 5-bromo-8-[(1S,2S)-2-hydrocyclohexyl]-3,9-dihydro-7H-pyrrolo[3,4-h]quinolin-7-one for 2-[(1S,2S)-2-hydroxycyclohexyl]-3-oxo-2,3-dihydro-1H-benzo[e]isoindole-5-carbaldehyde. The resultant white solid gave proton NMR spectra consistent with theory and a mass ion (ES+) of 424.2388 for [M+H]+ [calc'd for $C_{25}H_{31}FN_3O_2$, [M+H]+=424.2395]: $^1$H NMR (400 MHz, CDCl$_3$) δ 8.98-8.97 (m, 1H), 8.83-8.81 (m, 1H), 7.83 (s, 1H), 7.57-7.54 (m, 1H), 5.52 (br s, 1H), 4.99-4.80 (m, 3H), 4.23-3.79 (m, 2H), 3.78-3.62 (m, 3H), 2.62 (br s, 1H), 2.36-2.20 (m, 3H), 2.05-1.84 (m, 2H), 1.71-1.30 (m, 7H) ppm.

Example 10

3-{5-[(4,4-Difluoropiperidin-1-yl)methyl]-7-oxo-7,9-dihydro-8H-pyrrolo[3,4-h]quinolin-8-yl}phenyl dimethylcarbamate

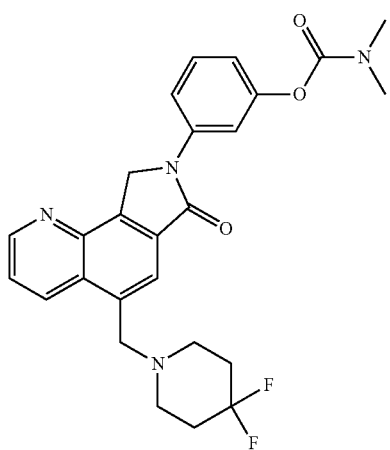

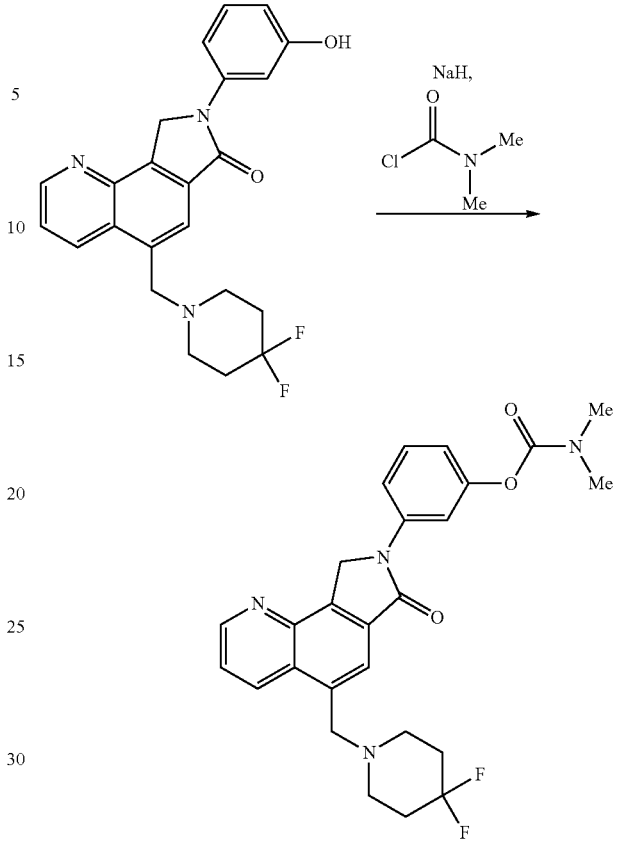

5-[(4,4-Difluoropiperidin-1-yl)methyl]-8-(3-hydroxyphenyl)-8,9-dihydro-7H-pyrrolo[3,4-h]quinolin-7-one was prepared employing the procedures described for the construction of 1-({2-[(1S,2S)-2-hydroxycyclohexyl]-3-oxo-2,3-dihydro-1H-benzo[e]isoindol-5-yl}methyl)-4-(pyridine-2-yl)piperidine-4-carbonitrile in Example 1, substituting 3-aminophenol for (1S,2S)-2-aminocyclohexanol, substituting tert-butyl 4,4-difluoropiperidine-1-carboxylate for tert-butyl 4-cyano-4-pyridin-2-ylpiperidine-1-carboxylate, and substituting 5-bromo-8-[(1S,2S)-2-hydrocyclohexyl]-3,9-dihydro-7H-pyrrolo[3,4-h]quinolin-7-one for 2-[(1S, hydroxycyclohexyl]-3-oxo-2,3-dihydro-1H-benzo[e]isoindole-5-carbaldehyde.

To a solution of 5-[(4,4-difluoropiperidin-1-yl)methyl]-8-(3-hydroxyphenyl)-8,9-dihydro-7H-pyrrolo[3,4-h]quinolin-7-one (0.070 g, 0.17 mmol) in 3 mL of dimethylsulfoxide was added sodium hydride (0.034 g, 0.86 mmol). After 5 min, dimethyl carbamyl chloride (0.047 mL, 0.51 mmol) was added. The mixture was stirred at ambient temperature for 15 hr, diluted with ethyl acetate, washed 3× with brine, dried with sodium sulfate, filtered, and concentrated in vacuo. The residue was purified via preparative reverse phase HPLC to provide the title compound that gave a proton NMR spectra consistent with theory and a mass ion (ES+) of 481.2066 for [M+H]+ [Calc'd for $C_{26}H_{27}F_2N_4O_3$, [M+H]+=481.2046].

The following compounds in Table 1 were prepared according to referenced procedure, and in the Examples above. The starting materials are either commercially available or known in the literature, or may be prepared from commercially available reagents using conventional reactions well known in the art.

TABLE 1

| Compd # | R¹ | R² | R³, R⁴ | M1 Pot. | Compound Name | HRMS/ LRMS | Method |
|---|---|---|---|---|---|---|---|
| 11 | 2-hydroxycyclohexyl | piperidin-1-ylmethyl | H, H | 4900 | 2-(2-Hydroxycyclohexyl)-5-piperidin-1-ylmethyl-1,2-dihydro-3H-benzo[e]isoindol-3-one | $C_{24}H_{31}N_2O_2$ Obs. 379.2374 Calc 379.2380 | Ex 1 |
| 12 | (1S,2S)-2-hydroxycyclohexyl | (4-methylpiperazin-1-yl)methyl | H, H | 1300 | 2-[(1S,2S)-2-hydroxycyclohexyl]-5-[(4-methylpiperazin-1-yl)methyl]-1,2-dihydro-3H-benzo[e]isoindol-3-one | $C_{24}H_{32}N_3O_2$ Obs. 394.2489 Calc 394.2489 | Ex 1 |
| 13 | (1S,2S)-2-hydroxycyclohexyl | (4-methyl-3-oxopiperazin-1-yl)methyl | H, H | 560 | 2-[(1S,2S)-2-hydroxycyclohexyl]-5-[(4-methyl-3-oxopiperazin-1-yl)methyl]-1,2-dihydro-3H-benzo[e]isoindol-3-one | $C_{24}H_{29}N_3O_3$ Obs. 408.2273 Calc 404.2282 | Ex 1 |
| 14 | 2-hydroxycyclohexyl | (4-acetylpiperazin-1-yl)methyl | H, H | 2600 | 5-[(4-acetylpiperazin-1-yl)methyl]-2-(2-hydroxycyclohexyl)-1,2-dihydro-3H-benzo[e]isoindol-3-one | $C_{25}H_{32}N_3O_3$ Obs. 422.2429 Calc 422.2438 | Ex 1 |
| 15 | 2-hydroxycyclohexyl | {4-(methylsulfonyl)piperazin-1-yl}methyl | H, H | 720 | 2-(2-hydroxycyclohexyl)-5-{[4-(methylsulfonyl)piperazin-1-yl]methyl}-1,2-dihydro-3H-benzo[e]isoindol-3-one | $C_{24}H_{32}N_3O_4S$ Obs. 458.2096 Calc 458.2108 | Ex 1 |
| 16 | 2-hydroxycyclohexyl | (3-methylpiperidin-1-yl)methyl | H, H | 7800 | 2-(2-hydroxycyclohexyl)-5-[(3-methylpiperidin-1-yl)methyl]-1,2-dihydro-3H-benzo[e]isoindol-3-one | $C_{25}H_{33}N_2O_2$ Obs. 393.2527 Calc 393.2537 | Ex 1 |

TABLE 1-continued

| Compd # | R¹ | R² | R³, R⁴ | M1 Pot. | Compound Name | HRMS/LRMS | Method |
|---|---|---|---|---|---|---|---|
| 17 | 2-hydroxycyclohexyl | (3-fluoropiperidin-1-yl)methyl | H, H | 320 | 5-[(3-fluoropiperidin-1-yl)methyl]-2-(2-hydroxycyclohexyl)-1,2-dihydro-3H-benzo[e]isoindol-3-one | $C_{24}H_{30}FN_2O_2$ Obs. 397.2282 Calc 397.2286 | Ex 1 |
| 18 | 2-hydroxycyclohexyl | (3,3-difluoropiperidin-1-yl)methyl | H, H | 160 | 5-[(3,3-difluoropiperidin-1-yl)methyl]-2-(2-hydroxycyclohexyl)-1,2-dihydro-3H-benzo[e]isoindol-3-one | $C_{24}H_{29}F_2N_2O_2$ Obs. 415.2188 Calc 415.2192 | Ex 1 |
| 19 | 2-hydroxycyclohexyl | (4-cyano-4-fluoropiperidin-1-yl)methyl | H, H | 37 | 4-fluoro-1-({2-[(1S,2S)-2-hydroxycyclohexyl]-3-oxo-2,3-dihydro-1H-benzo[e]isoindol-5-yl}methyl)piperidine-4-carbonitrile | $C_{25}H_{29}FN_3O_2$ Obs. 422.2230 Calc 422.2238 | Ex 9 |
| 20 | 2-hydroxycyclohexyl | (4-cyanopiperidin-1-yl)methyl | H, H | 93 | 1-({2-[1S,2S)-2-hydroxycyclohexyl]-3-oxo-2,3-dihydro-1H-benzo[e]isoindol-5-yl}methyl)piperidine-4-carbonitrile | $C_{25}H_{30}N_3O_2$ Obs. 404.2326 Calc 404.2333 | Ex 1 |
| 21 | 2-hydroxycyclohexyl | (4-methylpiperidin-1-yl)methyl | H, H | 1500 | 2-[(1S,2S)-2-hydroxycyclohexyl]-5-[(4-methylpiperidin-1-yl)methyl]-1,2-dihydro-3H-benzo[e]isoindol-3-one | $C_{25}H_{33}N_2O_2$ Obs. 393.2538 Calc 393.2537 | Ex 1 |
| 22 | 2-hydroxycyclohexyl | (4-hydroxypiperidin-1-yl)methyl | H, H | 480 | 2-(2-hydroxycyclohexyl)-5-[(4-hydroxypiperidin-1-yl)methyl]-1,2-dihydro-3H-benzo[e]isoindol-3-one | $C_{29}H_{32}N_5O_2$ Obs 395.2329 Calc 395.2329 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 23 | cyclohexyl-OH | CH₂-pyrrolidin-1-yl | H, H | 3800 | 2-(2-Hydroxycyclohexyl)-5-(pyrrolidin-1-ylmethyl)-1,2-dihydro-3H-benzo[e]isoindol-3-one | $C_{23}H_{29}N_2O_2$ Obs 365.2222 Calc 365.2224 | Ex 1 |
| 24 | cyclohexyl-OH | CH₂-morpholin-4-yl | H, H | 150 | 2-(2-hydroxycyclohexyl)-5-(morpholin-4-ylmethyl)-1,2-dihydro-3H-benzo[e]isoindol-3-one | $C_{23}H_{29}N_2O_3$ Obs 381.2174 Calc 381.2173 | Ex 1 |
| 25 | cyclohexyl-OH | CH₂-(4,4-difluoropiperidin-1-yl) | H, H | 12 | 5-[(4,4-difluoropiperidin-1-yl)methyl]-2-(2-hydroxycyclohexyl)-1,2-dihydro-3H-benzo[e]isoindol-3-one | $C_{24}H_{29}F_2N_2O_2$ Obs 415.2195 Calc 415.2192 | Ex 1 |
| 26 | cyclohexyl-OH | CH₂-(4-fluoropiperidin-1-yl) | H, H | 160 | 5-[(4-fluoropiperidin-1-yl)methyl]-2-(2-hydroxycyclohexyl)-1,2-dihydro-3H-benzo[e]isoindol-3-one | $C_{24}H_{30}FN_2O_2$ Obs 397.2288 Calc 397.2286 | Ex 1 |
| 27 | cyclohexyl-OH | CH₂-[4-(trifluoromethyl)piperidin-1-yl] | H, H | 360 | 2-(2-hydroxycyclohexyl)-5-{[4-(trifluoromethyl)piperidin-1-yl]methyl}-1,2-dihydro-3H-benzo[e]isoindol-3-one | $C_{25}H_{30}F_3N_2O_2$ Obs 447.2257 Calc 447.2254 | Ex 1 |
| 28 | cyclohexyl-OH | CH₂-(3-fluoro-4-hydroxypyrrolidin-1-yl) | H, H | 1200 | 5-[(3-fluoro-4-hydroxypyrrolidin-1-yl)methyl]-2-(2-hydroxycyclohexyl)-1,2-dihydro-3H-benzo[e]isoindol-3-one | $C_{23}H_{28}FN_2O_3$ Obs 399.2073 Calc 399.2078 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 29 | 2-hydroxycyclohexyl | (trans-3,4-difluoropyrrolidin-1-yl)methyl | H, H | 240 | 5-{[trans-3,4-difluoropyrrolidin-1-yl]methyl}-2-(2-hydroxycyclohexyl)-1,2-dihydro-3H-benzo[e]isoindol-3-one | $C_{23}H_{27}F_2N_2O_2$ Obs 401.2035 Calc 401.2035 | Ex 1 |
| 30 | 2-hydroxycyclohexyl | [2-(trifluoromethyl)pyrrolidin-1-yl]methyl | H, H | 2700 | 2-(2-hydroxycyclohexyl)-5-{[2-(trifluoromethyl)pyrrolidin-1-yl]methyl}-1,2-dihydro-3H-benzo[e]isoindol-3-one | $C_{24}H_{28}F_3N_2O_2$ Obs 433.2102 Calc 433.2097 | Ex 1 |
| 31 | 2-hydroxycyclohexyl | [3-(fluoromethyl)pyrrolidin-1-yl]methyl | H, H | 2300 | 5-{[3-(fluoromethyl)pyrrolidin-1-yl]methyl}-2-(2-hydroxycyclohexyl)-1,2-dihydro-3H-benzo[e]isoindol-3-one | $C_{24}H_{30}FN_2O_2$ Obs 397.2285 Calc 397.2286 | Ex 1 |
| 32 | 2-hydroxycyclohexyl | [(3S)-3-fluoropyrrolidin-1-yl]methyl | H, H | 1800 | 5-{[(3S)-3-fluoropyrrolidin-1-yl]methyl}-2-(2-hydroxycyclohexyl)-1,2-dihydro-3H-benzo[e]isoindol-3-one | $C_{23}H_{28}FN_2O_2$ Obs 383.2128 Calc 383.2129 | Ex 1 |
| 33 | 2-hydroxycyclohexyl | (3,3-difluoropyrrolidin-1-yl)methyl | H, H | 240 | 5-[(3,3-difluoropyrrolidin-1-yl)methyl]-2-(2-hydroxycyclohexyl)-1,2-dihydro-3H-benzo[e]isoindol-3-one | $C_{23}H_{27}F_2N_2O_2$ Obs 401.2034 Calc 401.2035 | Ex 1 |
| 34 | 2-hydroxycyclohexyl | {[4-(2,2,2-trifluoroethyl)piperazin-1-yl]methyl} | H, H | 1900 | 2-(2-hydroxycyclohexyl)-5-{[4-(2,2,2-trifluoroethyl)piperazin-1-yl]methyl}-1,2-dihydro-3H-benzo[e]isoindol-3-one | $C_{25}H_{31}F_3N_3O_2$ Obs 462.2367 Calc 462.2363 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 35 | 2-hydroxycyclohexyl | piperidin-1-ylmethyl with 4-F and 4-CO₂Et | H, H | 240 | ethyl 4-fluoro-1-{[2-(2-hydroxycyclohexyl)-3-oxo-2,3-dihydro-1H-benzo[e]isoindol-5-yl]methyl}piperidine-4-carboxylate | $C_{27}H_{34}N_2O_3$ Obs 469.2500 Calc 469.2497 | Ex 1 |
| 36 | 2-hydroxycyclohexyl | (2-oxa-7-azaspiro[3.5]non-7-yl)methyl | H, H | 840 | 2-(2-hydroxycyclohexyl)-5-(2-oxa-7-azaspiro[3.5]non-7-ylmethyl)-1,2-dihydro-3H-benzo[e]isoindol-3-one | $C_{26}H_{34}FN_2O_4$ Obs 421.2489 Calc 421.2486 | Ex 1 |
| 37 | 2-hydroxycyclohexyl | (4-hydroxy-4-methylpiperidin-1-yl)methyl | H, H | >1100 | 2-(2-hydroxycyclohexyl)-5-[(4-hydroxy-4-methylpiperidin-1-yl)methyl]-1,2-dihydro-3H-benzo[e]isoindol-3-one | $C_{25}H_{33}N_2O_3$ Obs 409.2484 Calc 409.2486 | Ex 1 |
| 38 | 2-hydroxycyclohexyl | (4,4-dimethylpiperidin-1-yl)methyl | H, H | 670 | 5-[(4,4-dimethylpiperidin-1-yl)methyl]-2-(2-hydroxycyclohexyl)-1,2-dihydro-3H-benzo[e]isoindol-3-one | $C_{26}H_{35}N_2O_2$ Obs 407.2693 Calc 407.2693 | Ex 1 |
| 39 | 2-hydroxycyclohexyl | (4-cyclopropylpiperidin-1-yl)methyl | H, H | 5300 | 5-[(4-cyclopropylpiperidin-1-yl)methyl]-2-(2-hydroxycyclohexyl)-1,2-dihydro-3H-benzo[e]isoindol-3-one | $C_{27}H_{35}N_2O_2$ Obs 419.2695 Calc 419.2693 | Ex 1 |
| 40 | 2-hydroxycyclohexyl | 1'H-spiro[1-benzofuran-3,4'-piperidin]-1'-ylmethyl | H, H | 720 | 2-(2-hydroxycyclohexyl)-5-(1'H-spiro[1-benzofuran-3,4'-piperidin]-1'-ylmethyl)-1,2-dihydro-3H-benzo[e]isoindol-3-one | $C_{31}H_{35}N_2O_3$ Obs 483.2640 Calc 483.2642 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 41 | cyclohexyl-OH | 4-phenylpiperidin-1-ylmethyl | H, H | 1400 | 2-(2-hydroxycyclohexyl)-5-[(4-phenylpiperidin-1-yl)methyl]-1,2-dihydro-3H-benzo[e]isoindol-3-one | $C_{30}H_{35}N_2O_2$ Obs 455.2379 Calc 455.2693 | Ex 1 |
| 42 | cyclohexyl-OH | 4-(4-pyridinyl)piperidin-1-ylmethyl | H, H | 240 | 2-(2-hydroxycyclohexyl)-5-[(4-(4-pyridinyl)piperidin-1-yl)methyl]-1,2-dihydro-3H-benzo[e]isoindol-3-one | $C_{29}H_{35}N_3O_2$ Obs 456.2639 Calc 456.2646 | Ex 1 |
| 43 | cyclohexyl-OH | 4-hydroxy-4-pyridin-4-ylpiperidin-1-ylmethyl | H, H | 830 | 2-(2-hydroxycyclohexyl)-5-[(4-hydroxy-4-pyridin-4-ylpiperidin-1-yl)methyl]-1,2-dihydro-3H-benzo[e]isoindol-3-one | $C_{29}H_{34}N_3O_3$ Obs 472.2596 Calc 472.2595 | Ex 1 |
| 44 | cyclohexyl-OH | 4-CN-4-(pyridin-2-yl)piperidin-1-ylmethyl | Me, H | 9.6 | 1-({2-[(1S,2S)-2-hydroxycyclohexyl]-1-methyl-3-oxo-2,3-dihydro-1H-benzo[e]isoindol-5-yl}methyl)-4-(pyridin-2-yl)piperidine-4-carbonitrile | $C_{31}H_{35}N_4O_2$ Obs 495.2756 Calc 495.2755 | Ex 3 |
| 45 | cyclohexyl-OH | 4-CN-4-(pyridin-2-yl)piperidin-1-ylmethyl | Me, H | 272 | 1-({2-[(1S,2S)-2-hydroxycyclohexyl]-1-methyl-3-oxo-2,3-dihydro-1H-benzo[e]isoindol-5-yl}methyl)-4-(pyridin-2-yl)piperidine-4-carbonitrile | 495.2755 Calc 495.2755 $C_{31}H_{35}N_4O_2$ | Ex 3 |

TABLE 1-continued

| Compd # | R¹ | R² | R³, R⁴ | M1 Pot. | Compound Name | HRMS/LRMS | Method |
|---|---|---|---|---|---|---|---|
| 46 | 2-hydroxycyclohexyl (1R,2R) | 1-(piperidin-4-yl)-4-(pyridin-2-yl)-4-carbonitrile, N-CH₂ linker | H, H | 539 | 1-({2-[(1R,2R)-2-hydroxycyclohexyl]-3-oxo-2,3-dihydro-1H-benzo[e]isoindol-5-yl}methyl)-4-pyridin-2-ylpiperidine-4-carbonitrile | $C_{30}H_{32}N_4O_2$ Obs 481.5 Calc'd 481.3 | Ex 1 |
| 47 | 2-hydroxycyclohexyl (1R,2S) | 1-(piperidin-4-yl)-4-(pyridin-2-yl)-4-carbonitrile, N-CH₂ linker | H, H | 147 | 1-({2-[(1R,2S)-2-hydroxycyclohexyl]-3-oxo-2,3-dihydro-1H-benzo[e]isoindol-5-yl}methyl)-4-pyridin-2-ylpiperidine-4-carbonitrile | $C_{30}H_{32}N_4O_2$ Obs 481.5 Calc'd 481.3 | Ex 1 |
| 48 | 2-hydroxycyclohexyl (1S,2S) | 1-(piperidin-4-yl)-4-(6-chloropyridin-2-yl)-4-carbonitrile, N-CH₂ linker | H, H | 53 | 4-(6-chloropyridin-2-yl)-1-{2-[(1S,2S)-2-hydroxycyclohexyl]-3-oxo-2,3-dihydro-1H-benzo[e]isoindol-5-yl}methyl)piperidine-4-carbonitrile | $C_{30}H_{32}ClN_4O_2$ Obs 515.2221 Calc 515.2208 | Ex 1 |
| 49 | 2-hydroxycyclohexyl (1S,2S) | 1-(piperidin-4-yl)-4-(6-ethenylpyridin-2-yl)-4-carbonitrile, N-CH₂ linker | H, H | 114 | 4-(6-ethenylpyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile | $C_{32}H_{35}N_4O_2$ Obs 507.2758 Calc 507.2755 | Ex 4 |

TABLE 1-continued

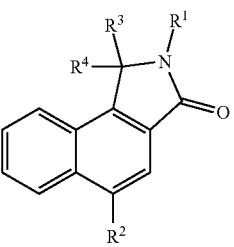

| Compd # | R¹ | R² | R³, R⁴ | M1 Pot. | Compound Name | HRMS/ LRMS | Method |
|---|---|---|---|---|---|---|---|
| 50 | 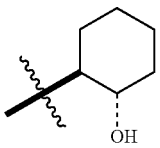 [SMILES: *[C@H]1CCCC[C@@H]1O] | 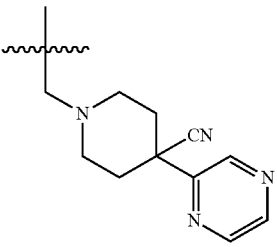 [SMILES: *CN1CCC(C#N)(c2cnccn2)CC1] | H, H | 31 | 1-({2-[(1S,2S)-2-hydroxycyclohexyl]-3-oxo-2,3-dihydro-1H-benzo[e]isoindol-5-yl}methyl)-4-(pyrazin-2-yl)piperidine-4-carbonitrile | $C_{29}H_{32}N_5O_2$ Obs 482.2555 Calc 482.2551 | Ex 1 |
| 51 | 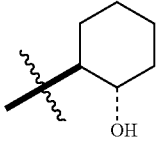 [SMILES: *[C@H]1CCCC[C@@H]1O] | 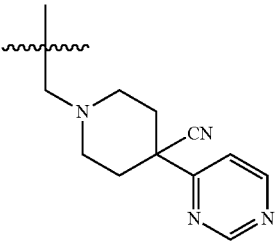 | H, H | 17 | 1-({2-[(1S,2S)-2-hydroxycyclohexyl]-3-oxo-2,3-dihydro-1H-benzo[e]isoindol-5-yl}methyl)-4-(pyrimidin-4-yl)piperidine-4-carbonitrile | $C_{29}H_{32}N_5O_2$ Obs 482.2555 Calc 482.2551 | Ex 1 |
| 52 | 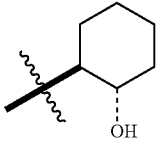 [SMILES: *[C@H]1CCCC[C@@H]1O] | 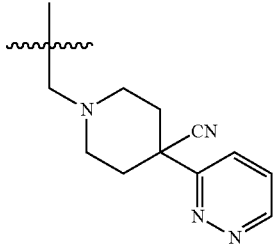 [SMILES: *CN1CCC(C#N)(c2cccnn2)CC1] | H, H | 27 | 1-({2-[(1S,2S)-2-hydroxycyclohexyl]-3-oxo-2,3-dihydro-1H-benzo[e]isoindol-5-yl}methyl)-4-(pyridazin-3-yl)piperidine-4-carbonitrile | $C_{29}H_{32}N_5O_2$ Obs 482.2555 Calc 482.2551 | Ex 1 |
| 53 | 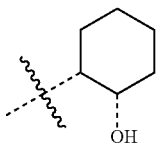 [SMILES: *[C@@H]1CCCC[C@@H]1O] | 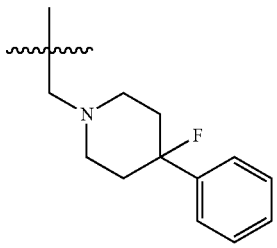 | H, H | 248 | 5-[(4-fluoro-4-phenylpiperidin-1-yl)methyl]-2-[(1R,2R)-2-hydroxycyclohexyl]-1,2-dihydro-3H-benzo[e]isoindol-3-one | $C_{30}H_{34}FN_2O_2$ Obs 473.2601 Calc 473.2599 | Ex 2 |
| 54 | 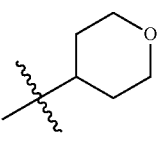 | 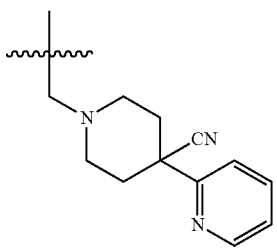 | H, H | 279 | 1-{[3-oxo-2-(tetrahydro-2H-pyran-4-yl)-2,3-dihydro-1H-benzo[e]isoindol-5-yl]methyl}-4-pyridin-2-ylpiperidine-4-carbonitrile | $C_{29}H_{31}N_4O_2$ Obs 467.2447 Calc 467.2442 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 55 | tetrahydro-2H-pyran-3-yl | piperidine with CN and pyridin-2-yl | H, H | 1497 | 1-{[3-oxo-2-(tetrahydro-2H-pyran-3-yl)-2,3-dihydro-1H-benzo[e]isoindol-5-yl]methyl}-4-pyridin-2-ylpiperidine-4-carbonitrile | $C_{29}H_{31}N_4O_2$ Obs 467.2449 Calc 467.2442 | Ex 1 |
| 56 | (1S,2S)-2-hydroxycyclohexyl | piperidine with CN and phenyl | H, H | 83 | 1-({2-[(1S,2S)-2-hydroxycyclohexyl]-3-oxo-2,3-dihydro-1H-benzo[e]isoindol-5-yl}methyl)-4-phenylpiperidine-4-carbonitrile | $C_{31}H_{34}N_3O_2$ Obs 480.2657 Calc 480.2646 | Ex 1 |
| 57 | (1S,2S)-2-hydroxycyclohexyl | piperidine with CN and pyridin-3-yl | H, H | 22 | 1-{2-[(1S,2S)-2-hydroxycyclohexyl]-3-oxo-2,3-dihydro-1H-benzo[e]isoindol-5-yl}methyl)-4-pyridin-3-ylpiperidine-4-carbonitrile | $C_{30}H_{33}N_4O_2$ Obs 481.2600 Calc 481.2598 | Ex 1 |
| 58 | (1S,2S)-2-hydroxycyclohexyl | piperidine with CN and pyridin-4-yl | H, H | 21 | 1-({2-[(1S,2S)-2-hydroxycyclohexyl]-3-oxo-2,3-dihydro-1H-benzo[e]isoindol-5-yl}methyl)-4-pyridin-4-ylpiperidine-4-carbonitrile | $C_{30}H_{33}N_4O_2$ Obs 481.2602 Calc 481.2598 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 59 | 2-hydroxycyclohexyl (1S,2S) | 1-methyl-4-(2-chlorophenyl)-piperidine-4-carbonitrile | H, H | 46 | 4-(2-chlorophenyl)-1-({2-[(1S,2S)-2-hydroxycyclohexyl]-3-oxo-2,3-dihydro-1H-benzo[e]isoindol-5-yl}methyl)piperidine-4-carbonitrile | C₃₁H₃₃ClN₃O₂ Obs 514.2256 Calc 514.2256 | Ex 1 |
| 60 | 2-hydroxycyclohexyl (1R,2S) | 1-methyl-4-(2-fluorophenyl)-piperidine-4-carbonitrile | H, H | 44 | 4-(2-fluorophenyl)-1-({2-[(1R,2S)-2-hydroxycyclohexyl]-3-oxo-2,3-dihydro-1H-benzo[e]isoindol-5-yl}methyl)piperidine-4-carbonitrile | C₃₁H₃₃FN₃O₂ Obs 498.2569 Calc 498.2551 | Ex 1 |
| 61 | 2-hydroxycyclohexyl (1R,2S) | 1-methyl-4-(2-methylphenyl)-piperidine-4-carbonitrile | H, H | 107 | 1-({2-[(1R,2S)-2-hydroxycyclohexyl]-3-oxo-2,3-dihydro-1H-benzo[e]isoindol-5-yl}methyl)-4-(2-methylphenyl)piperidine-4-carbonitrile | C₃₂H₃₆N₃O₂ Obs 494.2809 Calc 494.2802 | Ex 1 |
| 62 | 2-fluorophenyl | 1-methyl-4-(pyridin-2-yl)-piperidine-4-carbonitrile | H, H | 650 | 1-{[2-(2-fluorophenyl)-3-oxo-2,3-dihydro-1H-benzo[e]isoindol-5-yl]methyl}-4-pyridin-2-ylpiperidine-4-carbonitrile | C30H25FN4O Obs 76.9 Calc 477.2 | Ex 1 |
| 63 | 2-fluorophenyl | 1-methyl-4-(4-methylpyridin-2-yl)-piperidine-4-carbonitrile | H, H | 545 | 1-{[2-(2-fluorophenyl)-3-oxo-2,3-dihydro-1H-benzo[e]isoindol-5-yl]methyl}-4-(4-methylpyridin-2-yl)piperidine-4-carbonitrile | — | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 64 | 2-hydroxycyclohexyl | 1-methylene-4-(4-methylpyridin-2-yl)-4-cyanopiperidine | H, H | 9.7 | 1-({2-[(1S,2S)-2-hydroxycyclohexyl]-3-oxo-2,3-dihydro-1H-benzo[e]isoindol-5-yl}methyl)-4-(4-methylpyridin-2-yl)piperidine-4-carbonitrile | C₃₁H₃₅N₄O₂ Obs 495.2762 Calc 495.2755 | Ex 1 |
| 65 | 2-fluorophenyl | [1-(pyridin-4-yl)-3,4-dihydroisoquinolin-2(1H)-yl]methyl | H, H | 1367 | 2-(2-fluorophenyl)-5-{[1-(pyridin-4-yl)-3,4-dihydroisoquinolin-2(1H)-yl]methyl}-1,2-dihydro-3H-benzo[e]isoindol-3-one | — | Ex 1 |
| 66 | 2-fluorophenyl | [4-(1-methyl-1H-pyrazol-4-yl)piperazin-1-yl]methyl | H, H | 273 | 2-(2-fluorophenyl)-5-{[4-(1-methyl-1H-pyrazol-4-yl)piperazin-1-yl]methyl}-1,2-dihydro-3H-benzo[e]isoindol-3-one | — | Ex 1 |
| 67 | 2-hydroxycyclohexyl | [4-(4-fluorophenyl)piperazin-1-yl]methyl | H, H | 67 | 5-{[4-(4-fluorophenyl)piperazin-1-yl]methyl}-2-[(1S,2S)-2-hydroxycyclohexyl]-1,2-dihydro-3H-benzo[e]isoindol-3-one | C₂₉H₃₃FN₃O₂ Obs 474.2555 Calc 474.2551 | Ex 1 |
| 68 | 2-hydroxycyclohexyl | {4-[4-(methylsulfonyl)phenyl]piperazin-1-yl}methyl | H, H | 47 | 2-[(1S,2S)-2-hydroxycyclohexyl]-5-({4-[4-(methylsulfonyl)phenyl]piperazin-1-yl}methyl)-1,2-dihydro-3H-benzo[e]isoindol-3-one | C₃₀H₃₆N₃O₄S Obs 534.2434 Calc 534.2421 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 69 | cyclohexyl-OH (1S,2S) | CH₂-piperazinyl-(4-methoxyphenyl) | H, H | 49 | 2-[(1S,2S)-2-hydroxycyclohexyl]-5-{[4-(4-methoxyphenyl)piperazin-1-yl]methyl}-1,2-dihydro-3H-benzo[e]isoindol-3-one | $C_{30}H_{36}N_3O_2$ Obs 486.2758 Calc 486.2751 | Ex 1 |
| 70 | cyclohexyl-OH (1S,2S) | CH₂-(2-methylpiperazinyl)-(4-methoxyphenyl) | H, H | 150 | 2-[(1S,2S)-2-hydroxycyclohexyl]-5-{[4-(4-methoxyphenyl)-2-methylpiperazin-1-yl]methyl}-1,2-dihydro-3H-benzo[e]isoindol-3-one | $C_{31}H_{38}N_3O_3$ Obs 500.2910 Calc 500.2908 | Ex 1 |
| 71 | cyclohexyl-OH (1S,2S) | CH₂-(2,5-diazabicyclo[2.2.1]heptyl)-(4-methoxyphenyl) | H, H | 315 | 2-[(1S,2S)-2-hydroxycyclohexyl]-5-{[5-(4-methoxyphenyl)-2,5-diazabicyclo[2.2.1]hept-2-yl]methyl}-1,2-dihydro-3H-benzo[e]isoindol-3-one | $C_{31}H_{36}N_3O_3$ Obs 498.2759 Calc 498.2751 | Ex 1 |
| 72 | cyclohexyl-OH (1S,2S) | CH₂-(4-phenylpiperazinyl) | H, H | 72 | 2-[(1S,2S)-2-hydroxycyclohexyl]-5-[(4-phenylpiperazin-1-yl)methyl]-1,2-dihydro-3H-benzo[e]isoindol-3-one | $C_{29}H_{34}N_3O_2$ Obs 456.2651 Calc 456.2646 | Ex 1 |
| 73 | cyclohexyl-OH (1S,2S) | CH₂-(4-phenylpiperazinyl) | H, Me | 198 | 2-[(1R,2S)-2-hydroxycyclohexyl]-1-methyl-5-[(4-phenylpiperazin-1-yl)methyl]-1,2-dihydro-3H-benzo[e]isoindol-3-one | $C_{30}H_{36}N_3O_2$ Obs 470.2818 Calc 470.2802 | Ex 3 |

TABLE 1-continued

| Compd # | R¹ | R² | R³, R⁴ | M1 Pot. | Compound Name | HRMS/ LRMS | Method |
|---|---|---|---|---|---|---|---|
| 74 | 2-hydroxycyclohexyl (1S,2S) | CH₂-piperazine-pyridin-2-yl | H, H | 46 | 2-[(1S,2S)-2-hydroxycyclohexyl]-5-[(4-pyridin-2-ylpiperazin-1-yl)methyl]-1,2-dihydro-3H-benzo[e]isoindol-3-one | C₂₈H₃₃N₄O₂ Obs 457.2599 Calc 457.2598 | Ex 1 |
| 75 | 2-hydroxycyclohexyl | CH₂-piperazine-pyridin-2-yl | H, Me | 78 | 2-(2-fluorophenyl)-5-{[4-(pyridin-2-yl)piperazin-1-yl]methyl}-1,2-dihydro-3H-benzo[e]isoindol-3-one | — | Ex 3 |
| 76 | 2-hydroxycyclohexyl (1S,2S) | CH₂-piperazine-pyridin-3-yl | H, H | 37 | 2-[(1S,2S)-2-hydroxycyclohexyl]-5-[(4-pyridin-3-ylpiperazin-1-yl)methyl]-1,2-dihydro-3H-benzo[e]isoindol-3-one | C₂₈H₃₃N₄O₂ Obs 457.2599 Calc 457.2598 | Ex 1 |
| 77 | 2-hydroxycyclohexyl (1S,2S) | CH₂-piperazine-pyridin-4-yl | H, H | 213 | 2-[(1S,2S)-2-hydroxycyclohexyl]-5-[(4-pyridin-4-ylpiperazin-1-yl)methyl]-1,2-dihydro-3H-benzo[e]isoindol-3-one | C₂₈H₃₃N₄O₂ Obs 457.2600 Calc 457.2598 | Ex 1 |
| 78 | 2-hydroxycyclohexyl (1S,2S) | CH₂-(3-methyl-4-phenylpiperazinyl) | H, H | 370 | 2-[(1S,2S)-2-hydroxycyclohexyl]-5-[(3-methyl-4-phenylpiperazin-1-yl)methyl]-1,2-dihydro-3H-benzo[e]isoindol-3-one | C₃₀H₃₆N₃O₂ Obs 470.2808 Calc 470.2802 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 79 | cyclohexyl-OH (1S,2S) | piperazine-N-methylpyrazole | H, H | 56 | 2-[(1S,2S)-2-hydroxycyclohexyl]-5-{[4-(1-methyl-1H-pyrazol-4-yl)piperazin-1-yl]methyl}-1,2-dihydro-3H-benzo[e]isoindol-3-one | $C_{27}H_{33}N_5O_2$ Obs 460.5 Calc 460.3 | Ex 1 |
| 80 | cyclohexyl-OH | piperazine-N-methylpyrazole | H, H | 1625 | 2-[(1S,2S)-2-hydroxycyclohexyl]-5-{[4-(1-methyl-1H-pyrazol-4-yl)piperazin-1-yl]methyl}-1,2-dihydro-3H-benzo[e]isoindol-3-one | $C_{27}H_{33}N_5O_2$ Obs 460.5 Calc 460.3 | Ex 1 |
| 81 | cyclohexyl-OH | piperazine-N-methylpyrazole | H, H | 496 | 2-[(1R,2R)-2-hydroxycyclohexyl]-5-{[4-(1-methyl-1H-pyrazol-4-yl)piperazin-1-yl]methyl}-1,2-dihydro-3H-benzo[e]isoindol-3-one | $C_{27}H_{33}N_5O_2$ Obs 460.5 Calc 460.3 | Ex 1 |
| 82 | tetrahydropyran-4-yl | piperazine-N-methylpyrazole | H, H | 1587 | 5-{[4-(1-methyl-1H-pyrazol-4-yl)piperazin-1-yl]methyl}-2-(tetrahydro-2H-pyran-4-yl)-1,2-dihydro-3H-benzo[e]isoindol-3-one | $C_{26}H_{32}N_5O_2$ Obs 446.2555 Calc 446.2551 | Ex 1 |
| 83 | tetrahydropyran-3-yl | piperazine-N-methylpyrazole | H, H | 3873 | 5-{[4-(1-methyl-1H-pyrazol-4-yl)piperazin-1-yl]methyl}-2-(tetrahydro-2H-pyran-3-yl)-1,2-dihydro-3H-benzo[e]isoindol-3-one | $C_{26}H_{32}N_5O_2$ Obs. 446.2555 Calc 446.2551 | Ex 1 |

TABLE 1-continued

| Compd # | R¹ | R² | R³, R⁴ | M1 Pot. | Compound Name | HRMS/ LRMS | Method |
|---|---|---|---|---|---|---|---|
| 84 | 2-fluorophenyl | piperazinyl-methyl linked to 4-(isoquinolin-3-yl)piperazine | H, H | 3273 | 2-(2-fluorophenyl)-5-[(4-isoquinolin-3-ylpiperazin-1-yl)methyl]-1,2-dihydro-3H-benzo[e]isoindol-3-one | $C_{32}H_{27}FN_4O$ Obs 507.2 Calc 503.2 | Ex 1 |
| 85 | 2-fluorophenyl | piperazinyl-methyl linked to 4-(1,3-benzothiazol-6-yl)piperazine | H, H | 1141 | 5-{[4-(1,3-benzothiazol-6-yl)piperazin-1-yl]methyl}-2-(2-fluorophenyl)-1,2-dihydro-3H-benzo[e]isoindol-3-one | $C_{30}H_{25}FN_4OS$ Obs 514.2 Calc 509.2 | Ex 1 |

TABLE 2

| Compd # | R¹ | R² | R³, R⁴ | M1 Pot. | Compound Name | HRMS/ LRMS | Method |
|---|---|---|---|---|---|---|---|
| 86 | (1S,2S)-2-hydroxycyclohexyl | piperidin-1-ylmethyl | H, H | 2900 | 8-[(1S,2S)-2-hydroxycyclohexyl]-5-(piperidin-1-ylmethyl)-8,9-dihydro-7H-pyrrolo[3,4-h]quinolin-7-one | $C_{23}H_{30}N_3O_2$ Obs 380.2329 Calc 380.2333 | Ex 1 |

TABLE 2-continued

| Compd # | R[1] | R[2] | R[3], R[4] | M1 Pot. | Compound Name | HRMS/ LRMS | Method |
|---|---|---|---|---|---|---|---|
| 87 | cyclohexyl-OH (1S,2S) | CH2-N(4-Me-piperidinyl) | H, H | 200 | 8-[(1S,2S)-2-hydroxy-cyclohexyl]-5-[(4-methyl-piperidin-1-yl)methyl]-8,9-dihydro-1H-pyrrolo[3,4-h]quinolin-7-one | C24H32N3O2 Obs 394.2479 Calc 394.2489 | Ex 1 |
| 88 | cyclohexyl-OH | CH2-N(Et)2 | H, H | 4000 | 5-[(diethyl-amino)methyl]-8-(2-hydroxy-cyclohexyl)-8,9-dihydro-7H-pyrrolo[3,4-h]quinolin-7-one | C22H30N3O2 Obs 368.2335 Calc 368.2333 | Ex 1 |
| 89 | cyclohexyl-OH | CH2-N(4-OH-piperidinyl) | H, H | 290 | 8-(2-hydroxy-cyclohexyl)-5-[(4-hydroxy-piperidin-1-yl)methyl]-8,9-dihydro-7H-pyrrolo[3,4-h]quinolin-7-one | C23H30N3O3 Obs 396.2281 Calc 396.2282 | Ex 1 |
| 90 | cyclohexyl-OH | CH2-N(4-cyclopropyl-piperidinyl) | H, H | 1196 | 5-[(4-cyclo-propyl-piperidin-1-yl)methyl]-8-(2-hydroxy-cyclo-hexyl)-8,9-dihydro-7H-pyrrolo[3,4-h]quinolin-7-one | C26H34N3O2 Obs 420.2647 Calc 420.2646 | Ex 1 |

TABLE 2-continued

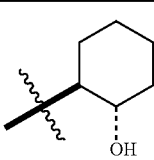

| Compd # | R¹ | R² | R³, R⁴ | M1 Pot. | Compound Name | HRMS/ LRMS | Method |
|---|---|---|---|---|---|---|---|
| 91 | 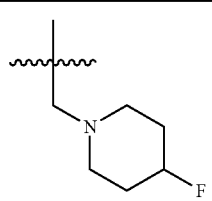 | 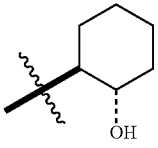 [SMILES: *[C@H]1CCCC[C@@H]1O] | H, H | 88 | 5-[(4-fluoro-piperidin-1-yl)methyl]-8-(2-hydroxy-cyclo-hexyl)-8,9-dihydro-7H-pyrrolo[3,4-h]quinolin-7-one | $C_{23}H_{29}FN_3O_2$ Obs 398.2241 Calc 398.2238 | Ex 1 |
| 92 | 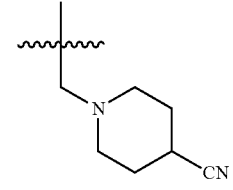 [SMILES: *CN1CCC(C#N)CC1] | 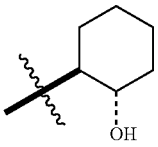 [SMILES: *[C@H]1CCCC[C@@H]1O] | H, H | 72 | 1-({8-[(1S,2S)-2-hydroxy-cyclo-hexyl]-7-oxo-8,9-dihydro-7H-pyrrolo[3,4-h]quinolin-5-yl}methyl)piperidine-4-carbonitrile | $C_{24}H_{29}N_4O_2$ Obs 405.2276 Calc 405.2285 | Ex 1 |
| 93 | 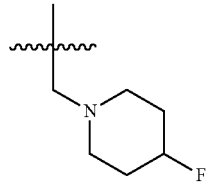 [SMILES: *CN1CCC(F)CC1] | 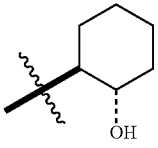 [SMILES: *[C@H]1CCCC[C@@H]1O] | H, Me | 70 | 5-[(4-fluoro-piperidin-1-yl)methyl]-8-[(1S,2S)-2-hydroxy-cyclo-hexyl]-9-methyl-8,9-dihydro-7H-pyrrolo[3,4-h]quinolin-7-one | $C_{24}H_{31}FN_3O_2$ Obs 412.4 Calc 412.2 | Ex 3 |

TABLE 2-continued

| Compd # | R¹ | R² | R³, R⁴ | M1 Pot. | Compound Name | HRMS/ LRMS | Method |
|---|---|---|---|---|---|---|---|
| 94 | cyclohexyl-OH (1S,2S) | piperidine-4-CN via CH₂ | H, Me | 51 | 1-({8-[(1S,2S)-2-hydroxy-cyclohexyl]-7-oxo-8,9-dihydro-7H-pyrrolo[3,4-h]quinolin-5-yl}methyl)piperidine-4-carbonitrile | $C_{25}H_{31}N_4O_2$ Obs 419.4 Calc 420.2 | Ex 3 |
| 95 | cyclohexyl-OH | 1'H-spiro[1-benzofuran-3,4'-piperidin]-1'-ylmethyl | H, H | 290 | 8-(2-hydroxy-cyclohexyl)-5-(1'H-spiro[1-benzofuran-3,4'-piperidin]-1'-ylmethyl)-8,9-dihydro-7H-pyrrolo[3,4-h]quinolin-7-one | $C_{30}H_{34}N_3O_3$ Obs 484.2591 Calc 484.2595 | Ex 1 |
| 96 | cyclohexyl-OH | 2-oxa-7-azaspiro[3.5]non-7-ylmethyl | H, H | 620 | 8-(2-hydroxy-cyclohexyl)-5-(2-oxa-7-azaspiro[3.5]non-7-ylmethyl)-8,9-dihydro-7H-pyrrolo[3,4-h]quinolin-7-one | $C_{25}H_{32}N_3O_2$ Obs 422.2440 Calc 422.2438 | Ex 1 |
| 97 | cyclohexyl-OH | pyrrolidin-1-ylmethyl | H, H | 5200 | 8-(2-hydroxy-cyclohexyl)-5-(pyrrolidin-1-ylmethyl)-8,9-dihydro-7H-pyrrolo[3,4-h]quinolin-7-one | $C_{22}H_{28}N_3O_2$ Obs 366.2180 Calc 366.2176 | Ex 1 |

TABLE 2-continued

| Compd # | R¹ | R² | R³, R⁴ | M1 Pot. | Compound Name | HRMS/ LRMS | Method |
|---|---|---|---|---|---|---|---|
| 98 | cyclohexyl-OH | pyrrolidinyl-CH₂ (3,3-F₂) | H, H | 151 | 5-[(3,3-difluoro-pyrrolidin-1-yl)methyl]-8-(2-hydroxy-cyclohexyl)-8,9-dihydro-7H-pyrrolo[3,4-h]quinolin-7-one | $C_{22}H_{26}F_2N_3O_2$ Obs 402.1993 Calc 402.1988 | Ex 1 |
| 99 | cyclohexyl-OH | morpholinyl-CH₂ | H, H | 150 | 8-(2-hydroxy-cyclohexyl)-5-(morpholin-4-ylmethyl)-8,9-dihydro-7H-pyrrolo[3,4-h]quinolin-7-one | $C_{22}H_{28}N_3O_3$ Obs 382.2128 Calc 382.2125 | Ex 1 |
| 100 | cyclohexyl-OH | 4,4-dimethyl-piperidinyl-CH₂ | H, H | 430 | 5-[(4,4-dimethyl-piperidin-1-yl)methyl]-8-(2-hydroxy-cyclohexyl)-8,9-dihydro-7H-pyrrolo[3,4-h]quinolin-7-one | $C_{25}H_{34}N_3O_2$ Obs 408.2650 Calc 408.2646 | Ex 1 |
| 101 | cyclohexyl-OH | 4-hydroxy-4-methyl-piperidinyl-CH₂ | H, H | 930 | 8-(2-hydroxy-cyclohexyl)-5-[(4-hydroxy-4-methyl-piperidin-1-yl)methyl]-8,9-dihydro-7H-pyrrolo[3,4-h]quinolin-7-one | $C_{24}H_{32}N_3O_3$ Obs 410.2443 Calc 410.2438 | Ex 1 |

TABLE 2-continued

| Compd # | R¹ | R² | R³, R⁴ | M1 Pot. | Compound Name | HRMS/ LRMS | Method |
|---|---|---|---|---|---|---|---|
| 102 | cyclohexyl-OH | piperidinyl-Me, F | H, H | 250 | 5-[(4-fluoro-4-methyl-piperidin-1-yl)methyl]-8-[(1S,2S)-2-hydroxy-cyclohexyl]-8,9-dihydro-7H-pyrrolo[3,4-h]quinolin-7-one | $C_{24}H_{31}FN_3O_2$ Obs 412.2389 Calc 412.2395 | Ex 9 |
| 103 | cyclohexyl-OH | piperidinyl-F, ethynyl | H, H | 11 | 5-[(4-ethynyl-4-fluoro-piperidin-1-yl)methyl]-8-[(1S,2S)-2-hydroxy-cyclohexyl]-8,9-dihydro-7H-pyrrolo[3,4-h]quinolin-7-one | $C_{25}H_{29}FN_3O_2$ Obs 422.2231 Calc 411.2238 | Ex 9 |
| 104 | cyclohexyl-OH | 4,4-difluoropiperidinyl | H, Me | 15 | 5-[(4,4-difluoro-piperidin-1-yl)methyl]-8-[(1R,2S)-2-hydroxy-cyclohexyl]-9-methyl-8,9-dihydro-7H-pyrrolo[3,4-h]quinolin-7-one | $C_{24}H_{30}F_2N_3O_2$ Obs 430.2308 Calc 430.2301 | Ex 3 |

TABLE 2-continued

| Compd # | R¹ | R² | R³, R⁴ | M1 Pot. | Compound Name | HRMS/ LRMS | Method |
|---|---|---|---|---|---|---|---|
| 105 | cyclohexyl-OH | piperidine-4,4-F₂ (CH₂ linker) | H, Et | 9.9 | 5-[(4,4-difluoro-piperidin-1-yl)methyl]-9-ethyl-8-[(1R,2S)-2-hydroxy-cyclo-hexyl]-8,9-dihydro-7H-pyrrolo[3,4-h]quinolin-7-one | $C_{25}H_{32}F_2N_3O_2$ Obs 444.2468 Calc 444.2457 | Ex 3 |
| 106 | tetrahydropyran-3-yl-OH | piperidine-4,4-F₂ (CH₂ linker) | H, Me | 110 | 1,5-anhydro-2,4-dideoxy-4-{5-[(4,4-difluoro-piperidin-1-yl)methyl]-9-methyl-7-oxo-7,9-dihydro-8H-pyrrolo[3,4-h]quinolin-8-yl}-D-erythro-pentitol | $C_{23}H_{28}F_2N_3O_3$ Obs 432.2103 Calc 432.2093 | Exs 3 and 8 |
| 107 | tetrahydropyran-4-yl-OH | piperidine-4,4-F₂ (CH₂ linker) | H, Me | 12 | 1,5-anhydro-3,4-dideoxy-3-{5-[(4,4-difluoro-piperidin-1-yl)methyl]-9-methyl-7-oxo-7,9-dihydro-8H-pyrrolo[3,4-h]quinolin-8-yl}-D-erythro-pentitol | $C_{23}H_{28}F_2N_3O_3$ Obs 432.2098 Calc 432.2093 | Exs 3 and 7 |

TABLE 2-continued

| Compd # | R¹ | R² | R³, R⁴ | M1 Pot. | Compound Name | HRMS/ LRMS | Method |
|---|---|---|---|---|---|---|---|
| 108 | tetrahydropyran-4-yl with 3-OH | 1-[(4-cyano-4-(pyridin-2-yl)piperidin-1-yl)methyl] | H, Me | | 1,5-anhydro-3-{5-[(4-cyano-4-pyridin-2-ylpiperidin-1-yl)methyl]-9-methyl-7-oxo-7,9-dihydro-8H-pyrrolo[3,4-h]quinolin-8-yl}-2,3-dideoxy-pentitol | $C_{29}H_{31}N_5O_3$ [M + H] calc. 498.25 obs. 498.2519 | Exs 3 and 7 |
| 109 | tetrahydropyran-4-yl with 3-OH | 1-[(4-cyano-4-(4-methylpyridin-2-yl)piperidin-1-yl)methyl] | H, Me | | 1,5-anhydro-3-(5-{[4-cyano-4-(4-methyl-pyridin-2-yl)piperidin-1-yl]methyl}-9-methyl-7-oxo-7,9-dihydro-8H-pyrrolo[3,4-h]quinolin-8-yl)-2,3-dideoxy-pentitol | $C_{30}H_{33}N_5O_3$ [M + H] calc. 512.2656 obs. 512.2669 | Exs 3 and 7 |
| 110 | tetrahydropyran-4-yl with 3-OH | 1-[(4-cyano-4-fluoropiperidin-1-yl)methyl] | H, Me | | 1,5-anhydro-3-{5-[(4-cyano-4-fluoro-piperidin-1-yl)methyl]-9-methyl-7-oxo-7,9-dihydro-8H-pyrrolo[3,4-h]quinolin-8-yl}-2,3-dideoxy-pentitol | $C_{24}H_{27}FN_4O_3$ [M + H] calc. 439.214 obs. 439.2148 | Exs 3 and 7 |

TABLE 2-continued

| Compd # | R¹ | R² | R³, R⁴ | M1 Pot. | Compound Name | HRMS/ LRMS | Method |
|---|---|---|---|---|---|---|---|
| 111 | tetrahydropyran-OH | 4-fluoropiperidin-1-ylmethyl | H, Me | | 1,5-anhydro-3-{5-[(4-fluoro-piperidin-1-yl)methyl]-9-methyl-7-oxo-7,9-dihydro-8H-pyrrolo[3,4-h]quinolin-8-yl}-2,3-dideoxy-pentitol | $C_{23}H_{28}FN_3O_3$ [M + H] calc. 414.2187 obs. 414.2195 | Exs 3 and 7 |
| 112 | tetrahydropyran-OH | 4-cyanopiperidin-1-ylmethyl | H, Me | | 1,5-anhydro-3-{5-[(4-cyano-piperidin-1-yl)methyl]-9-methyl-7-oxo-7,9-dihydro-8H-pyrrolo[3,4-h]quinolin-8-yl}-2,3-dideoxy-pentitol | $C_{24}H_{28}N_4O_3$ [M + H] calc. 421.2234 obs. 421.224 | Exs 3 and 7 |
| 113 | tetrahydropyran-OH | 4-ethynylpiperidin-1-ylmethyl | H, Me | | 1,5-anhydro-2,3-dideoxy-3-{5-[(4-ethynyl-piperidin-1-yl)methyl]-9-methyl-7-oxo-7,9-dihydro-8H-pyrrolo[3,4-h]quinolin-8-yl}pentitol | $C_{25}H_{29}N_3O_3$ [M + H] calc. 420.2282 obs. 420.2288 | Exs 3 and 7 |

TABLE 2-continued

| Compd # | R¹ | R² | R³, R⁴ | M1 Pot. | Compound Name | HRMS/ LRMS | Method |
|---|---|---|---|---|---|---|---|
| 114 | (tetrahydropyran-4-yl with OH) | (4-ethynyl-4-fluoropiperidin-1-yl)methyl | H, Me | | 1,5-anhydro-2,3-dideoxy-3-{5-[(4-ethynyl-4-fluoro-piperidin-1-yl)methyl]-9-methyl-7-oxo-7,9-dihydro-8H-pyrrolo[3,4-h]quinolin-8-yl}pentitol | $C_{25}H_{28}FN_3O_3$ [M + H] calc. 438.2187 obs. 438.2197 | Exs 3 and 7 |
| 115 | (tetrahydropyran-4-yl with OH) | (4-fluoro-4-prop-1-yn-1-ylpiperidin-1-yl)methyl | H, Me | | 1,5-anhydro-2,3-dideoxy-3-{5-[(4-fluoro-4-prop-1-yn-1-ylpiperidin-1-yl)methyl]-9-methyl-7-oxo-7,9-dihydro-8H-pyrrolo[3,4-h]quinolin-8-yl}pentitol | $C_{26}H_{30}FN_3O_3$ [M + H] calc. 452.2344 obs. 452.2354 | Exs 3 and 7 |
| 116 | (2-hydroxycyclohexyl) | (4,4-difluoropiperidin-1-yl)methyl | H, H | 21 | 5-[(4,4-difluoro-piperidin-1-yl)methyl]-8-(2-hydroxy-cyclo-hexyl)-8,9-dihydro-7H-pyrrolo[3,4-h]quinolin-7-one | $C_{23}H_{28}F_2N_3O_2$ Obs 416.2141 Calc 416.2144 | Ex 1 |

TABLE 2-continued

| Compd # | R¹ | R² | R³, R⁴ | M1 Pot. | Compound Name | HRMS/ LRMS | Method |
|---|---|---|---|---|---|---|---|
| 117 | cyclohexyl-OH | piperidine-CN, F | H, H | 38 | 4-fluoro-1-({8-[(1S,2S)-2-hydroxy-cyclo-hexyl]-7-oxo-8,9-dihydro-7H-pyrrolo[3,4-h]quinolin-5-yl}methyl)piperidine-4-carbonitrile | $C_{24}H_{28}FN_4O_2$ Obs 423.2191 Calc 423.2191 | Ex 9 |
| 118 | cyclohexyl-OH | piperidine-CN, F | H, Me | 450 | 4-fluoro-1-{[8-(2-hydroxy-cyclo-hexyl)-9-methyl-7-oxo-8,9-dihydro-7H-pyrrolo[3,4-h]quinolin-5-yl]methyl}piperidine-4-carbonitrile | $C_{25}H_{30}FN_4O_2$ Obs 437.2384 Calc 437.2347 | Exs 3 and 9 |
| 119 | cyclohexyl-OH | piperidine-CN, F | H, Me | 44 | 4-fluoro-1-{[8-(2-hydroxy-cyclo-hexyl)-9-methyl-7-oxo-8,9-dihydro-7H-pyrrolo[3,4-h]quinolin-5-yl]methyl}piperidine-4-carbonitrile | $C_{25}H_{30}FN_4O_2$ Obs 437.2341 Calc 437.2347 | Exs 3 and 9 |

TABLE 2-continued

| Compd # | R¹ | R² | R³, R⁴ | M1 Pot. | Compound Name | HRMS/LRMS | Method |
|---|---|---|---|---|---|---|---|
| 120 | cyclohexyl-OH | piperidine with CN and F | H, Et | 21 | 1-({9-ethyl-8-[(1R,2S)-2-hydroxycyclohexyl]-7-oxo-8,9-dihydro-7H-pyrrolo[3,4-h]quinolin-5-yl}methyl)-4-fluoropiperidine-4-carbonitrile | $C_{26}H_{32}FN_4O_2$ Obs 451.2505 Calc 451.2504 | Exs 3 and 9 |
| 121 | cyclohexyl-OH | 3-fluoropiperidine | H, H | 108 | 5-[(3-fluoropiperidin-1-yl)methyl]-8-(2-hydroxycyclohexyl)-8,9-dihydro-7H-pyrrolo[3,4-h]quinolin-7-one | $C_{23}H_{29}FN_3O_2$ Obs 398.2245 Calc 398.2238 | Ex 1 |
| 122 | cyclohexyl-OH | 3,3-difluoropiperidine | H, H | 86 | 5-[(3,3-difluoropiperidin-1-yl)methyl]-8-(2-hydroxycyclohexyl)-8,9-dihydro-7H-pyrrolo[3,4-h]quinolin-7-one | $C_{23}H_{28}F_2N_3O_2$ Obs 416.2148 Calc 416.2144 | Ex 1 |

TABLE 2-continued

| Compd # | R¹ | R² | R³, R⁴ | M1 Pot. | Compound Name | HRMS/ LRMS | Method |
|---|---|---|---|---|---|---|---|
| 123 | cyclohexyl-OH | piperidinyl-CF₃ methyl | H, H | 97 | 8-(2-hydroxy-cyclo-hexyl)-5-{[4-(trifluoro-methyl)piperidin-1-yl]methyl}-8,9-dihydro-7H-pyrrolo[3,4-h]quinolin-7-one | $C_{24}H_{29}F_3N_3O_2$ Obs 448.2211 Calc 448.2206 | Ex 1 |
| 124 | cyclohexyl-OH | piperidinyl-ethynyl methyl | H, H | 44 | 5-[(4-ethynyl-piperidin-1-yl)methyl]-8-(2-hydroxy-cyclo-hexyl)-8,9-dihydro-7H-pyrrolo[3,4-h]quinolin-7-one | $C_{25}H_{30}N_3O_2$ Obs 404.2337 Calc 404.2333 | Ex 1 |
| 125 | cyclohexyl-OH | 4-fluoro-4-(pent-1-ynyl)piperidinyl methyl | H, H | 130 | 5-[(4-fluoro-4-pent-1-yn-1-ylpiperidin-1-yl)methyl]-8-[(1S,2S)-2-hydroxy-cyclo-hexyl]-8,9-dihydro-7H-pyrrolo[3,4-h]quinolin-7-one | $C_{28}H_{35}FN_3O_2$ Obs 464.2710 Calc 464.2708 | Ex 10 |
| 126 | 3-hydroxyphenyl | 4,4-difluoropiperidinyl methyl | H, H | 1382 | 2-(2-fluoro-phenyl)-5-{[4-(pyridin-2-yl)piperazin-1-yl]methyl}-1,2-dihydro-3H-benzo[e]isoindol-3-one | LRMS: 451.3 MW: 409.44 | Ex 1 |

TABLE 2-continued

| Compd # | R¹ | R² | R³, R⁴ | M1 Pot. | Compound Name | HRMS/ LRMS | Method |
|---|---|---|---|---|---|---|---|
| 127 | 3-hydroxyphenyl | (4-fluoro-4-cyanopiperidin-1-yl)methyl | H, H | 44 | 4-fluoro-1-{[8-(3-hydroxy-phenyl)-7-oxo-8,9-dihydro-7H-pyrrolo[3,4-h]quinolin-5-yl]methyl}piperidine-4-carbonitrile | $C_{24}H_{22}FN_4O_2$ Obs 417.1718 Calc 417.1721 | Ex 9 |
| 128 | 3-hydroxyphenyl | (4-ethynyl-4-fluoropiperidin-1-yl)methyl | H, H | 843 | 5-[(4-ethynyl-4-fluoro-piperidin-1-yl)methyl]-8-(3-hydroxy-phenyl)-8,9-dihydro-7H-pyrrolo[3,4-h]quinolin-7-one | $C_{25}H_{23}FN_3O_2$ Obs 416.1768 Calc 416.1769 | Ex 9 |
| 129 | 3-(dimethylcarbamoyloxy)phenyl | (4-fluoro-4-cyanopiperidin-1-yl)methyl | H, H | 2167 | 3-{5-[(4-cyano-4-fluoro-piperidin-1-yl)methyl]-7-oxo-7,9-dihydro-8H-pyrrolo[3,4-h]quinolin-8-yl}phenyl dimethyl carbamate | $C_{27}H_{27}FN_5O_3$ Obs 488.2099 Calc 488.2092 | Ex 10 |

TABLE 2-continued

| Compd # | R¹ | R² | R³, R⁴ | M1 Pot. | Compound Name | HRMS/ LRMS | Method |
|---|---|---|---|---|---|---|---|
| 130 | 3-(dimethylcarbamoyloxy)phenyl | (4-ethynyl-4-fluoropiperidin-1-yl)methyl | H, H | 1428 | 3-{5-[(4-ethynyl-4-fluoro-piperidin-1-yl)methyl]-7-oxo-7,9-dihydro-8H-pyrrolo[3,4-h]quinolin-8-yl}phenyl dimethylcarbamate | $C_{28}H_{28}FN_4O_3$ Obs 487.2139 Calc 487.2140 | Exs 9 and 10 |
| 131 | (1S,2S)-2-hydroxycyclohexyl | (4-fluoro-4-(prop-1-yn-1-yl)piperidin-1-yl)methyl | H, H | 33 | 5-[(4-fluoro-4-prop-1-yn-1-ylpiperidin-1-yl)methyl]-8-[(1S,2S)-2-hydroxy-cyclohexyl]-8,9-dihydro-7H-pyrrolo[3,4-h]quinolin-7-one | $C_{26}H_{31}FN_3O_2$ Obs 436.2397 Calc 436.22395 | Ex 9 |
| 132 | (1S,2S)-2-hydroxycyclohexyl | (4-(cyclopropylethynyl)-4-fluoropiperidin-1-yl)methyl | H, H | 246 | 5-{[4-(cyclopropyl-ethynyl)-4-fluoro-piperidin-1-yl]methyl}-8-[(1S,2S)-2-hydroxy-cyclohexyl]-8,9-dihydro-7H-pyrrolo[3,4-h]quinolin-7-one | $C_{28}H_{33}FN_3O_2$ Obs 462.2549 Calc 462.2551 | Ex 9 |

TABLE 2-continued

| Compd # | R¹ | R² | R³, R⁴ | M1 Pot. | Compound Name | HRMS/ LRMS | Method |
|---|---|---|---|---|---|---|---|
| 133 | cyclohexyl-OH | piperidin-4-yl (4-F, 4-ethynyl-p-tolyl)-CH₂- | H, H | 129 | 5-({4-fluoro-4-[(4-fluorophenyl)ethynyl]piperidin-1-yl}methyl)-8-(2-hydroxy-cyclohexyl)-8,9-dihydro-7H-pyrrolo[3,4-h]quinolin-7-one | $C_{31}H_{32}F_2N_3O_2$ Obs 516.2470 Calc 516.2457 | Ex 9 |
| 134 | cyclohexyl-OH | piperidin-4-yl (4-F, 4-benzyl)-CH₂- | H, H | 207 | 5-[(4-benzyl-4-fluoro-piperidin-1-yl)methyl]-8-(2-hydroxy-cyclohexyl)-8,9-dihydro-7H-pyrrolo[3,4-h]quinolin-7-one | $C_{30}H_{35}FN_3O_2$ Obs 488.2714 Calc 488.2708 | Ex 1 |
| 135 | cyclohexyl-OH | piperidin-4-yl (4-CN, 4-(pyridin-4-ylmethyl))-CH₂- | H, H | 156 | 1-{[8-(2-hydroxy-cyclohexyl)-7-oxo-8,9-dihydro-7H-pyrrolo[3,4-h]quinolin-5-yl]methyl}-4-(pyridin-4-ylmethyl)piperidine-4-carbonitrile | $C_{30}H_{34}N_5O_2$ Obs 496.2710 Calc 496.2707 | Ex 1 |
| 136 | (1S,2S)-2-hydroxy-cyclohexyl | piperidin-4-yl (4-CN, 4-phenyl)-CH₂- | H, H | 14 | 1-({8-[(1S,2S)-2-hydroxy-cyclohexyl]-7-oxo-8,9-dihydro-7H-pyrrolo[3,4-h]quinolin-5-yl}methyl)-4-phenyl-piperidine-4-carbonitrile | $C_{30}H_{33}N_4O_2$ Obs 481.2587 Calc 481.2598 | Ex 1 |

TABLE 2-continued

| Compd # | R¹ | R² | R³, R⁴ | M1 Pot. | Compound Name | HRMS/ LRMS | Method |
|---|---|---|---|---|---|---|---|
| 137 | cyclohexyl-OH | piperidine with CN and phenyl | H, Me | 480 | 1-{[8-(2-hydroxy-cyclohexyl)-9-methyl-7-oxo-8,9-dihydro-7H-pyrrolo[3,4-h]quinolin-5-yl]methyl}-4-phenyl-piperidine-4-carbonitrile | $C_{31}H_{35}N_4O_2$ Obs 495.2744 Calc 495.2755 | Ex 3 |
| 138 | cyclohexyl-OH | piperidine with CN and phenyl | H, Me | 69 | 1-{[8-(2-hydroxy-cyclohexyl)-9-methyl-7-oxo-8,9-dihydro-7H-pyrrolo[3,4-h]quinolin-5-yl]methyl}-4-phenyl-piperidine-4-carbonitrile | $C_{31}H_{36}N_4O_2$ Obs 495.2766 Calc 495.2755 | Ex 1 |
| 139 | cyclohexyl-OH | 4-phenyl-piperidine | H, H | 85 | 8-(2-hydroxy-cyclohexyl)-5-[(4-phenyl-piperidin-1-yl)methyl]-8,9-dihydro-7H-pyrrolo[3,4-h]quinolin-7-one | $C_{29}H_{34}N_3O_2$ Obs 456.2641 Calc 456.2646 | Ex 1 |
| 140 | cyclohexyl-OH | 4-phenyl-piperidine | H, Me | 3200 | 8-(2-hydroxy-cyclohexyl)-9-methyl-5-[(4-phenyl-piperidin-1-yl)methyl]-8,9-dihydro-7H-pyrrolo[3,4-h]quinolin-7-one | $C_{30}H_{36}N_3O_2$ Obs 470.2810 Calc 470.2802 | Ex 3 |

TABLE 2-continued

| Compd # | R¹ | R² | R³, R⁴ | M1 Pot. | Compound Name | HRMS/ LRMS | Method |
|---|---|---|---|---|---|---|---|
| 141 | cyclohexyl-OH | 4-phenylpiperidin-1-ylmethyl | H, Me | 490 | 8-(2-hydroxy-cyclohexyl)-9-methyl-5-[(4-phenyl-piperidin-1-yl)methyl]-8,9-dihydro-7H-pyrrolo[3,4-h]quinolin-7-one | $C_{30}H_{36}N_3O_2$ Obs 470.2807 Calc 470.2802 | Ex 3 |
| 142 | cyclohexyl-OH | 4-(pyridin-4-yl)piperidin-1-ylmethyl | H, H | 51 | 8-(2-hydroxy-cyclohexyl)-5-[(4-pyridin-4-ylpiperidin-1-yl)methyl]-8,9-dihydro-7H-pyrrolo[3,4-h]quinolin-7-one | $C_{28}H_{34}N_4O_2$ Obs 457.2597 Calc 457.2598 | Ex 1 |
| 143 | cyclohexyl-OH | 4-(pyridin-4-yl)piperidin-1-ylmethyl | H, Me | 89 | 8-(2-hydroxy-cyclohexyl)-9-methyl-5-[(4-pyridin-4-ylpiperidin-1-yl)methyl]-8,9-dihydro-7H-pyrrolo[3,4-h]quinolin-7-one | $C_{29}H_{35}N_4O_2$ Obs 471.2757 Calc 471.2755 | Ex 3 |
| 144 | cyclohexyl-OH | 4-hydroxy-4-(pyridin-4-yl)piperidin-1-ylmethyl | H, H | 510 | 8-(2-hydroxy-cyclohexyl)-5-[(4-hydroxy-4-pyridin-4-ylpiperidin-1-yl)methyl]-8,9-dihydro-7H-pyrrolo[3,4-h]quinolin-7-one | $C_{28}H_{33}N_4O_3$ Obs 473.2549 Calc 473.2547 | Ex 1 |

TABLE 2-continued

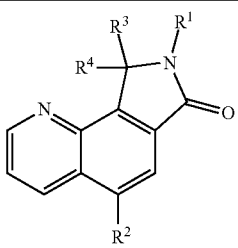

| Compd # | R¹ | R² | R³, R⁴ | M1 Pot. | Compound Name | HRMS/ LRMS | Method |
|---|---|---|---|---|---|---|---|
| 145 | cyclohexyl-OH | piperidine-CN-pyridine | H, H | 7.6 | 1-({8-[(1S,2S)-2-hydroxy-cyclo-hexyl]-7-oxo-8,9-dihydro-7H-pyrrolo[3,4-h]quinolin-5-yl}methyl)-4-pyridin-2-ylpiperidine-4-carbonitrile | $C_{29}H_{32}N_5O_2$ Obs 482.2555 Calc 482.2551 | Ex 1 |
| 146 | cyclohexyl-OH | piperidine-F-pyridine | H, H | 11 | 5-[(4-fluoro-4-pyridin-2-ylpiperidin-1-yl)methyl]-8-(2-hydroxy-cyclo-hexyl)-8,9-dihydro-7H-pyrrolo[3,4-h]quinolin-7-one | $C_{28}H_{33}FN_4O_2$ Obs 475.2497 Calc 475.2504 | Ex 2 |
| 147 | cyclohexyl-OH | piperidine-F-pyridine | H, Me | 70 | 5-[(4-fluoro-4-pyridin-2-ylpiperidin-1-yl)methyl]-8-[(1R,2S)-2-hydroxy-cyclo-hexyl]-9-methyl-8,9-dihydro-7H-pyrrolo[3,4-h]quinolin-7-one | $C_{29}H_{34}FN_4O_2$ Obs 489.2661 Calc 489.3 | Exs 2 and 3 |
| 148 | cyclohexyl-OH | piperidine-CN-(4-Me-pyridine) | H, H | 4.7 | 1-{[8-(2-hydroxy-cyclo-hexyl)-7-oxo-8,9-dihydro-7H-pyrrolo[3,4-h]quinolin-5-yl]methyl}-4-(4-methyl-pyridin-2-yl)piperidine-4-carbonitrile | $C_{30}H_{35}N_5O_2$ Obs 496.2705 Calc 496.2707 | Ex 1 |

TABLE 2-continued

| Compd # | R¹ | R² | R³, R⁴ | M1 Pot. | Compound Name | HRMS/ LRMS | Method |
|---|---|---|---|---|---|---|---|
| 149 | cyclohexyl-OH | piperidine-CN-pyridin-2-yl | H, Me | 6.0 | 1-({(9R)-8-[(1S,2S)-2-hydroxy-cyclo-hexyl]-9-methyl-7-oxo-8,9-dihydro-7H-pyrrolo[3,4-h]quinolin-5-yl}methyl)-4-pyridin-2-ylpiperidine-4-carbonitrile | $C_{30}H_{34}N_5O_2$ Obs 496.2695 Calc 496.2707 | Ex 3 |
| 150 | cyclohexyl-OH | piperidine-CN-pyridin-2-yl | H, Me | 54 | 1-({(9R)-8-[(1S,2S)-2-hydroxy-cyclo-hexyl]-9-methyl-7-oxo-8,9-dihydro-7H-pyrrolo[3,4-h]quinolin-5-yl}methyl)-4-pyridin-2-ylpiperidine-4-carbonitrile | $C_{30}H_{34}N_5O_2$ Obs 496.2724 Calc 469.2707 | Ex 3 |
| 151 | cyclohexyl-OH | piperidine-CN-(4-Me-pyridin-2-yl) | H, Me | 3.5 | 1-({(9R)-8-[(1S,2S)-2-hydroxy-cyclo-hexyl]-9-methyl-7-oxo-8,9-dihydro-7H-pyrrolo[3,4-h]quinolin-5-yl}methyl)-4-(4-methyl-pyridin-2-yl)piperidine-4-carbonitrile | $C_{31}H_{35}N_5O_2$ Obs 510.2882 Calc 510.2864 | Ex 3 |

TABLE 2-continued

| Compd # | R[1] | R[2] | R[3], R[4] | M1 Pot. | Compound Name | HRMS/ LRMS | Method |
|---|---|---|---|---|---|---|---|
| 152 | cyclohexyl-OH | piperidine-CN-(4-methylpyridin-2-yl) | H, Me | 14 | 1-({(9R)-8-[(1S,2S)-2-hydroxy-cyclo-hexyl]-9-methyl-7-oxo-8,9-dihydro-7H-pyrrolo[3,4-h]quinolin-5-yl}methyl)-4-(4-methyl-pyridin-2-yl)piperidine-4-carbonitrile | $C_{31}H_{35}N_5O_2$ Obs 510.2882 Calc 510.2864 $C_{31}H_{35}N_5O_2$ | Ex 3 |
| 153 | cyclohexyl-OH | piperidine-F-(pyridin-2-yl) | H, Me | 8.0 | (9R)-5-[(4-fluoro-4-pyridin-2-ylpiperidin-1-yl)methyl]-8-[(1S,2S)-2-hydroxy-cyclo-hexyl]-9-methyl-8,9-dihydro-7H-pyrrolo[3,4-h]quinolin-7-one | $C_{29}H_{34}FN_4O_2$ Obs 489.2646 Calc 489.2660 | Exs 2 and 3 |
| 154 | cyclohexyl-OH | piperidine-CN-(6-methoxypyridin-2-yl) | H, H | 19 | 1-({8-[(1S,2S)-2-hydroxy-cyclo-hexyl]-7-oxo-8,9-dihydro-7H-pyrrolo[3,4-h]quinolin-5-yl}methyl)-4-(6-methoxy-pyridin-2-yl)piperidine-4-carbonitrile | $C_{30}H_{34}N_5O_3$ Obs 512.2642 Calc 512.2656 | Ex 6 |

TABLE 2-continued

| Compd # | R¹ | R² | R³, R⁴ | M1 Pot. | Compound Name | HRMS/ LRMS | Method |
|---|---|---|---|---|---|---|---|
| 155 | cyclohexyl-OH | piperidine-CN-pyridine-OMe | H, Me | 520 | 1-({8-[(1S,2S)-2-hydroxy-cyclohexyl]-7-oxo-8,9-dihydro-7H-pyrrolo[3,4-h]quinolin-5-yl}methyl)-4-(6-methoxy-pyridin-2-yl)piperidine-4-carbonitrile | $C_{31}H_{36}N_5O_3$ Obs 526.2813 Calc 526.2813 | Exs 3 and 6 |
| 156 | cyclohexyl-OH | piperidine-CN-pyridine-OMe | H, Me | 57 | 1-({8-[(1S,2S)-2-hydroxy-cyclohexyl]-7-oxo-8,9-dihydro-7H-pyrrolo[3,4-h]quinolin-5-yl}methyl)-4-(6-methoxy-pyridin-2-yl)piperidine-4-carbonitrile | $C_{31}H_{37}N_5O_3$ Obs 526.2817 Calc 526.2813 | Exs 3 and 6 |
| 157 | cyclohexyl-OH | piperazine-pyrazole-Me | H, H | 42 | 8-[(1S,2S)-2-hydroxy-cyclohexyl]-5-{[4-(1-methyl-1H-pyrazol-4-yl)piperazin-1-yl]methyl}-8,9-dihydro-7H-pyrrolo[3,4-h]quinolin-7-one | $C_{26}H_{33}N_6O_2$ Obs 461.2649 Calc 461.2660 | Ex 1 |

TABLE 2-continued

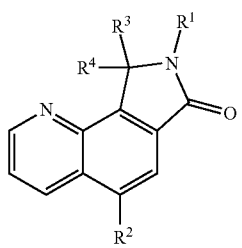

| Compd # | R$^1$ | R$^2$ | R$^3$, R$^4$ | M1 Pot. | Compound Name | HRMS/ LRMS | Method |
|---|---|---|---|---|---|---|---|
| 158 | cyclohexyl-OH | piperazine-N-(1-methyl-1H-pyrazol-4-yl) | H, Me | 70 | 8-(2-hydroxy-cyclohexyl)-9-methyl-5-{[4-(1-methyl-1H-pyrazol-4-yl)piperazin-1-yl]methyl}-8,9-dihydro-7H-pyrrolo[3,4-h]quinolin-7-one | $C_{27}H_{35}N_6O_2$ Obs 475.2818 Calc 475.2816 | Ex 3 |
| 160 | cyclohexyl-OH | piperazine-N-(pyridin-4-yl) | H, H | 110 | 8-(2-hydroxy-cyclohexyl)-5-[(4-pyridin-4-ylpiperazin-1-yl)methyl]-8,9-dihydro-7H-pyrrolo[3,4-h]quinolin-7-one | $C_{27}H_{33}N_5O_2$ Obs 458.2543 Calc 458.2551 | Ex 1 |
| 161 | cyclohexyl-OH | piperazine-N-(pyridin-4-yl)piperidine | H, Me | 650 | 8-(2-hydroxy-cyclohexyl)-9-methyl-5-[(4-pyridin-4-ylpiperidin-1-yl)methyl]-8,9-dihydro-7H-pyrrolo[3,4-h]quinolin-7-one | $C_{29}H_{35}N_4O_2$ Obs 471.2753 Calc 471.2755 | Ex 3 |
| 162 | cyclohexyl-OH | piperazine-N-(pyridin-3-yl) | H, H | 28 | 8-(2-hydroxy-cyclohexyl)-5-[(4-pyridin-3-ylpiperazin-1-yl)methyl]-8,9-dihydro-7H-pyrrolo[3,4-h]quinolin-7-one | $C_{27}H_{33}N_5O_2$ Obs 458.2544 Calc 458.2551 | Ex 1 |

TABLE 2-continued

| Compd # | R¹ | R² | R³, R⁴ | M1 Pot. | Compound Name | HRMS/ LRMS | Method |
|---|---|---|---|---|---|---|---|
| 163 | cyclohexyl-OH | piperazinyl-CH₂- with N-(pyridin-3-yl) | H, Me | 520 | 8-(2-hydroxy-cyclohexyl)-9-methyl-5-[(4-pyridin-3-yl-piperazin-1-yl)methyl]-8,9-dihydro-7H-pyrrolo[3,4-h]quinolin-7-one | $C_{28}H_{34}N_5O_2$ Obs 472.2705 Calc 472.2707 | Ex 3 |
| 164 | cyclohexyl-OH | piperazinyl-CH₂- with N-(pyridin-3-yl) | H, Me | 36 | 8-(2-hydroxy-cyclohexyl)-9-methyl-5-[(4-pyridin-3-yl-piperazin-1-yl)methyl]-8,9-dihydro-7H-pyrrolo[3,4-h]quinolin-7-one | $C_{28}H_{34}N_5O_2$ Obs 472.2709 Calc 472.2707 | Ex 3 |
| 165 | cyclohexyl-OH | piperazinyl-CH₂- with N-(pyridin-2-yl) | H, H | 15 | 8-(2-hydroxy-cyclohexyl)-5-[(4-pyridin-2-ylpiperazin-1-yl)methyl]-8,9-dihydro-7H-pyrrolo[3,4-h]quinolin-7-one | $C_{27}H_{33}N_5O_2$ Obs 458.2546 Calc 458.2551 | Ex 1 |
| 166 | cyclohexyl-OH | piperazinyl-CH₂- with N-(pyridin-2-yl) | H, Me | 580 | 8-(2-hydroxy-cyclohexyl)-9-methyl-5-[(4-pyridin-2-yl-piperazin-1-yl)methyl]-8,9-dihydro-7H-pyrrolo[3,4-h]quinolin-7-one | $C_{28}H_{34}N_5O_2$ Obs 472.2708 Calc 472.2707 | Ex 3 |

TABLE 2-continued

| Compd # | R¹ | R² | R³, R⁴ | M1 Pot. | Compound Name | HRMS/ LRMS | Method |
|---|---|---|---|---|---|---|---|
| 167 | cyclohexyl-OH | piperazine-CH₂- linked to pyridin-2-yl | H, Me | 59 | 8-(2-hydroxy-cyclohexyl)-9-methyl-5-[(4-pyridin-2-yl-piperazin-1-yl)methyl]-8,9-dihydro-7H-pyrrolo[3,4-h]quinolin-7-one | $C_{28}H_{34}N_5O_2$ Obs 472.2711 Calc 472.2707 | Ex 3 |
| 168 | cyclohexyl-OH | piperazine-CH₂- linked to 4-methoxyphenyl | H, H | 24 | 8-(2-hydroxy-cyclohexyl)-5-{[4-(4-methoxyphenyl)piperazin-1-yl]methyl}-8,9-dihydro-7H-pyrrolo[3,4-h]quinolin-7-one | $C_{29}H_{36}N_4O_3$ Obs 487.2696 Calc 487.2704 | Ex 1 |
| 169 | cyclohexyl-OH | piperazine-CH₂- linked to 4-methoxyphenyl | H, Me | 590 | 8-(2-hydroxy-cyclohexyl)-5-{[4-(4-methoxyphenyl)piperazin-1-yl]methyl}-9-methyl-8,9-dihydro-7H-pyrrolo[3,4-h]quinolin-7-one | $C_{30}H_{37}N_4O_3$ Obs 501.2860 Calc 501.2860 | Ex 3 |

TABLE 2-continued

| Compd # | R¹ | R² | R³, R⁴ | M1 Pot. | Compound Name | HRMS/ LRMS | Method |
|---|---|---|---|---|---|---|---|
| 170 | cyclohexyl-OH | piperazinyl-C₆H₄-OMe | H, Me | 100 | 8-(2-hydroxy-cyclohexyl)-5-{[4-(4-methoxyphenyl)piperazin-1-yl]methyl}-9-methyl-8,9-dihydro-7H-pyrrolo[3,4-h]quinolin-7-one | $C_{30}H_{37}N_4O_3$ Obs 501.2865 Calc 501.2860 | Ex 3 |
| 171 | cyclohexyl-OH | piperazinyl-C₆H₄-F | H, H | 23 | 5-{[4-(4-fluorophenyl)piperazin-1-yl]methyl}-8-(2-hydroxy-cyclohexyl)-8,9-dihydro-7H-pyrrolo[3,4-h]quinolin-7-one | $C_{28}H_{33}FN_4O_2$ Obs 475.2493 Calc 475.2504 | Ex 1 |
| 172 | cyclohexyl-OH | piperazinyl-C₆H₄-F | H, Me | 480 | 5-{[4-(4-fluorophenyl)piperazin-1-yl]methyl}-8-(2-hydroxy-cyclohexyl)-9-methyl-8,9-dihydro-7H-pyrrolo[3,4-h]quinolin-7-one | $C_{29}H_{34}FN_4O_2$ Obs 489.2667 Calc 489.2660 | Ex 3 |

TABLE 2-continued

| Compd # | R¹ | R² | R³, R⁴ | M1 Pot. | Compound Name | HRMS/ LRMS | Method |
|---|---|---|---|---|---|---|---|
| 173 | cyclohexyl-OH | piperazinyl-CH₂- linked to 4-fluorophenyl | H, Me | 100 | 5-{[4-(4-fluorophenyl)piperazin-1-yl]methyl}-8-(2-hydroxycyclohexyl)-9-methyl-8,9-dihydro-7H-pyrrolo[3,4-h]quinolin-7-one | $C_{29}H_{34}FN_4O_2$ Obs 489.2665 Calc 489.2660 | Ex 3 |
| 174 | cyclohexyl-OH | piperazinyl-CH₂- linked to phenyl | H, H | 18 | 8-(2-hydroxycyclohexyl)-5-[(4-phenylpiperazin-1-yl)methyl]-8,9-dihydro-7H-pyrrolo[3,4-h]quinolin-7-one | $C_{28}H_{34}N_4O_2$ Obs 457.2599 Calc 457.2598 | Ex 1 |
| 175 | cyclohexyl-OH | piperazinyl-CH₂- linked to phenyl | H, Me | 490 | 8-(2-hydroxycyclohexyl)-9-methyl-5-[(4-phenylpiperazin-1-yl)methyl]-8,9-dihydro-7H-pyrrolo[3,4-h]quinolin-7-one | $C_{29}H_{35}N_4O_2$ Obs 471.2754 Calc 471.2755 | Ex 3 |

TABLE 2-continued

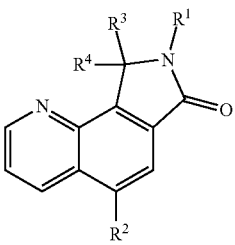

| Compd # | R¹ | R² | R³, R⁴ | M1 Pot. | Compound Name | HRMS/LRMS | Method |
|---|---|---|---|---|---|---|---|
| 176 | (2-hydroxycyclohexyl, with OH) | (CH₂-piperazinyl-phenyl) | H, Me | 93 | 8-(2-hydroxy-cyclo-hexyl)-9-methyl-5-[(4-phenyl-piperazin-1-yl)methyl]-8,9-dihydro-7H-pyrrolo[3,4-h]quinolin-7-one | $C_{29}H_{35}N_4O_2$ Obs 471.2759 Calc 471.2755 | Ex 3 |

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a FLIPR[384] Fluorometric Imaging Plate Reader System. The assay studies the effect of one or several concentrations of test compounds on basal or acetylcholine-stimulated $Ca^{2+}$ levels using FLIPR.

Compounds are prepared and subjected to a preincubation period of 4 mM. Thereafter, a single $EC_{20}$ concentration of acetylcholine is added to each well (3 nM final). The intracellular $Ca^{2+}$ level of each sample is measured and compared to an acetylcholine control to determine any modulatory activity.

Cells: CHOnfat/hM1, hM2, hM3 or hM4 cells are plated 24 hr before the assay at a density of 18,000 cells/well (100 μL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 ug/ml hygromycin is added.

Equipment: 384 well plate, 120 μl, addition plate; 96-well Whatman 2 ml Uniplate Incubator, 37° C., 5% $CO_2$; Skatron EMBLA-384 Plate Washer; Multimek Pipetting System; Genesis Freedom 200 System; Mosquito System; Temo Nanolitre Pipetting System; and FLIPR[384] Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1 N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 μM in buffer for a final concentration of 1 μM in Assay. 20% Pluronic Acid Solution stock, with concentration of 0.04% in Buffer, 0.02% in Assay.

65 μL of 2 mM Fluo-4AM are mixed with 130 μL of 20% Pluronic Acid. The resulting solution and 650 μL FBS is added to the assay buffer for a total volume of 65 mL. Positive Controls: 4-Br-A23187: 10 mM in DMSO; final concentration 10 μM. Acetylcholine: 10 mM in water, working stock at both 20 μM and 30 μM in assay buffer, final concentration of 10 μM. This is used to check the maximum stimulation of the CHOK1/hM1 cells. 20 μM (2×) acetylcholine is added in the preincubation part of the assay, and the 30 μM (3×) stock is added in the second part. ($EC_{20}$)Acetylcholine: 10 mM in water, working stock of 9 nM (3×), and final concentration in assay is 3 nM. This is used after the preincubation with test compounds. Addition of the $EC_{20}$ Acetylcholine to each well with a test compound will ascertain any modulator activity. 24 wells contain 3 nM Acetylcholine alone as a control.

Determining Activity of Putative Compounds:

Screening Plate Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanolitre Pipetting System by transferring 1 μl of serial diluted compounds to each well, and 1 mM acetylcholine (100× stock concentration) were added as a control. Using Temo, 49 μl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 μM acetylcholine control (3×) is added into control wells, and the 3× agonist plate is transferred into a 384 well plate.

Cells are washed three times with 100 μL of buffer, leaving 30 μM of buffer in each well. Using Multimek, 30 μL of Dye Loading Buffer is added into each well and incubated at 37° C., 5% $CO_2$ for up to one hr.

After 60 min, the cells are washed three times with 100 μL of buffer, leaving 30 μL of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

4 min of preincubation with the test compounds is provided to determine any agonist activity on the M1 receptor by comparison to the 1 mM acetylcholine control. After preincubation, the $EC_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 10 μM (10,000 nM) or less. The inflection point is calculated from the FLIPR values, and is a measure of activity. Such a result is indicative of the intrinsic activity of the compounds in use as M1 allosteric modulators.

IP values from the aforementioned assay for representative exemplary compounds of the invention (as described herein) are provided below in Table 3 below:

| Example | IP Value (nM) |
|---------|---------------|
| 1       | 10            |
| 2       | 58            |
| 3       | 19            |
| 4       | 27            |
| 5       | 55            |
| 6       | 65            |
| 7       | 147           |
| 8       | 41            |
| 9       | 420           |
| 10      | 2258          |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

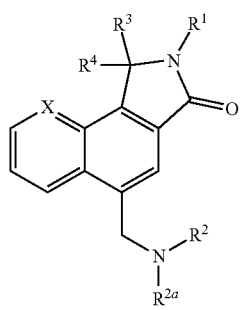

(I)

and pharmaceutically acceptable salts thereof, wherein X=CH $R^1$ represents $C_{3-10}$cycloalkyl that is cyclohexyl, $C_{6-10}$ aryl that is phenyl, and $C_{5-10}$ heterocyclyl that is pyranyl, said cycloalkyl, aryl and heterocyclyl optionally substituted with 1 $R^a$, $R^2$ and $R^{2a}$ together with the nitrogen to which they are attached combined to form a $C_{3-10}$ heterocyclic ring wherein 1 to 2 carbon atoms on the ring are optionally interrupted by 1 to 2 heteroatoms selected from N, O and S, said heterocyclic ring optionally substituted with 1 to 3 groups of $R^a$, $R^3$ and $R^4$ independently represent:
(1) hydrogen,
(2) —$C_{1-6}$ alkyl, optionally substituted with 1 to 3 groups of $R^a$, $R^a$ represents:
(1) hydroxyl,
(2) halogen,
(3) $C_{1-6}$alkyl,
(4) $(CH_2)_nC_{6-10}$ aryl, which is unsubstituted or substituted with 1 to 3 groups of $R^b$,
(5) $(CH_2)_n$heterocyclyl, which is unsubstituted or substituted with 1 to 3 groups of $R^b$, and
(6) —CN,
(7) $(CH_2)_nC_{1-4}$ haloalkyl,
(8) $COOR^3$,
(9) $C_{3-10}$cycloalkyl,
(10) $C(O)C_{1-6}$alkyl,
(11) $S(O)_2C_{1-6}$alkyl,
(12) $C_{2-4}$ alkynyl,
(13) $C_{2-4}$ alkenyl, and
(14) 2 adjacent $R^a$'s on the $C_{3-10}$ heterocyclic ring formed when $R^2$ and $R^{2a}$ combine may combine with the atoms to which they are attached to form a 3-10 carbocyclic ring with 1 to 2 carbons atoms on the ring optionally interrupted by 1 to 2 heteroatoms selected from N, O, and S, wherein said alkyl, aryl, heterocyclyl, cycloalkyl, alkynyl, alkenyl, and carbocyclic ring are optionally substituted with 1 to 3 groups of $R^b$, $R^b$ represents:
(1) hydroxyl,
(2) halogen,
(3) $C_{1-6}$alkyl, and
(4) $C_{1-4}$ haloalkyl,
(5) —$OC_{1-6}$alkyl,
(6) $C_{3-10}$cycloalkyl,
(7) $C_{2-6}$ alkenyl, and
(8) $S(O)_2C_{1-6}$alkyl,
n is 0-2.

2. The compound according to claim 1 of formula (I) wherein $R^1$ is optionally substituted phenyl, pyrrolyl, or cyclohexyl, and pharmaceutically acceptable salts thereof.

3. The compound according to claim 2 of formula (I) wherein $R^1$ is hydroxyphenyl, or hydroxycyclohexyl, and pharmaceutically acceptable salts thereof.

4. The compound according to claim 1 of formula (I) wherein $R^2$ and $R^{2a}$ together with the nitrogen to which they are attached combined to form a $C_{3-10}$ heterocyclic ring wherein 1 to 2 carbon atoms on the ring are optionally interrupted by 1 to 2 heteroatoms selected from N, O and S, said heterocyclic ring optionally substituted with 1 to 3 groups of $R^a$, and pharmaceutically acceptable salts thereof.

5. The compound according to claim 4 of formula (I) wherein $R^2$ and $R^{2a}$ combine to form optionally substituted piperidinyl, piperazinyl, morpholinyl, pyrrolidinyl, or benzpiperidinyl, which are optionally substituted with 1 to 3 groups of $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl, and pharmaceutically acceptable salts thereof.

6. The compound according to claim 1 of formula (I) represented by structural formula Ia:

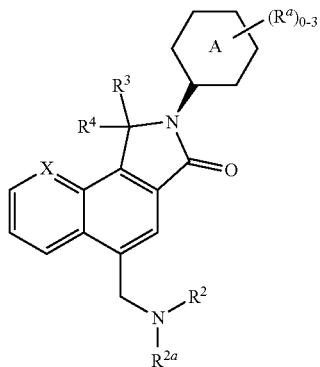

or a pharmaceutically acceptable salt thereof wherein $R^3$ and $R^4$ are both hydrogen, or one $R^3$ and $R^4$ is hydrogen and the other is methyl, A is selected from the group consisting of optionally substituted cyclohexyl, and pyranyl and $R^2$ and $R^{2a}$ combine to form piperidinyl, piperazinyl, morpholinyl, pyrrolidinyl, or benzpiperidinyl, said piperidinyl, piperazinyl, morpholinyl, pyrrolidinyl, or benzpiperidinyl optionally substituted with 1 to 3 groups of $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl, said $R^a$ groups optionally substituted with 1-3 groups of $R^b$.

7. The compound according to claim 1 of formula (I) represented by structural formula Ia':

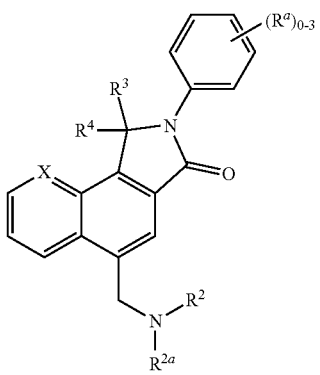

or a pharmaceutically acceptable salt thereof wherein $R^3$ and $R^4$ are both hydrogen, or one of $R^3$ and $R^4$ is hydrogen and the other is methyl, and $R^2$ and $R^{2a}$ are $C_{1-6}$ alkyl or combine to form piperidinyl, piperazinyl, morpholinyl, pyrrolidinyl, or benzpiperidinyl, said alkyl, piperidinyl, piperazinyl, morpholinyl, pyrrolidinyl, or benzpiperidinyl optionally substituted with 1 to 3 groups of $R^a$ selected from the group consisting of $C_{1-6}$alkyl, CN, halo, $(CH_2)_nCF_3$, OH, $(CH_2)_n$phenyl, $(CH_2)_n$pyridyl, piperazinyl, pyrimidinyl, pyrazolyl, and $C_{2-6}$alkynyl, said Ra groups optionally substituted with 1 to 3 groups of $R^b$.

8. The compound according to claim 1 of formula (I) represented by structural formula Ia":

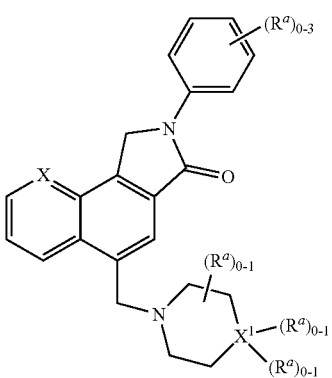

wherein $X^1$ is CH or N and X and $R^a$ are as originally described, and pharmaceutically acceptable salts thereof.

9. The compound according to claim 1 of formula (I) represented by structural formula Ib:

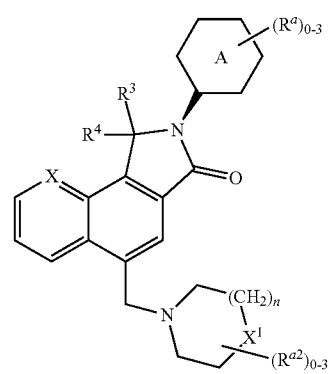

or a pharmaceutically acceptable salt thereof wherein X and $X^1$ are as originally described, $R^3$ and $R^4$ are both hydrogen or one of $R^3$ and $R^4$ is hydrogen and the other is methyl, A is selected from the group consisting of optionally substituted cyclohexyl and pyranyl, n is 0 or 1, and $R^{a2}$ is $R^a$.

10. The compound according to claim 1 represented by structural formulas Ib''' or Ib'''':

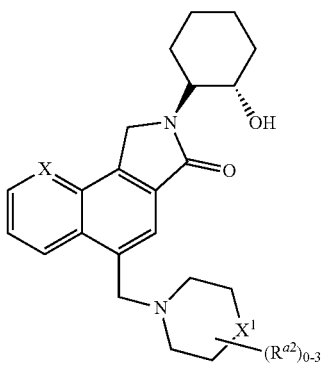

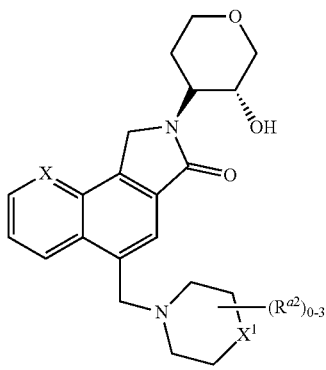

and pharmaceutically acceptable salts thereof.

11. The compound according to claim 9 wherein n is 1, A is hydroxycyclohexyl or hydroxypyranyl, $R^{a2}$ is 0-2 and is selected from the group consisting of methyl, ethyl, propyl, butyl, fluorine, chlorine, bromine, —O—, OH, CN, $(CH_2)_n$ $CF_3$, $CH_2F$, $C_{2-4}$ alkenyl, $C_{2-4}$ alkynyl, $C_{2-4}$ alkynylphenyl, $(CH_2)_n$pyridyl, methxoxy, $SO_2Me$, COOEt, cyclopropyl, $(CH_2)_n$phenyl, pyrimidinyl, pyrazinyl, pyridazinyl, benzypiperidinyl, pyrazolyl, benzothiazolyl, quinolinyl, said alkyl, aryl and heterocyclyl groups of $R^{a2}$ optionally substituted with 1 to 3 groups of $R^b$, and pharmaceutically acceptable salts thereof.

12. A compound which is
1-({2-[(1S,2S)-2-hydroxycyclohexyl]-3-oxo-2,3-dihydro-1H-benzo[e]isoindol-5-yl}methyl)-4-(pyridine-2-yl)piperidine-4-carbonitrile,
5-{[4-Fluoro-4-(pyridine-2-yl)piperidine-1-yl]methyl}-2-[(1S,2S)-2-hydroxycyclohexyl]-1,2-dihydro-3H-benzo[e]isoindol-3-one,
1-({2-[(1S,2S)-2-Hydroxycyclohexyl]-1-methyl-3-oxo-2,3-dihydro-1H-benzo[e]isoindol-5-yl}methyl)-4-(pyridine-2-yl)piperidine-4-carbonitrile,
1-({2-[(1S,2S)-2-Hydroxycyclohexyl]-3-oxo-2,3-dihydro-1H-benzo[e]isoindol-5-yl}methyl)-4-(6-methylpyridin-2-yl)piperidine-4-carbonitrile,
4-(6-Ethylpyridin-2-yl)-1-({2-[(1S,2S)-hydroxycyclohexyl]-3-oxo-2,3-dihydro-1H-benzo[e]isoindol-5-yl}methyl)piperidine-4-carbonitrile,
1-({2-[(1S,2S)-2-Hydroxycyclohexyl]-3-oxo-2,3-dihydro-1H-benzo[e]isoindol-5-yl}methyl)-4-(6-methoxypyridin-2-yl)piperidine-4-carbonitrile,
1,5-Anhydro-2,3-dideoxy-3-{5-[(4,4-difluoropiperidin-1-yl)methyl]-7-oxo-7,9-dihydro-8H-pyrrolo[3,4-h]quinolin-8-yl}-L-threo-pentitol,
1,5-Anhydro-2,4-dideoxy-2-{5-[(4,4-difluoropiperidin-1-yl)methyl]-7-oxo-7,9-dihydro-8H-pyrrolo[3,4-h]quinolin-8-yl}-L-threo-pentitol,
5-[(4-Ethenyl-4-fluoropiperidin-1-yl)methyl]-8-[(1S,2S)-2-hydroxycyclohexyl]-8,9-dihydro-7H-pyrrolo[3,4-h]quinolin-7-one,
3-{5-[(4,4-Difluoropiperidin-1-yl)methyl]-7-oxo-7,9-dihydro-8H-pyrrolo[3,4-h]quinolin-8-yl}phenyl dimethylcarbamate,
2-(2-Hydroxycyclohexyl)-5-(piperidin-1-ylmethyl)-1,2-dihydro-3H-benzo[e]isoindol-3-one,
2-[(1S,2S)-2-hydroxycyclohexyl]-5-[(4-methylpiperazin-1-yl)methyl]-1,2-dihydro-3H-benzo[e]isoindol-3-one,
2-[(1S,2S)-2-hydroxycyclohexyl]-5-[(4-methyl-3-oxopiperazin-1-yl)methyl]-1,2-dihydro-3H-benzo[e]isoindol-3-one,
5-[(4-acetylpiperazin-1-yl)methyl]-2-(2-hydroxycyclohexyl)-1,2-dihydro-3H-benzo[e]isoindol-3-one,
2-(2-hydroxycyclohexyl)-5-{[4-(methylsulfonyl)piperazin-1-yl]methyl}-1,2-dihydro-3H-benzo[e]isoindol-3-one,
2-(2-hydroxycyclohexyl)-5-[(3-methylpiperidin-1-yl)methyl]-1,2-dihydro-3H-benzo[e]isoindol-3-one,
5-[(3-fluoropiperidin-1-yl)methyl]-2-(2-hydroxycyclohexyl)-1,2-dihydro-3H-benzo[e]isoindol-3-one,
5-[(3,3-difluoropiperidin-1-yl)methyl]-2-(2-hydroxycyclohexyl)-1,2-dihydro-3H-benzo[e]isoindol-3-one,
4-fluoro-1-({2-[(1S,2S)-2-hydroxycyclohexyl]-3-oxo-2,3-dihydro-1H-benzo[e]isoindol-5-yl}methyl)piperidine-4-carbonitrile,
1-({2-[(1S,2S)-2-hydroxycyclohexyl]-3-oxo-2,3-dihydro-1H-benzo[e]isoindol-5-yl}methyl)piperidine-4-carbonitrile,
2-[(1S,2S)-2-hydroxycyclohexyl]-5-[(4-methylpiperidin-1-yl)methyl]-1,2-dihydro-3H-benzo[e]isoindol-3-one,
2-(2-hydroxycyclohexyl)-5-[(4-hydroxypiperidin-1-yl)methyl]-1,2-dihydro-3H-benzo[e]isoindol-3-one,
2-(2-Hydroxycyclohexyl)-5-(pyrrolidin-1-ylmethyl)-1,2-dihydro-3H-benzo[e]isoindol-3-one,
2-(2-hydroxycyclohexyl)-5-(morpholin-4-ylmethyl)-1,2-dihydro-3H-benzo[e]isoindol-3-one,
5-[(4,4-difluoropiperidin-1-yl)methyl]-2-(2-hydroxycyclohexyl)-1,2-dihydro-3H-benzo[e]isoindol-3-one,
5-[(4-fluoropiperidin-1-yl)methyl]-2-(2-hydroxycyclohexyl)-1,2-dihydro-3H-benzo[e]isoindol-3-one,
2-(2-hydroxycyclohexyl)-5-{[4-(trifluoromethyl)piperidin-1-yl]methyl}-1,2-dihydro-3H-benzo[e]isoindol-3-one,
5-[(3-fluoro-4-hydroxypyrrolidin-1-yl)methyl]-2-(2-hydroxycyclohexyl)-1,2-dihydro-3H-benzo[e]isoindol-3-one,
5-{[trans-3,4-difluoropyrrolidin-1-yl]methyl}-2-(2-hydroxycyclohexyl)-1,2-dihydro-3H-benzo[e]isoindol-3-one,
2-(2-hydroxycyclohexyl)-5-{[2-(trifluoromethyl)pyrrolidin-1-yl]methyl}-1,2-dihydro-3H-benzo[e]isoindol-3-one,
5-{[3-(fluoromethyl)pyrrolidin-1-yl]methyl}-2-(2-hydroxycyclohexyl)-1,2-dihydro-3H-benzo[e]isoindol-3-one,
5-{[(3S)-3-fluoropyrrolidin-1-yl]methyl}-2-(2-hydroxycyclohexyl)-1,2-dihydro-3H-benzo[e]isoindol-3-one,
5-[(3,3-difluoropyrrolidin-1-yl)methyl]-2-(2-hydroxycyclohexyl)-1,2-dihydro-3H-benzo[e]isoindol-3-one,
2-(2-hydroxycyclohexyl)-5-{[4-(2,2,2-trifluoroethyl)piperazin-1-yl]methyl}-1,2-dihydro-3H-benzo[e]isoindol-3-one,
ethyl 4-fluoro-1-{[2-(2-hydroxycyclohexyl)-3-oxo-2,3-dihydro-1H-benzo[e]isoindol-5-yl]methyl}piperidine-4-carboxylate,
2-(2-hydroxycyclohexyl)-5-(2-oxa-7-azaspiro[3.5]non-7-ylmethyl)-1,2-dihydro-3H-benzo[e]isoindol-3-one,
2-(2-hydroxycyclohexyl)-5-[(4-hydroxy-4-methylpiperidin-1-yl)methyl]-1,2-dihydro-3H-benzo[e]isoindol-3-one,
5-[(4,4-dimethylpiperidin-1-yl)methyl]-2-(2-hydroxycyclohexyl)-1,2-dihydro-3H-benzo[e]isoindol-3-one,
5-[(4-cyclopropylpiperidin-1-yl)methyl]-2-(2-hydroxycyclohexyl)-1,2-dihydro-3H-benzo[e]isoindol-3-one,
2-(2-hydroxycyclohexyl)-5-(1'H-spiro[1-benzofuran-3,4'-piperidin]-1'-ylmethyl)-1,2-dihydro-3H-benzo[e]isoindol-3-one, 2-(2-hydroxycyclohexyl)-5-[(4-phenylpiperidin-1-yl)methyl]-1,2-dihydro-3H-benzo[e]isoindol-3-one,
2-(2-hydroxycyclohexyl)-5-[(4-(4-pyridinyl)piperidin-1-yl)methyl]-1,2-dihydro-3H-benzo[e]isoindol-3-one,
2-(2-hydroxycyclohexyl)-5-[(4-hydroxy-4-pyridin-4-ylpiperidin-1-yl)methyl]-1,2-dihydro-3H-benzo[e]isoindol-3-one,
1-({2-[(1S,2S)-2-hydroxycyclohexyl]-1-methyl-3-oxo-2,3-dihydro-1H-benzo[e]isoindol-5-yl}methyl)-4-(pyridin-2-yl)piperidine-4-carbonitrile,
1-({2-[(1R,2R)-2-hydroxycyclohexyl]-3-oxo-2,3-dihydro-1H-benzo[e]isoindol-5-yl}methyl)-4-pyridin-2-ylpiperidine-4-carbonitrile,
1-({2-[(1R,2S)-2-hydroxycyclohexyl]-3-oxo-2,3-dihydro-1H-benzo[e]isoindol-5-yl}methyl)-4-pyridin-2-ylpiperidine-4-carbonitrile,
4-(6-chloropyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile, 4-(6-ethenylpyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile,
4-(6-ethenylpyridin-2-yl)-1-({2-[(1S,2S)-2-hydroxycyclohexyl]-3-oxo-2,3-dihydro-1H-benzo[e]isoindol-5-yl}methyl)piperidine-4-carbonitrile,
1-({2-[(1S,2S)-2-hydroxycyclohexyl]-3-oxo-2,3-dihydro-1H-benzo[e]isoindol-5-yl}methyl)-4-(pyrazin-2-yl)piperidine-4-carbonitrile,
1-({2-[(1S,2S)-2-hydroxycyclohexyl]-3-oxo-2,3-dihydro-1H-benzo[e]isoindol-5-yl}methyl)-4-(pyrimidin-4-yl)piperidine-4-carbonitrile,
1-({2-[(1S,2S)-2-hydroxycyclohexyl]-3-oxo-2,3-dihydro-1H-benzo[e]isoindol-5-yl}methyl)-4-(pyridazin-3-yl)piperidine-4-carbonitrile, 5-[(4-fluoro-4-phenylpiperidin-1-yl)methyl]-2-[(1R,2R)-2-hydroxycyclohexyl]-1,2-dihydro-3H-benzo[e]isoindol-3-one,
1-{[3-oxo-2-(tetrahydro-2H-pyran-4-yl)-2,3-dihydro-1H-benzo[e]isoindol-5-yl]methyl}-4-pyridin-2-ylpiperidine-4-carbonitrile,
1-{[3-oxo-2-(tetrahydro-2H-pyran-3-yl)-2,3-dihydro-1H-benzo[e]isoindol-5-yl]methyl}-4-pyridin-2-ylpiperidine-4-carbonitrile,
1-({2-[(1S,2S)-2-hydroxycyclohexyl]-3-oxo-2,3-dihydro-1H-benzo[e]isoindol-5-yl}methyl)-4-phenylpiperidine-4-carbonitrile,
1-({2-[(1S,2S)-2-hydroxycyclohexyl]-3-oxo-2,3-dihydro-1H-benzo[e]isoindol-5-yl}methyl)-4-pyridin-3-ylpiperidine-4-carbonitrile,
1-({2-[(1S,2S)-2-hydroxycyclohexyl]-3-oxo-2,3-dihydro-1H-benzo[e]isoindol-5-yl}methyl)-4-pyridin-4-ylpiperidine-4-carbonitrile,
4-(2-chlorophenyl)-1-({2-[(1S,2S)-2-hydroxycyclohexyl]-3-oxo-2,3-dihydro-1H-benzo[e]isoindol-5-yl}methyl)piperidine-4-carbonitrile,
4-(2-fluorophenyl)-1-({2-[(1R,2S)-2-hydroxycyclohexyl]-3-oxo-2,3-dihydro-1H-benzo[e]isoindol-5-yl}methyl)piperidine-4-carbonitrile,
1-({2-[(1R,2S)-2-hydroxycyclohexyl]-3-oxo-2,3-dihydro-1H-benzo[e]isoindol-5-yl}methyl)-4-(2-methylphenyl)piperidine-4-carbonitrile,
1-{[2-(2-fluorophenyl)-3-oxo-2,3-dihydro-1H-benzo[e]isoindol-5-yl]methyl}-4-pyridin-2-ylpiperidine-4-carbonitrile,
1-({2-[(1S,2S)-2-hydroxycyclohexyl]-3-oxo-2,3-dihydro-1H-benzo[e]isoindol-5-yl}methyl)-4-(4-methylpyridin-2-yl)piperidine-4-carbonitrile,
5-{[4-(4-fluorophenyl)piperazin-1-yl]methyl}-2-[(1S,2S)-2-hydroxycyclohexyl]-1,2-dihydro-3H-benzo[e]isoindol-3-one,
2-[(1S,2S)-2-hydroxycyclohexyl]-5-({4-[4-(methylsulfonyl)phenyl]piperazin-1-yl}methyl)-1,2-dihydro-3H-benzo[e]isoindol-3-one,
2-[(1S,2S)-2-hydroxycyclohexyl]-5-{[4-(4-methoxyphenyl)piperazin-1-yl]methyl}-1,2-dihydro-3H-benzo[e]isoindol-3-one,
2-[(1S,2S)-2-hydroxycyclohexyl]-5-{[4-(4-methoxyphenyl)-2-methylpiperazin-1-yl]methyl}-1,2-dihydro-3H-benzo[e]isoindol-3-one,
2-[(1S,2S)-2-hydroxycyclohexyl]-5-{[5-(4-methoxyphenyl)-2,5-diazabicyclo[2.2.1]hept-2-yl]methyl}-1,2-dihydro-3H-benzo[e]isoindol-3-one,
2-[(1S,2S)-2-hydroxycyclohexyl]-5-[(4-phenylpiperazin-1-yl)methyl]-1,2-dihydro-3H-benzo[e]isoindol-3-one,
2-[(1R,2S)-2-hydroxycyclohexyl]-1-methyl-5-[(4-phenylpiperazin-1-yl)methyl]-1,2-dihydro-3H-benzo[e]isoindol-3-one,
2-[(1S,2S)-2-hydroxycyclohexyl]-5-[(4-pyridin-2-ylpiperazin-1-yl)methyl]-1,2-dihydro-3H-benzo[e]isoindol-3-one,
2-[(1S,2S)-2-hydroxycyclohexyl]-5-[(4-pyridin-3-ylpiperazin-1-yl)methyl]-1,2-dihydro-3H-benzo[e]isoindol-3-one,
2-[(1S,2S)-2-hydroxycyclohexyl]-5-[(4-pyridin-4-ylpiperazin-1-yl)methyl]-1,2-dihydro-3H-benzo[e]isoindol-3-one,
2-[(1S,2S)-2-hydroxycyclohexyl]-5-[(3-methyl-4-phenylpiperazin-1-yl)methyl]-1,2-dihydro-3H-benzo[e]isoindol-3-one,
2-[(1S,2S)-2-hydroxycyclohexyl]-5-{[4-(1-methyl-1H-pyrazol-4-yl)piperazin-1-yl]methyl}-1,2-dihydro-3H-benzo[e]isoindol-3-one,
2-[(1S,2S)-2-hydroxycyclohexyl]-5-{[4-(1-methyl-1H-pyrazol-4-yl)piperazin-1-yl]methyl}-1,2-dihydro-3H-benzo[e]isoindol-3-one,
2-[(1R,2R)-2-hydroxycyclohexyl]-5-{[4-(1-methyl-1H-pyrazol-4-yl)piperazin-1-yl]methyl}-1,2-dihydro-3H-benzo[e]isoindol-3-one,
5-{[4-(1-methyl-1H-pyrazol-4-yl)piperazin-1-yl]methyl}-2-(tetrahydro-2H-pyran-4-yl)-1,2-dihydro-3H-benzo[e]isoindol-3-one,
5-{[4-(1-methyl-1H-pyrazol-4-yl)piperazin-1-yl]methyl}-2-(tetrahydro-2H-pyran-3-yl)-1,2-dihydro-3H-benzo[e]isoindol-3-one,
2-(2-fluorophenyl)-5-[(4-isoquinolin-3-ylpiperazin-1-yl)methyl]-1,2-dihydro-3H-benzo[e]isoindol-3-one,
5-{[4-(1,3-benzothiazol-6-yl)piperazin-1-yl]methyl}-2-(2-fluorophenyl)-1,2-dihydro-3H-benzo[e]isoindol-3-one,
8-[(1S,2S)-2-hydroxycyclohexyl]-5-(piperidin-1-ylmethyl)-8,9-dihydro-7H-pyrrolo[3,4-h]quinolin-7-one,
8-[(1S,2S)-2-hydroxycyclohexyl]-5-[(4-methylpiperidin-1-yl)methyl]-8,9-dihydro-7H-pyrrolo[3,4-h]quinolin-7-one,
5-[(diethylamino)methyl]-8-(2-hydroxycyclohexyl)-8,9-dihydro-7H-pyrrolo[3,4-h]quinolin-7-one,
8-(2-hydroxycyclohexyl)-5-[(4-hydroxypiperidin-1-yl)methyl]-8,9-dihydro-7H-pyrrolo[3,4-h]quinolin-7-one,
5-[(4-cyclopropylpiperidin-1-yl)methyl]-8-(2-hydroxycyclohexyl)-8,9-dihydro-7H-pyrrolo[3,4-h]quinolin-7-one,
5-[(4-fluoropiperidin-1-yl)methyl]-8-(2-hydroxycyclohexyl)-8,9-dihydro-7H-pyrrolo[3,4-h]quinolin-7-one, 1-({8-[(1S,2S)-2-hydroxycyclohexyl]-7-oxo-8,9-dihydro-7H-pyrrolo[3,4-h]quinolin-5-yl}methyl)piperidine-4-carbonitrile, 5-[(4-fluoropiperidin-1-yl)methyl]-8-[(1S,2S)-2-hydroxycyclohexyl]-9-methyl-8,9-dihydro-7H-pyrrolo[3,4-h]quinolin-7-one, 1-({8-[(1S,2S)-2-hydroxycyclohexyl]-7-oxo-8,9-dihydro-7H-pyrrolo[3,4-h]quinolin-5-yl}methyl)piperidine-4-carbonitrile, 8-(2-hydroxycyclohexyl)-5-(1'H-spiro[1-benzofuran-3,4'-piperidin]-1'-ylmethyl)-8,9-dihydro-7H-pyrrolo[3,4-h]quinolin-7-one, 8-(2-hydroxycyclohexyl)-5-(2-oxa-7-azaspiro[3.5]non-7-ylmethyl)-8,9-dihydro-7H-pyrrolo[3,4-h]quinolin-7-one, 8-(2-hydroxycyclohexyl)-5-(pyrrolidin-1-ylmethyl)-8,9-dihydro-7H-pyrrolo[3,4-h]quinolin-7-one, 5-[(3,3-difluoropyrrolidin-1-yl)methyl]-8-(2-hydroxycyclohexyl)-8,9-dihydro-7H-pyrrolo[3,4-h]quinolin-7-one, 8-(2-hydroxycyclohexyl)-5-(morpholin-4-ylmethyl)-8,9-dihydro-7H-pyrrolo[3,4-h]quinolin-7-one, 5-[(4,4-dimethylpiperidin-1-yl)methyl]-8-(2-hydroxycyclohexyl)-8,9-dihydro-7H-pyrrolo[3,4-h]quinolin-7-one, 8-(2-hydroxycyclohexyl)-5-[(4-hydroxy-4-methylpiperidin-1-yl)methyl]-8,9-dihydro-7H-pyrrolo[3,4-h]quinolin-7-one, 5-[(4-fluoro-4-methylpiperidin-1-yl)methyl]-8-[(1S,2S)-2-hydroxycyclohexyl]-8,9-dihydro-7H-pyrrolo[3,4-h]quinolin-7-one, 5-[(4-ethynyl-4-fluoropiperidin-1-yl)methyl]-8-[(1S,2S)-2-hydroxycyclohexyl]-8,9-dihydro-7H-pyrrolo[3,4-h]quinolin-7-one, 5-[(4,4-difluoropiperidin-1-yl)methyl]-8-[(1R,2S)-2-hydroxycyclohexyl]-9-methyl-8,9-dihydro-7H-pyrrolo[3,4-h]quinolin-7-one, 5-[(4,4-difluoropiperidin-1-yl)methyl]-9-ethyl-8-[(1R,2S)-2-hydroxycyclohexyl]-8,9-dihydro-7H-pyrrolo[3,4-h]quinolin-7-one, 1,5-anhydro-2,4-dideoxy-4-{5-[(4,4-difluoropiperidin-1-yl)methyl]-9-methyl-7-oxo-7,9-dihydro-8H-pyrrolo[3,4-h]quinolin-8-yl}-D-erythro-pentitol, 1,5-anhydro-3,4-dideoxy-3-{5-[(4,4-difluoropiperidin-1-yl)methyl]-9-methyl-7-oxo-7,9-dihydro-8H-pyrrolo[3,4-h]quinolin-8-yl}-D-erythro-pentitol, 1,5-anhydro-3-{5-[(4-cyano-4-pyridin-2-ylpiperidin-1-yl)methyl]-9-methyl-7-oxo-7,9-dihydro-8H-pyrrolo[3,4-h]quinolin-8-yl}-2,3-dideoxypentitol, 1,5-anhydro-3-(5-{[4-cyano-4-(4-methylpyridin-2-yl)piperidin-1-yl]methyl}-9-methyl-7-oxo-7,9-dihydro-8H-pyrrolo[3,4-h]quinolin-8-yl)-2,3-dideoxypentitol, 1,5-anhydro-3-{5-[(4-cyano-4-fluoropiperidin-1-yl)methyl]-9-methyl-7-oxo-7,9-dihydro-8H-pyrrolo[3,4-h]quinolin-8-yl}-2,3-dideoxypentitol, 1,5-anhydro-3-{5-[(4-fluoropiperidin-1-yl)methyl]-9-methyl-7-oxo-7,9-dihydro-8H-pyrrolo[3,4-h]quinolin-8-yl}-2,3-dideoxypentitol, 1,5-anhydro-3-{5-[(4-cyanopiperidin-1-yl)methyl]-9-methyl-7-oxo-7,9-dihydro-8H-pyrrolo[3,4-h]quinolin-8-yl}-2,3-dideoxypentitol, 1,5-anhydro-2,3-dideoxy-3-{5-[(4-ethynylpiperidin-1-yl)methyl]-9-methyl-7-oxo-7,9-dihydro-8H-pyrrolo[3,4-h]quinolin-8-yl}pentitol, 1,5-anhydro-2,3-dideoxy-3-{5-[(4-ethynyl-4-fluoropiperidin-1-yl)methyl]-9-methyl-7-oxo-7,9-dihydro-8H-pyrrolo[3,4-h]quinolin-8-yl}pentitol, 1,5-anhydro-2,3-dideoxy-3-{5-[(4-fluoro-4-prop-1-yn-1-ylpiperidin-1-yl)methyl]-9-methyl-7-oxo-7,9-dihydro-8H-pyrrolo[3,4-h]quinolin-8-yl}pentitol, 5-[(4,4-difluoropiperidin-1-yl)methyl]-8-(2-hydroxycyclohexyl)-8,9-dihydro-7H-pyrrolo[3,4-h]quinolin-7-one, 4-fluoro-1-({8-[(1S,2S)-2-hydroxycyclohexyl]-7-oxo-8,9-dihydro-7H-pyrrolo[3,4-h]quinolin-5-yl}methyl)piperidine-4-carbonitrile, 4-fluoro-1-{[8-(2-hydroxycyclohexyl)-9-methyl-7-oxo-8,9-dihydro-7H-pyrrolo[3,4-h]quinolin-5-yl]methyl}piperidine-4-carbonitrile, 4-fluoro-1-{[8-(2-hydroxycyclohexyl)-9-methyl-7-oxo-8,9-dihydro-7H-pyrrolo[3,4-h]quinolin-5-yl]methyl}piperidine-4-carbonitrile, 1-({9-ethyl-8-[(1R,2S)-2-hydroxycyclohexyl]-7-oxo-8,9-dihydro-7H-pyrrolo[3,4-h]quinolin-5-yl}methyl)-4-fluoropiperidine-4-carbonitrile, 5-[(3-fluoropiperidin-1-yl)methyl]-8-(2-hydroxycyclohexyl)-8,9-dihydro-7H-pyrrolo[3,4-h]quinolin-7-one, 5-[(3,3-difluoropiperidin-1-yl)methyl]-8-(2-hydroxycyclohexyl)-8,9-dihydro-7H-pyrrolo[3,4-h]quinolin-7-one, 8-(2-hydroxycyclohexyl)-5-{[4-(trifluoromethyl)piperidin-1-yl]methyl}-8,9-dihydro-7H-pyrrolo[3,4-h]quinolin-7-one, 5-[(4-ethynylpiperidin-1-yl)methyl]-8-(2-hydroxycyclohexyl)-8,9-dihydro-7H-pyrrolo[3,4-h]quinolin-7-one, 5-[(4-fluoro-4-pent-1-yn-1-ylpiperidin-1-yl)methyl]-8-[(iS,2S)-2-hydroxycyclohexyl]-8,9-dihydro-7H-pyrrolo[3,4-h]quinolin-7-one, 4-fluoro-1-{[8-(3-hydroxyphenyl)-7-oxo-8,9-dihydro-7H-pyrrolo[3,4-h]quinolin-5-yl]methyl}piperidine-4-carbonitrile, 5-[(4-ethynyl-4-fluoropiperidin-1-yl)methyl]-8-(3-hydroxyphenyl)-8,9-dihydro-7H-pyrrolo[3,4-h]quinolin-7-one, 3-{5-[(4-cyano-4-fluoropiperidin-1-yl)methyl]-7-oxo-7,9-dihydro-8H-pyrrolo[3,4-h]quinolin-8-yl}phenyl dimethylcarbamate, 3-{5-[(4-ethynyl-4-fluoropiperidin-1-yl)methyl]-7-oxo-7,9-dihydro-8H-pyrrolo[3,4-h]quinolin-8-yl}phenyl dimethylcarbamate, 5-[(4-fluoro-4-prop-1-yn-1-ylpiperidin-1-yl)methyl]-8-[(1S,2S)-2-hydroxycyclohexyl]-8,9-dihydro-7H-pyrrolo[3,4-h]quinolin-7-one, 5-{[4-(cyclopropylethynyl)-4-fluoropiperidin-1-yl]methyl}-8-[(1S,2S)-2-hydroxycyclo-hexyl]-8,9-dihydro-7H-pyrrolo[3,4-h]quinolin-7-one, 5-({4-fluoro-4-[(4-fluorophenyl)ethynyl]piperidin-1-yl}methyl)-8-(2-hydroxycyclo-hexyl)-8,9-dihydro-7H-pyrrolo[3,4-h]quinolin-7-one, 5-[(4-benzyl-4-fluoropiperidin-1-yl)methyl]-8-(2-hydroxycyclohexyl)-8,9-dihydro-7H-pyrrolo[3,4-h]quinolin-7-one, 1-{[8-(2-hydroxycyclohexyl)-7-oxo-8,9-dihydro-7H-pyrrolo[3,4-h]quinolin-5-yl]methyl}-4-(pyridin-4-ylmethyl)piperidine-4-carbonitrile, 1-({8-[(1S,2S)-2-hydroxycyclohexyl]-7-oxo-8,9-dihydro-7H-pyrrolo[3,4-h]quinolin-5-yl}methyl)-4-phenylpiperidine-4-carbonitrile, 1-{[8-(2-hydroxycyclohexyl)-9-methyl-7-oxo-8,9-dihydro-7H-pyrrolo[3,4-h]quinolin-5-yl]methyl}-4-phenylpiperidine-4-carbonitrile, 8-(2-hydroxycyclohexyl)-5-[(4-phenylpiperidin-1-yl)methyl]-8,9-dihydro-7H-pyrrolo[3,4-h]quinolin-7-one, 8-(2-hydroxycyclohexyl)-9-methyl-5-[(4-phenylpiperidin-1-yl)methyl]-8,9-dihydro-7H-pyrrolo[3,4-h]quinolin-7-one,
8-(2-hydroxycyclohexyl)-5-[(4-pyridin-4-ylpiperidin-1-yl)methyl]-8,9-dihydro-7H-pyrrolo[3,4-h]quinolin-7-one,
8-(2-hydroxycyclohexyl)-5-[(4-hydroxy-4-pyridin-4-ylpiperidin-1-yl)methyl]-8,9-dihydro-7H-pyrrolo[3,4-h]quinolin-7-one,
8-(2-hydroxycyclohexyl)-9-methyl-5-[(4-pyridin-4-ylpiperidin-1-yl)methyl]-8,9-dihydro-7H-pyrrolo[3,4-h]quinolin-7-one,
1-({8-[(1S,2S)-2-hydroxycyclohexyl]-7-oxo-8,9-dihydro-7H-pyrrolo[3,4-h]quinolin-5-yl}methyl)-4-pyridin-2-ylpiperidine-4-carbonitrile,
5-[(4-fluoro-4-pyridin-2-ylpiperidin-1-yl)methyl]-8-(2-hydroxycyclohexyl)-8,9-dihydro-7H-pyrrolo[3,4-h]quinolin-7-one,
5-[(4-fluoro-4-pyridin-2-ylpiperidin-1-yl)methyl]-8-[(1R,2S)-2-hydroxycyclohexyl]-9-methyl-8,9-dihydro-7H-pyrrolo[3,4-h]quinolin-7-one,
1-{[8-(2-hydroxycyclohexyl)-7-oxo-8,9-dihydro-7H-pyrrolo[3,4-h]quinolin-5-yl]methyl}-4-(4-methylpyridin-2-yl)piperidine-4-carbonitrile,
1-({(9R)-8-[(1S,2S)-2-hydroxycyclohexyl]-9-methyl-7-oxo-8,9-dihydro-7H-pyrrolo[3,4-h]quinolin-5-yl}methyl)-4-pyridin-2-ylpiperidine-4-carbonitrile,
1-({(9R)-8-[(1S,2S)-2-hydroxycyclohexyl]-9-methyl-7-oxo-8,9-dihydro-7H-pyrrolo[3,4-h]quinolin-5-yl}methyl)-4-pyridin-2-ylpiperidine-4-carbonitrile,
1-({(9R)-8-[(1S,2S)-2-hydroxycyclohexyl]-9-methyl-7-oxo-8,9-dihydro-7H-pyrrolo[3,4-h]quinolin-5-yl}methyl)-4-(4-methylpyridin-2-yl)piperidine-4-carbonitrile,
1-({(9R)-8-[(1S,2S)-2-hydroxycyclohexyl]-9-methyl-7-oxo-8,9-dihydro-7H-pyrrolo[3,4-h]quinolin-5-yl}methyl)-4-(4-methylpyridin-2-yl)piperidine-4-carbonitrile,
(9R)-5-[(4-fluoro-4-pyridin-2-ylpiperidin-1-yl)methyl]-8-[(1S,2S)-2-hydroxycyclohexyl]-9-methyl-8,9-dihydro-7H-pyrrolo[3,4-h]quinolin-7-one,
1-({8-[(1S,2S)-2-hydroxycyclohexyl]-7-oxo-8,9-dihydro-7H-pyrrolo[3,4-h]quinolin-5-yl}methyl)-4-(6-methoxypyridin-2-yl)piperidine-4-carbonitrile,
1-({8-[(1S,2S)-2-hydroxycyclohexyl]-7-oxo-8,9-dihydro-7H-pyrrolo[3,4-h]quinolin-5-yl}methyl)-4-(6-methoxypyridin-2-yl)piperidine-4-carbonitrile,
1-({8-[(1S,2S)-2-hydroxycyclohexyl]-7-oxo-8,9-dihydro-7H-pyrrolo[3,4-h]quinolin-5-yl}methyl)-4-(6-methoxypyridin-2-yl)piperidine-4-carbonitrile,
8-[(1S,2S)-2-hydroxycyclohexyl]-5-{[4-(1-methyl-1H-pyrazol-4-yl)piperazin-1-yl]methyl}-8,9-dihydro-7H-pyrrolo[3,4-h]quinolin-7-one,
8-(2-hydroxycyclohexyl)-9-methyl-5-{[4-(1-methyl-1H-pyrazol-4-yl)piperazin-1-yl]methyl}-8,9-dihydro-7H-pyrrolo[3,4-h]quinolin-7-one,
8-(2-hydroxycyclohexyl)-5-[(4-pyridin-4-ylpiperazin-1-yl)methyl]-8,9-dihydro-7H-pyrrolo[3,4-h]quinolin-7-one,
8-(2-hydroxycyclohexyl)-9-methyl-5-[(4-pyridin-4-ylpiperidin-1-yl)methyl]-8,9-dihydro-7H-pyrrolo[3,4-h]quinolin-7-one,
8-(2-hydroxycyclohexyl)-5-[(4-pyridin-3-ylpiperazin-1-yl)methyl]-8,9-dihydro-7H-pyrrolo[3,4-h]quinolin-7-one,
8-(2-hydroxycyclohexyl)-9-methyl-5-[(4-pyridin-3-ylpiperazin-1-yl)methyl]-8,9-dihydro-7H-pyrrolo[3,4-h]quinolin-7-one,
8-(2-hydroxycyclohexyl)-9-methyl-5-[(4-pyridin-3-ylpiperazin-1-yl)methyl]-8,9-dihydro-7H-pyrrolo[3,4-h]quinolin-7-one,
8-(2-hydroxycyclohexyl)-5-[(4-pyridin-2-ylpiperazin-1-yl)methyl]-8,9-dihydro-7H-pyrrolo[3,4-h]quinolin-7-one,
8-(2-hydroxycyclohexyl)-9-methyl-5-[(4-pyridin-2-ylpiperazin-1-yl)methyl]-8,9-dihydro-7H-pyrrolo[3,4-h]quinolin-7-one,
8-(2-hydroxycyclohexyl)-9-methyl-5-[(4-pyridin-2-ylpiperazin-1-yl)methyl]-8,9-dihydro-7H-pyrrolo[3,4-h]quinolin-7-one,
8-(2-hydroxycyclohexyl)-5-{[4-(4-methoxyphenyl)piperazin-1-yl]methyl}-8,9-dihydro-7H-pyrrolo[3,4-h]quinolin-7-one,
8-(2-hydroxycyclohexyl)-5-{[4-(4-methoxyphenyl)piperazin-1-yl]methyl}-9-methyl-8,9-dihydro-7H-pyrrolo[3,4-h]quinolin-7-one,
8-(2-hydroxycyclohexyl)-5-{[4-(4-methoxyphenyl)piperazin-1-yl]methyl}-9-methyl-8,9-dihydro-7H-pyrrolo[3,4-h]quinolin-7-one,
5-{[4-(4-fluorophenyl)piperazin-1-yl]methyl}-8-(2-hydroxycyclohexyl)-8,9-dihydro-7H-pyrrolo[3,4-h]quinolin-7-one,
5-{[4-(4-fluorophenyl)piperazin-1-yl]methyl}-8-(2-hydroxycyclohexyl)-9-methyl-8,9-dihydro-7H-pyrrolo[3,4-h]quinolin-7-one,
5-{[4-(4-fluorophenyl)piperazin-1-yl]methyl}-8-(2-hydroxycyclohexyl)-9-methyl-8,9-dihydro-7H-pyrrolo[3,4-h]quinolin-7-one,
8-(2-hydroxycyclohexyl)-5-[(4-phenylpiperazin-1-yl)methyl]-8,9-dihydro-7H-pyrrolo[3,4-h]quinolin-7-one,
8-(2-hydroxycyclohexyl)-9-methyl-5-[(4-phenylpiperazin-1-yl)methyl]-8,9-dihydro-7H-pyrrolo[3,4-h]quinolin-7-one,
8-(2-hydroxycyclohexyl)-9-methyl-5-[(4-phenylpiperazin-1-yl)methyl]-8,9-dihydro-7H-pyrrolo[3,4-h]quinolin-7-one
1-({2-[(1S,2S)-2-hydroxycyclohexyl]-1-methyl-3-oxo-2,3-dihydro-1H-benzo[e]isoindol-5-yl}methyl)-4-(pyridin-2-yl)piperidine-4-carbonitrile,
1-{[2-(2-fluorophenyl)-3-oxo-2,3-dihydro-1H-benzo[e]isoindol-5-yl]methyl}-4-(4-methylpyridin-2-yl)piperidine-4-carbonitrile,
2-(2-fluorophenyl)-5-{[1-(pyridin-4-yl)-3,4-dihydroisoquinolin-2(1H)-yl]methyl}-1,2-dihydro-3H-benzo[e]isoindol-3-one,
2-(2-fluorophenyl)-5-{[4-(pyridin-2-yl)piperazin-1-yl]methyl}-1,2-dihydro-3H-benzo[e]isoindol-3-one,
2-(2-fluorophenyl)-5-{[4-(pyridin-2-yl)piperazin-1-yl]methyl}-1,2-dihydro-3H-benzo[e]isoindol-3-one,
and pharmaceutically acceptable salts thereof.

13. A pharmaceutical composition comprising a therapeutically effective amount of a compound of claim 1, or a pharmaceutically acceptable salt thereof, and a pharmaceutically acceptable carrier.

* * * * *